US012698318B2

(12) United States Patent (10) Patent No.: US 12,698,318 B2
Sekaly et al. (45) Date of Patent: Aug. 4, 2026

(54) LONG LIVED T CELLS FOR TREATING HIV INFECTION

(71) Applicant: CASE WESTERN RESERVE UNIVERSITY, Cleveland, OH (US)

(72) Inventors: Rafick-Pierre Sekaly, Cleveland, OH (US); Ashish Sharma, Cleveland, OH (US); Joumana Zeidan, Cleveland, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 1076 days.

(21) Appl. No.: 17/627,947

(22) PCT Filed: Jul. 17, 2020

(86) PCT No.: PCT/US2020/042567
§ 371 (c)(1),
(2) Date: Jan. 18, 2022

(87) PCT Pub. No.: WO2021/011882
PCT Pub. Date: Jan. 21, 2021

(65) Prior Publication Data
US 2023/0149457 A1     May 18, 2023

Related U.S. Application Data

(60) Provisional application No. 62/875,217, filed on Jul. 17, 2019.

(51) Int. Cl.
| | |
|---|---|
| *C07K 14/705* | (2006.01) |
| *A61K 40/11* | (2025.01) |
| *A61K 40/46* | (2025.01) |
| *A61K 45/06* | (2006.01) |
| *A61P 31/18* | (2006.01) |
| *C07K 14/715* | (2006.01) |
| *C12N 5/0783* | (2010.01) |
| *C12N 15/90* | (2006.01) |

(52) U.S. Cl.
CPC ........ *C07K 14/70589* (2013.01); *A61K 40/11* (2025.01); *A61K 40/46* (2025.01); *A61K 45/06* (2013.01); *A61P 31/18* (2018.01); *C07K 14/7158* (2013.01); *C12N 5/0636* (2013.01); *C12N 15/907* (2013.01); *A61K 2239/38* (2023.05); *C12N 2501/15* (2013.01); *C12N 2501/2307* (2013.01); *C12N 2501/2315* (2013.01)

(58) Field of Classification Search
None
See application file for complete search history.

(56) References Cited

U.S. PATENT DOCUMENTS

| | | | |
|---|---|---|---|
| 5,176,996 | A | 1/1993 | Hogan et al. |
| 5,422,251 | A | 6/1995 | Fresco |
| 5,585,245 | A | 12/1996 | Johnsson et al. |
| 5,789,538 | A | 8/1998 | Rebar et al. |
| 5,925,523 | A | 7/1999 | Dove et al. |
| 6,007,988 | A | 12/1999 | Choo et al. |
| 6,010,902 | A | 1/2000 | Ledbetter et al. |
| 6,013,453 | A | 1/2000 | Choo et al. |
| 6,140,081 | A | 10/2000 | Barbas |
| 6,200,759 | B1 | 3/2001 | Dove et al. |
| 6,432,405 | B1 | 8/2002 | Weinberg et al. |
| 6,453,242 | B1 | 9/2002 | Eisenberg et al. |
| 6,534,261 | B1 | 3/2003 | Cox, III et al. |
| 6,692,964 | B1 | 2/2004 | June et al. |
| 8,586,526 | B2 | 11/2013 | Gregory et al. |
| 8,975,069 | B2 | 3/2015 | Kelleher et al. |
| 10,023,840 | B2 | 7/2018 | Sykes et al. |
| 2004/0209363 | A1 | 10/2004 | Watts et al. |
| 2005/0064474 | A1 | 3/2005 | Urnov et al. |
| 2007/0218528 | A1 | 9/2007 | Miller et al. |
| 2008/0131962 | A1 | 6/2008 | Miller |
| 2011/0059012 | A1 | 3/2011 | Turtle et al. |
| 2011/0201055 | A1 | 8/2011 | Doyon et al. |
| 2014/0101786 | A1 | 4/2014 | Sykes et al. |
| 2016/0175358 | A1 | 6/2016 | Jakobovits et al. |
| 2017/0136063 | A1 | 5/2017 | Perez et al. |
| 2020/0347456 | A1* | 11/2020 | Regev .................... G16B 40/30 |

FOREIGN PATENT DOCUMENTS

| | | | |
|---|---|---|---|
| WO | 199519431 | A1 | 7/1995 |
| WO | 199606166 | A1 | 2/1996 |
| WO | 199844350 | A1 | 10/1998 |
| WO | 199853057 | A1 | 11/1998 |
| WO | 199853058 | A1 | 11/1998 |

(Continued)

OTHER PUBLICATIONS

Didiju et al. Simultaneous zinc-finger nuclease editing of the HIV coreceptors ccr5 and cxcr4 protects CD41 T cells from HIV-1 infection. Blood, vol. 123, No. 1, Jan. 2, 2014. (Year: 2014).*
BD Biosciences. Human and Mouse CD Marker Handbook. 2016 (Year: 2016).*
Xu et al. Closely related T-memory stem cells correlate with in vivo expansion of CAR.CD19-T cells and are preserved by IL-7 and IL-15. Blood, Jun. 12, 2014 (Year: 2014).*
Ren et al. Amino-acid transporters in T-cell activation and differentiation. (2017) 8, e2655. (Year: 2017).*

(Continued)

*Primary Examiner* — Gary B Nickol
*Assistant Examiner* — Amy M. Chattin
(74) *Attorney, Agent, or Firm* — Tarolli, Sundheim Covell & Tummino LLP

(57) ABSTRACT

A method of treating an HIV infected subject includes administering the subject an enriched CCR5 and/or CXCR4 gene edited CD4+ T cell population characterized by intermediate cells surface co-expression of CD45A and CD450 ($RA^{int}RO^{int}$).

16 Claims, 41 Drawing Sheets

(56)         References Cited

FOREIGN PATENT DOCUMENTS

| WO | 199853059 A1 | 11/1998 | |
| WO | 199853060 A1 | 11/1998 | |
| WO | 199854311 A1 | 12/1998 | |
| WO | 2000027878 A1 | 5/2000 | |
| WO | 200160970 A3 | 8/2001 | |
| WO | 200188197 A2 | 11/2001 | |
| WO | 200216536 A1 | 2/2002 | |
| WO | 20020099084 A2 | 12/2002 | |
| WO | 2003016496 A3 | 2/2003 | |
| WO | 20160109410 A2 | 7/2016 | |
| WO | WO-2017193107 A2 * | 11/2017 | ............. A61P 35/00 |
| WO | WO2019070755 A1 | 4/2019 | |
| WO | WO-2019191314 A1 * | 10/2019 | ............. A61P 31/18 |

OTHER PUBLICATIONS

Tian et al. Unique phenotypes and clonal expansions of human CD4 effector memory T cells re-expressing CD45RA.. Nature Communications, DOI: 10.1038/s41467-017-01728-5, 2017. (Year: 2017).*

Cerwenka et al. TGF-beta 1 is a potent inducer of human effector T cells. J Immunol (1994) 153 (10): 4367-4377. (Year: 1994).*

Fischer et al. The Insulin Receptor Plays a Critical Role in T Cell Function and Adaptive Immunity. J Immunol (2017) 198 (5): 1910-1920. (Year: 2017).*

Kim et al. Adherence to antiretroviral therapy and factors affecting low medication adherence among incident HIV-infected ndividuals. (2018) 8:3133. (Year: 2018).*

Ren et al. Amino-acid transporters in T-cell activation and differentiation. Cell Death and Disease (2017) 8, e2655. (Year: 2017).*

Oh and Li. TGF-B: Guardian of T cell Function. J Immunol. Oct. 15, 2013; 191(8): 3973-3979. (Year: 2013).*

Angin, et al.; Metabolic Plasticity of HIV-Specific CD8+ T Cells is Associated With Enhanced Antiviral Potential and Natural Control of HIV-1 Infection, p. 706, col. 2, Para 2; Jul. 12, 2019; (online publication date), Nature Metabolism, vol. 1, pp. 704-716; p. 706, col. 2, Para 2.

Taco W. Kuijpers, et al.; "A reversion of an IL2RG mutation in combined immunodeficiency providing competitive advantage to the majority of CD8+ T cells. Haematologica"; 2013;98(7):1030-1038; https://doi.org/10.3324/haematol.2012.077511.

Matheson, Nicholas J., et al. "Cell surface proteomic map of HIV infection reveals antagonism of amino acid metabolism by Vpu and Nef." Cell Host & Microbe, 2015; pp. 409-423; abstract.

Applicant: Case Western Reserve University; PCT International Application No. PCT/US20/42567 Filed Jul. 17, 2020; PCT International Search Report and Written Opinion; Authorized Officer: Lee Young; Date of Mailing: Dec. 15, 2020; 14 pgs.

Chinese Application No. 202080065112.9, Office Action dated Feb. 28, 2024.

Champagne, Patrick et al.: "Skewed maturation of memory HIV-specific CD8 T lymphocytes", Nature, vol. 410, No. 6824, Mar. 1, 2001 (Mar. 1, 2001), pp. 106-111.

Chinese Application No. 202080065112.9, Office Action dated Jun. 29, 2023.

European Application No. 20841108.2, Search Report dated Jun. 16, 2023.

Gosselin, Annie, et al., "Peripheral Blood CCR4 + CCR6 + and CXCR3 + CCR6 + CD4 + T Cells Are Highly Permissive to HIV-1 Infection" , The Journal of Immunology, vol. 184, No. 3, Dec. 30, 2009 (Dec. 30, 2009), pp. 1604-1616.

Helbert, MR et al: "HIV infection of CD45RA+ and CD45RO+ CD4+ T cells", Clinical and Experimental Immunology, Wiley-Blackwell Publishing Ltd, GB, vol. 107, No. 2, Dec. 22, 2003 (Dec. 22, 2003), pp. 300-305.

Japanese Application No. 2022-503015, Office Action dated Aug. 13, 2024.

European Application No. 19803945.5, Office Action dated Apr. 7, 2025.

Hamann, D., et al.; "Heterogeneity of the Human CD4+ T-cell Population: two distinct CD4+ T-cell subsets characterized by coexpression of CD45RA and CD45RO isoforms"; Blood, vol. 88, No. 9, Nov. 1, 1996, pp. 3513-3521.

Japanese Application No. 2022-503015, Office Action dated Apr. 15, 2025.

Molecular Therapy, 2015, vol. 23, supplement 1, p. S102.

Canadian Application No. 3,100,837, Office Action dated Oct. 24, 2025.

Canadian Application No. 3,144,413, Office Action dated Dec. 12, 2025.

Korean Application No. 10-2022-7005199, Office Action dated Nov. 12, 2025.

Oh, Soyoung A., et al. TGF-b: Guardian of T Cell Function, J Immunol. Oct. 15, 2013, 191(8):3973-3979.

Ren, Wenkai, et al. Amino-acid transporters in T-cell activation and differentiation, Cell Death and Disease (2017) 8, e2655.

Tebas, Pablo, et al. Gene Editing of CCR5 in Autologous CD4 T Cells of Persons Infected with HIV, engl j med 370;10 nejm.org Mar. 6, 2014.

Australian Application No. 2020314956, Examination Report dated Jan. 27, 2026.

* cited by examiner

COMBINED LEADING EDGE GENES

SB-728-T Products

Year 3-4 a b

LONG LIVED T CELLS FOR TREATING HIV INFECTION

RELATED APPLICATION

This application claims priority from U.S. Provisional Application No. 62/875,217, filed Jul. 17, 2019, the subject matter of which is incorporated herein by reference in its entirety.

GOVERNMENT FUNDING

This invention was made with government support under CA043703 awarded by the National Institutes of Health. The government has certain rights in the invention.

BACKGROUND

The presence of a small pool of latently infected cells has been a major impediment to stopping anti-retroviral treatment (ART) and to human immunodeficiency virus (HIV) eradication. Although ART can durably suppress viral replication, HIV persists indefinitely, requiring infected individuals to remain on complex antiretroviral drug regimens for life. The ability of ART to reconstitute immune function is highly variable. A subset of individuals (up to 45%) fails to exhibit complete restoration of CD4+ T cell counts even after years of effective ART. Impaired CD4+ T cell recovery has been associated with a number of host-related and HIV-related factors, such as impaired thymopoiesis and homeostasis. As low CD4+ T cell counts in individuals on ART have been associated with increased risk of cancer and other diseases, novel therapeutic approaches to enhance immune function in such individuals are needed.

Studies modeling the latent HIV reservoir have shown that there was minimal decay of total and integrated HIV DNA 4 years post ART initiation, especially in individuals in whom ART was initiated in the chronic phase of infection. Several mechanisms contribute to HIV persistence, including "latent" infection of long-lived memory CD4+ T cells that are maintained by homeostatic proliferation, dysfunctional host clearance mechanisms, and possibly residual viral replication. Intriguingly, all these mechanisms are exacerbated in immunologic non-responders and have been associated with higher HIV reservoir size. Therefore, enhancing the recovery of CD4+ T cells may contribute to the reduction of the HIV reservoir during ART.

CCR5 is one of the major co-receptors for HIV entry. The therapeutic concept of providing HIV-infected subjects with a CCR5 deficient immune compartment was demonstrated with the "Berlin Patient", who has been HIV-free since receiving allogeneic bone marrow transplants of CD34+ stem cells from a homozygous CCR5432 matched donor. While these results are encouraging, a less invasive and a more broadly applicable treatment strategy would be desirable. One approach is to reconstitute immune function through adoptive transfer of autologous T cells, which was successfully deployed in other viral infections, including cytomegalovirus and Epstein-Barr virus, but largely failed in HIV infection, partly because CD4+ T cells remain susceptible to HIV infection. A recent trial in which adoptive transfer of zinc finger nuclease (ZFN)-mediated CCR5 gene edited CD4 T cells (SB-728-T products) was performed in a group of HIV-infected adults has shown that this infusion was safe, well tolerated and led to increased CD4+ T cell counts and decreased HIV reservoir.

SUMMARY

Embodiments described herein relate to a long-lived enriched population of CD4 T cells and CD 8 T cells (CD4/CD8 T cells) having a $CD45RA^{int}CD45RO^{int}$ phenotype, genetically modified and/or altered CD4/CD8 T cells having a $CD45RA^{int}CD45RO^{int}$ phenotype, and to their use in treating an HIV infected subject and particularly a latent HIV infection of a subject that has undergone and/or continues to undergo antiretroviral therapy. It was found that a subset CD4/CD8 T cells has phenotypic and molecular attributes of long-lived pluripotent stem cells. Like other known stem cell populations, this subset population has a low metabolic profile (upregulation of fatty acid metabolism and oxidative phosphorylation, and down regulation of cell cycling pathways), retains the capacity to self-renew, and can differentiate to effector cells. This subset is primarily characterized by intermediate co-expression of CD45RA and CD45RO ($CD45RA^{int}CD45RO^{int}$). CD4/CD8 T cells having a $CD45RA^{int}CD45RO^{int}$ phenotype can also express CD95 (Fas) CD127 (IL7R) and CD27. Addition of low doses of cytokines IL-7 and IL-15 can lead to the formation of an enriched population of CD4/CD8 cells having the $CD45RA^{int}CD45RO^{int}$ phenotype; while high doses of cytokines IL-7 and IL-15 can lead to effector differentiation of the cells.

CD4/CD8 T cells having a $CD45RA^{int}CD45RO^{int}$ phenotype can be genetically modified such that they are devoid of a functional CCR5 and/or CXCR4 HIV co-receptor. Administration of CCR5 and/or CXCR4 gene edited autologous CD4/CD8 T cells having a $CD45RA^{int}CD45RO^{int}$ phenotype to an HIV infected subject can provide sustained increases in CD4+ T cell counts, restored T cell homeostasis, and a sizable decline in the size of the HIV reservoir in the subject.

In some embodiments, a method of generating an enriched population of CD4/CD8 T cells having a $CD45RA^{int}CD45RO^{int}$ phenotype, which can be genetically modified such that the CD4/CD8 T cells are devoid of a functional CCR5 and/or CXCR4 HIV co-receptor includes isolating T-cells from a biological sample of a subject. The biological sample can include a T cell containing sample, such as peripheral blood mononuclear cells, of a subject having HIV to be treated, i.e., autologous T-cells from the subject to be treated. The isolated T cells can include CD4+ T cells and/or CD8+ T cells A population of CD4/CD8 T cells having a $CD45RA^{int}CD45RO^{int}$ phenotype can be separated from the isolated T-cells. In some embodiments, the CD4/CD8 T cells can be genetically modified such that the CD4/CD8 T cells are devoid of a functional CCR5 and/or CXCR4 HIV co-receptor before separating the population of CD4/CD8 T cells having the $CD45RA^{int}CD45RO^{int}$ phenotype from the isolated T-cells. In other embodiments, the population of CD4/CD8 T cells having the $CD45RA^{int}CD45RO^{int}$ phenotype can be genetically modified after separation from the isolated T-cells such that the population of CD4/CD8 T cells having the $CD45RA^{int}CD45RO^{int}$ phenotype are devoid of a functional CCR5 and/or CXCR4 HIV co-receptor.

In some embodiments, the isolated CD4/CD8 T-cell are genetically modified by at least one of transduction, transfection, and/or electroporation to inactivate a gene encoding CCR5 and/or CXCR4 in the cells.

In some embodiments, the separated CD4/CD8 T cells can express at least one of CD95, CD127, or CD27. In other embodiments, the separated CD4/CD8 T cells can intermediately express 4-1BB and optionally express OX40.

In other embodiments, the separated CD4/CD8 T-cells can express at least one of, at least two of, at least three of, at least four of, at least five of or more of IL17RA, CD5, IL2RG, IGF2R, SLC38A1, IL7R, SLC44A2, SLC2A3, CD96, CD44, CD6, CCR4, IL4R, or SLC12A7.

In some embodiments, the separated CD4/CD8 T cells can have a CD45RA$^{int}$CD45RO$^{int}$CD95+CD127+CD27+ phenotype. In other embodiments, the separated T-cells can have a CD45RA$^{int}$CD45RO$^{int}$CD95+CD127+CD27+IL7R+ CD44+ SCL38A1+IL2RG+CD6+CD5+ phenotype.

In other embodiments, the method can include activating the isolated CD4/CD8 T cells with an anti-CD3 antibody and/or an anti-CD28 antibody prior to genetic modification and/or separation. The activated CD4/CD8 T cells can be cultured in an amount of IL7 and IL15 effective to promote expansion and/or formation of an enriched population of CD4/CD8 T cells having a CD45RA$^{int}$CD45RO$^{int}$ phenotype. Once separated, the CD4/CD8 T-cells can be cultured in a culture medium comprising TGFβ/IL1β to maintain the CD45RA$^{int}$CD45RO$^{int}$ phenotype.

Other embodiments described herein relate to a composition that includes an enriched population of CCR5 and/or CXCR4 gene edited CD4/CD8 T cells produced by a method described herein. At least about 70%, at least about 75%, at least about 80%, at least 85%, at least about 90%, at least about 95% of the enriched population of CCR5 and/or CXCR4 gene edited CD4/CD8 T cells can have a CD45RA$^{int}$CD45RO$^{int}$ phenotype. The composition or enriched T-cell population can be administered to a subject with an HIV infection to treat the HIV infection. In some embodiments, administration of the composition or enriched T-cell population to a subject with HIV is capable of promoting at least one of a sustained increase in absolute CD4 cell numbers, restoration of HIV specific T cell immunity, and a substantial decay in HIV reservoir in the subject. In some embodiments, the subject has undergone and/or continues to undergo antiretroviral therapy.

Figure 1:
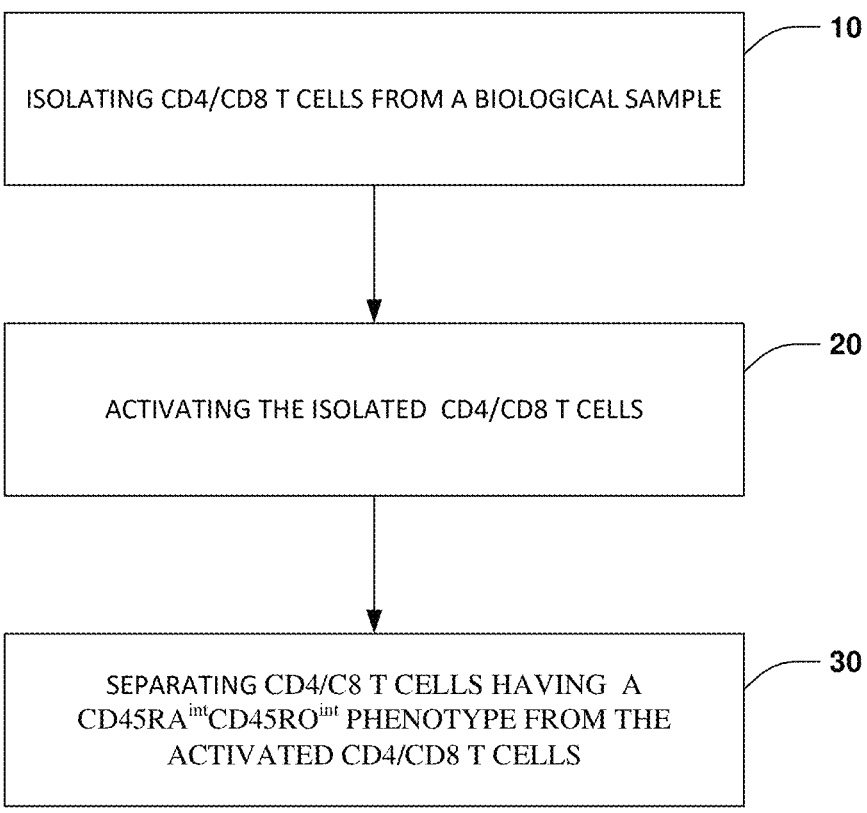
FIG. 1 is a flow diagram illustrating a method of generating an enriched population of CD4/CD8 T cells having a CD45RA$^{int}$CD45RO$^{int}$ phenotype.

of pathways enriched in genes induced or repressed in CD45RA$^{int}$RO$^{int}$ T$_{SCM}$ compared to T$_{EM}$ and T$_{CM}$ (P<0.05). Selected pathways were grouped into several biological functions; cell cycle, cell metabolism, cytokine signaling, Notch signaling and apoptosis. B, Distribution of the ZFN-mediated CCR5 mutations, determined by DNA sequencing, present uniquely in CD45RA "(CD45RO$^{int}$ CCR7+CD27+in SB-728-T products in CD4+ T cell subsets at yr 3-4 (n=5). Box shows median, first and third quartiles, and whiskers extend to a distance of 1.5*IQR. Outliers are shown as dots. C. Pie and bar charts depicting the frequency of IFN-g, IL-2, and TNF-α cytokines produced in CD4+ T cell subsets at yr 3-4 post infusion in response to anti-CD3/CD28 stimulation. Responses were averaged for each cell subset (n=6). Pie charts denote the proportion of cells producing 1, 2, or 3 functions. Arcs identify cell populations that are positive for IL-2, IFN-γ, and TNF-α. Bar graphs depict the relative frequency of the different combination of cytokine production. D. Histograms illustrating the expression of the transcription factors T-bet, Eomes, RORgt, and GATA-3 in CD4+ T cell subsets at yr 3-4 post infusion (n=7). * P<0.05; Wilcoxon rank-sum test. E, Multi-dimensional Scaling (MDS) plot highlighting the transcriptomic variance between the CD45RA$^{int}$RO$^{int}$ T$_{SCM}$ and CD45RA$^{+}$ T$_{SCM}$ subsets using Euclidean distance. The first dimension explains 27% of the transcriptomic variance between the two T$_{SCM}$ subsets. CD45RA$^{int}$RO$^{int}$ T$_{SCM}$ are shown in red and CD45RA$^{+}$ T$_{SCM}$ are shown in green (n=7). F. Heatmap of pathways identified by Gene Set Enrichment Analysis (GSEA) that are significantly enriched in CD45RA$^{int}$RO$^{int}$ T$_{SCM}$ compared to CD45RA$^{+}$ T$_{SCM}$, focusing on WNT signaling (Reactome). An aggregate geneset using the leading edge of the pre-defined pathways revealed a significant enrichment of these genes in the CD45RA$^{int}$RO$^{int}$ T$_{SCM}$ subset. Scale represents NES score with red and blue squares indicating positive and negative enrichment respectively. Columns represent CD45RA$^{int}$RO$^{int}$ T$_{SCM}$ and CD45RA$^{+}$ T$_{SCM}$ subsets. G, Co-expression network highlighting the top leading-edge genes significantly enriched within the CD45RA$^{int}$RO$^{int}$ T$_{SCM}$ subset. GeneMania algorithm was used to infer network connections and co-expression.

FIGS. 5(A-H) illustrate plots showing CCR5 gene edited T$_{SCM}$ prior to ATI correlate with control of viral load. A. Plot depicting the viral load (VL) values at week 22 (equivalent to 16 weeks of ATI) and the historic pre-ART viral set point values obtained from participants' charts (data available for 14 out of 15 participants from study 1101 cohorts 1-5). Participants with extended ATI are shown in red. P value of Wilcoxon rank-sum test is shown. B-C. Spearman rank correlations between the change of VL between week 22 and historic pre-ART viral set point with the change in CD4+ T cell counts during peak expansion (weeks 1-3 post infusion) (B) and with the frequency of the "Pentamer Duplication" marker per $10^6$ PBMCs prior to ATI (week 6) (C). Participants with extended ATI are shown in red. Dashed lines represent the 95% confidence bands. Immunological and virological assays shown in panels d-h were performed for participants of cohort 3-5 for whom cryopreserved cells were available for analysis. d-e, Box-plot with overlaid jitter showing the frequency of CCR5 gene edited alleles, determined by DNA sequencing, for CD4+ T cell subsets (naïve, CD45RA$^{+}$ T$_{SCM}$, CD45RA$^{int}$RO$^{int}$ T$_{SCM}$, T$_{CM}$, T$_{CM}$ and T$_{EM}$) at 6 weeks post infusion (pre-ATI) (D) and at 22 weeks post infusion (end of ATI) (E). Box shows median, first and third quartiles, and whiskers extend to maximum and minimum values. Participants with extended ATI are shown in red. n=7; * P<0.05; Wilcoxon rank-sum test. F-G, Spearman rank correlations between the change of VL between week 22 and historic pre-ART viral set point with (f) CD45RA$^{int}$RO$^{int}$ T$_{SCM}$ and (G) CD45RA$^{+}$ T$_{SCM}$ cell counts prior to ATI (week 6). Participants with extended ATI are shown in red. Dashed lines represent the 95% confidence bands. (n=8; Data for the historic pre-ART VL set point was missing for participant 01-060, who had extended ATI, and hence not included in VL association analysis). H. 3-D scatter plot showing the change in VL (w22—historic set point) as a function of CD45RA$^{int}$RO$^{int}$ T$_{SCM}$ cell counts and the frequency of CD8+ Try cells that produce IL-2 post gag peptide pool stimulation (using the time point with maximal response for each participant; Tmax) (n=8). A multivariate linear regression model was build using CD45RA$^{int}$RO$^{int}$ T$_{SCM}$ counts at w6 and the frequency of CD8+ T cell subsets producing IFN-γ, TNF-α, and IL-2 cytokines post gag peptide pool stimulation post infusion. The multivariate model predicting the best change in VL contained CD45RA$^{int}$RO$^{int}$ T$_{SCM}$ counts at w6 (P=0.05) and HIV-specific CD8+ Try cells producing IL-2 at Tmax (P=0.02).

FIGS. 6(A-I) illustrate plots showing levels of CCR5 gene edited T$_{EM}$ during ATI correlate with control of viral load and lower reseeding of the T$_{EM}$ HIV reservoir. A, Box-plot showing the percent of ZFN-induced CCR5 mutations present uniquely in CD45RA$^{int}$CD45RO$^{int}$ CCR7+CD27+ (T$_{SCM}$ phenotype) in SB-728-T products that are detected in CD4+ T cell subsets at weeks 6 and 22 post infusion (n=7). Box shows median, first and third quartiles, and whiskers extend to a distance of 1.5*IQR. Outliers are shown as dots. B. Schematic figure showing the dynamics of the CCR5 gene edited CD4+ T-cell dynamics (see Material & Methods for full model details and assumptions). Model Parameters are obtained by taking the geometrical mean of the 5 individual fitting results of the five participants with an extended ATI period. Parameters listed in the boxes indicate the parameters that expressed a significant correlation (≥±0.5) with the cell population magnitude obtained from the sensitivity analysis test performed in MATLAB using 100,000 bins. C-E, Spearman rank correlations between CCR5 gene edited T$_{EM}$ cell counts at the end of ATI (week 22) and CCR5 gene edited CD45RA$^{+}$ T$_{SCM}$ (C), CD45RA$^{int}$RO$^{int}$ T$_{SCM}$ (D), T$_{CM}$ (E) cell counts prior to ATI (week 6). Participants with extended ATI are shown in red. n=7. F, Box-plot with overlaid jitter representing the frequency of integrated HIV DNA within T$_{EM}$ cells at BL, week 6 and week 22 post infusion (n=7). Box shows median, first and third quartiles, and whiskers extend to maximum and minimum values. Dots and lines are shown for all participants. Participants with extended ATI are shown in red. P values of Wilcoxon rank-sum test are shown. G-H, Spearman rank correlations between the frequency of CCR5 gene edited alleles within T$_{EM}$ during viremia (week 22) and the change of viral load between week 22 (16 weeks post-ATI) and historic pre-ART viral set point (G) and the change in frequencies of T$_{EM}$ cells bearing int. HIV DNA between weeks 6 and 22 (H). Participants with extended ATI are shown in red. Dashed lines represent the 95% confidence bands. n=6; Data for the historic pre-ART VL set point was missing for participant 01-060, who had extended ATI, and hence not included in VL association analysis. I, Spearman rank correlation between the change in frequencies of T$_{EM}$ cells bearing int. HIV DNA between weeks 6 and 22 and viral load levels at week 22 (16 weeks post-ATI). Participants with extended ATI are shown in red. Dashed lines represent the 95% confidence bands. n=8.

Figure 7:
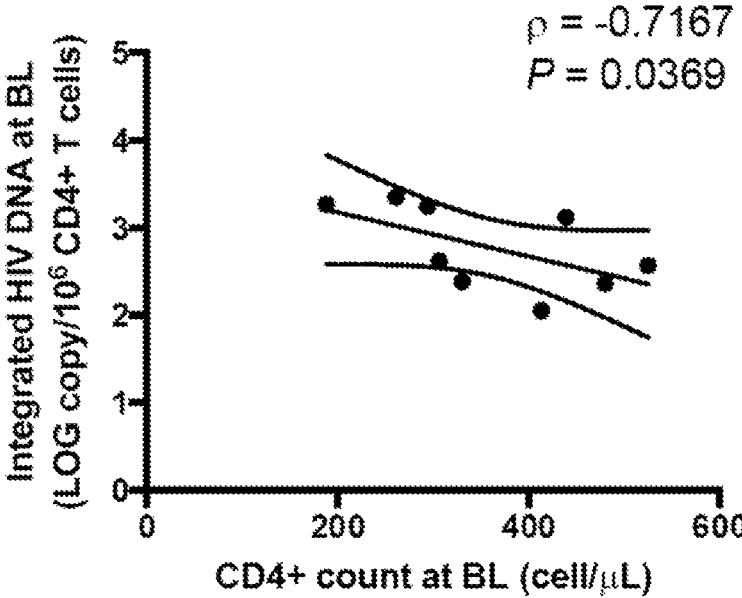

FIG. 7 illustrates a plot showing the size of the HIV reservoir in SB-728-0902 study participants at baseline. Correlation between CD4+ T cell counts at baseline (BL) and levels of integrated HIV DNA at BL measured in purified CD4+ T cells. Spearman's rho (p) test was used. Dashed lines represent the 95% confidence bands.

FIGS. 8(A-E) illustrate a single SB-728-T infusion led to a sustained increase in total CD4+ T cell counts, amelioration of the CD4: CD8 ratio, and long-term persistence of CCR5 gene edited cells. A, CD4+ T cell counts are shown at baseline (BL; 7 days prior to infusion), day 14, months 3, 6, and 12, as well as for long-term follow up time points including year 2 and a last follow up at years 3-4. The mean is shown in a black line. Wilcoxon signed rank test * P<0.05. ** P<0.01. For panels A-C. participants in cohort 1 (~1E10 infused cells) are shown in blue symbols, cohort 2 (~2E10 infused cells) in green symbols, and cohort 3 (~3E10 infused cells) in red symbols. B, The CD4: CD8 ratio is shown at BL, day 14, months 3, 6, 12, years 2 and 3-4. The mean is shown in a black line. * P<0.05. ** P<0.01; Wilcoxon signed rank test. C. The fold expansion of Pentamer Duplication-marked CD4+ T cells following infusion was estimated, as described in Material & Methods, for all 9 study participants during follow up. The grey area represents data points with a fold change below 1. D. Box-plot with overlaid jitter of Pentamer Duplication (marker of gene edited cells) per $10^6$ mononuclear cells from rectal biopsies post infusion. Box-plots show the 75th (upper edge), median (solid line in the box), and 25th percentile (lower edge). Whiskers are drawn from minimum to maximum values. E, Plots of Pentamer Duplication marker per $10^6$ PBMCs (Black circles) and mononuclear cells from lymph node biopsies (LNMCs; squares) post infusion for the 3 individuals in which the Pentamer Duplication marker was quantified in LNMCs.

Figure 9A:
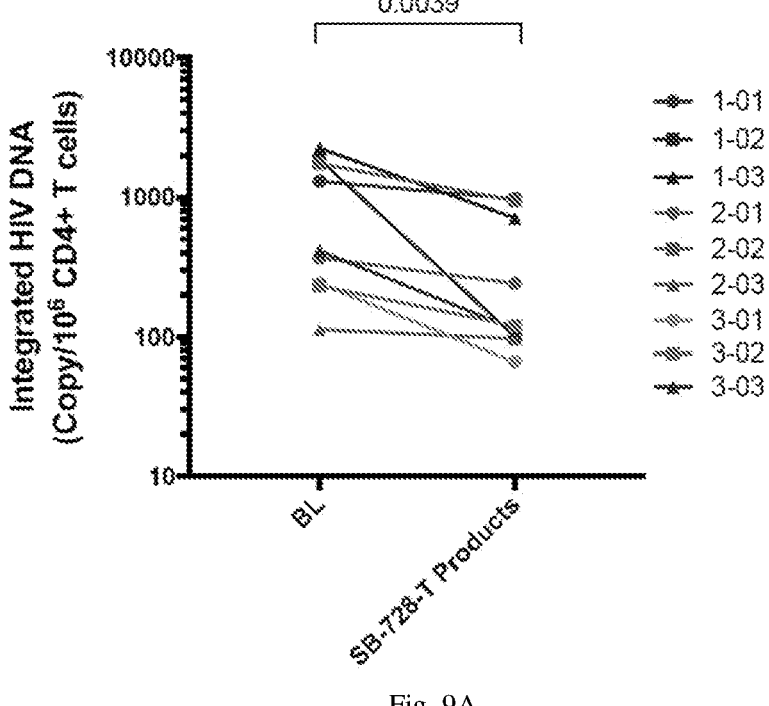
Figure 9B:
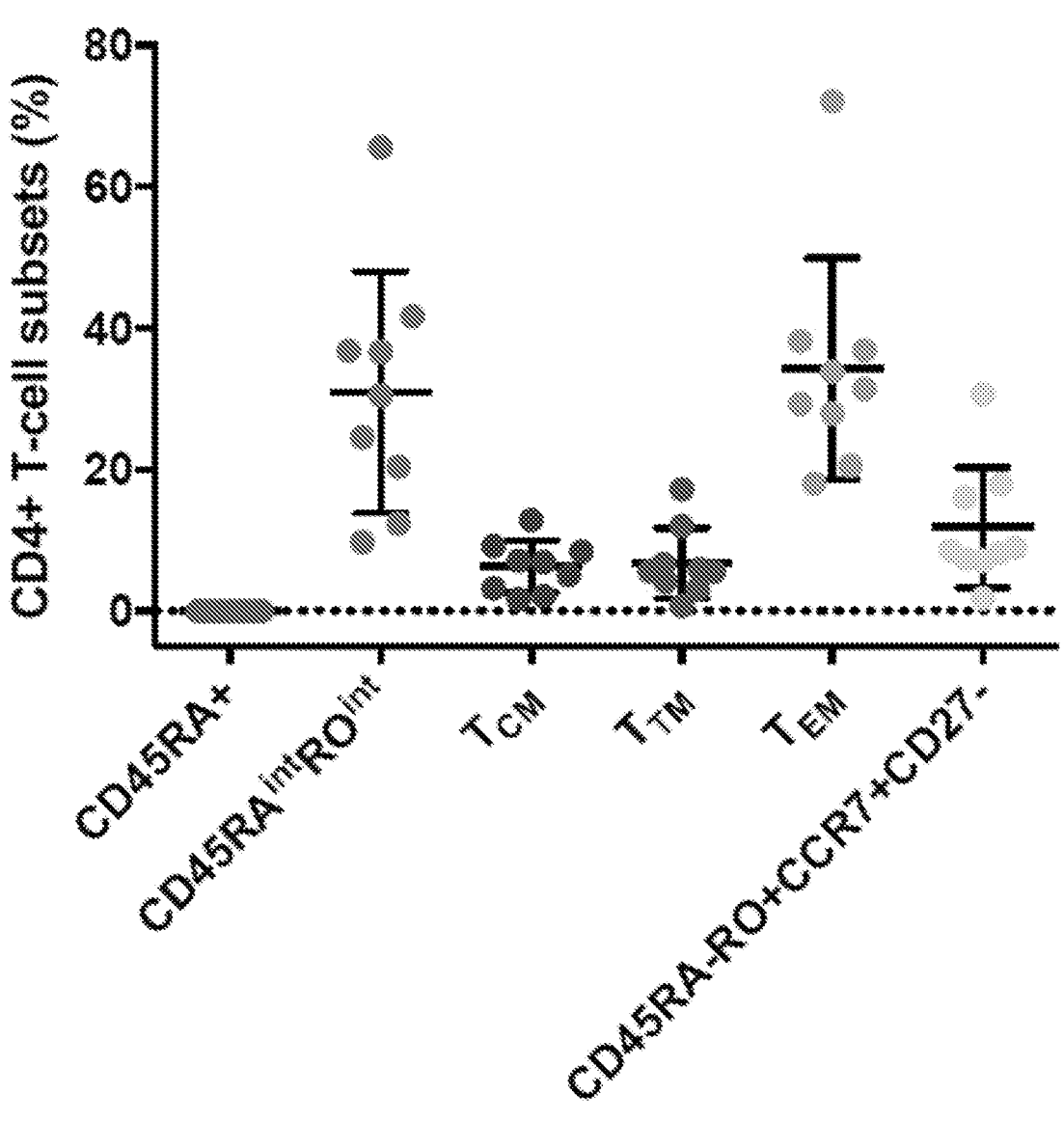
Figure 9C:
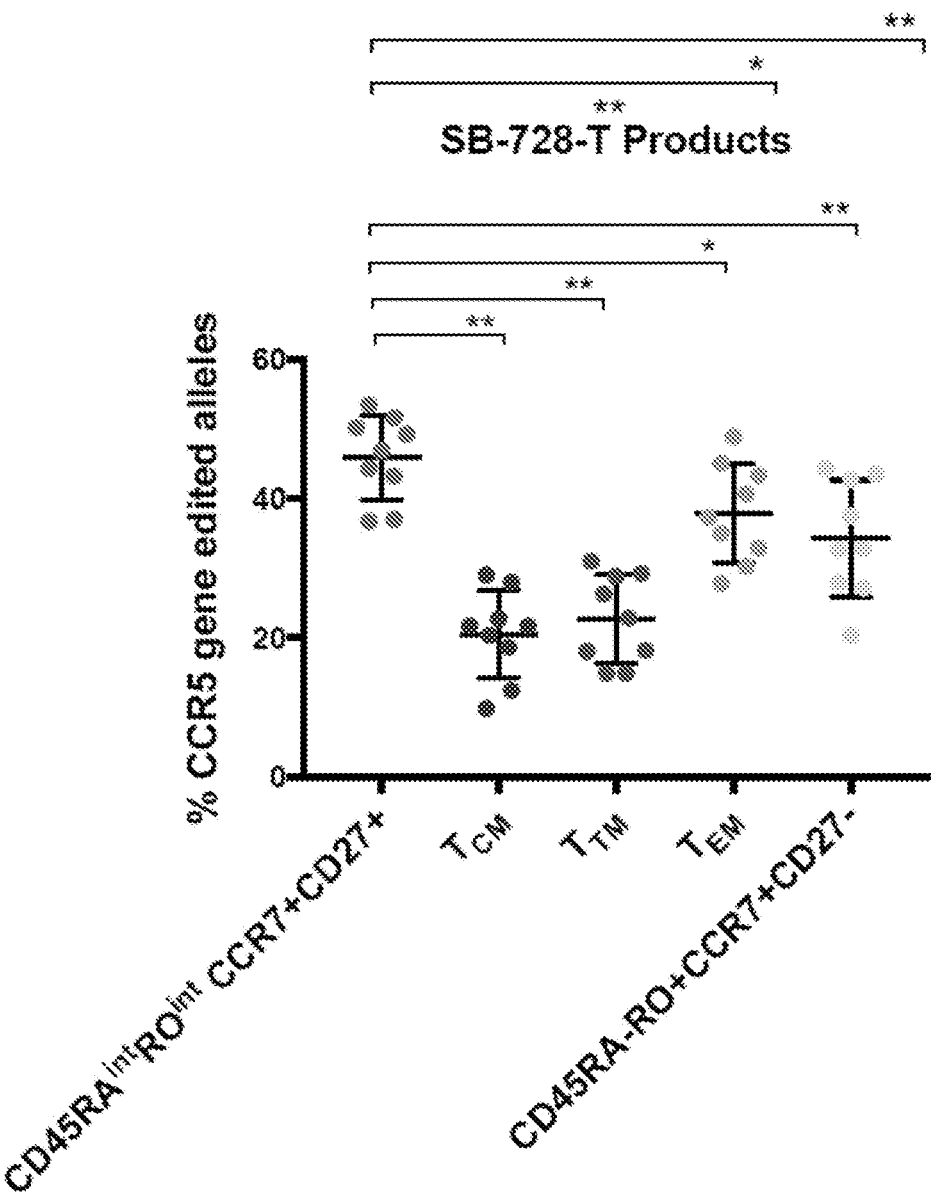

FIGS. 9(A-C) illustrate plots showing characterization of SB-728-T products. A. Levels of integrated HIV DNA in purified CD4+ T cells from pre-manufacture leukapheresis samples (BL) and post manufacture (SB-728-T products). Wilcoxon signed rank test P values shown. Live CD3+CD4+ cells were gated on CD45RA and CD45RO, followed by CCR7 and CD27 to identify naïve (CD45RA+CD45RO-CCR7+CD27+), CD45RA$^{int}$CD45RO$^{int}$ $T_{SCM}$-like cells, $T_{CM}$ (CD45RA-CD45RO+CCR7+CD27+), $T_{TM}$ (CD45RA-CD45RO+CCR7-CD27+), $T_{EM}$ (CD45RA-CD45RO+CCR7-CD27-), and CD45RA-CD45RO+CCR7+CD27+ subsets. B, Frequencies of CD4+ T cell subsets observed in SB-728-T products. Lines represent the mean and standard deviation. C. Frequencies of CCR5 gene edited alleles within CD4+ T cell subsets in SB-728-T products measured by DNA sequencing of the diverse CCR5 ZFN-induced mutations. Lines represent the mean and standard deviation. * P<0.05. ** P<0.01; Wilcoxon signed rank test.

FIGS. 10(A-F) illustrate plots showing frequencies of CD58+CD95+ cells in CD45RA$^{int}$CD45RO$^{int}$ and CD45RA+CD45RO subsets increase post infusion and contribute to persistence of CCR5 gene edited cells. A-B. Histograms showing the mean frequencies of cells expressing CD58 and CD95 in the CD45RA$^{int}$CD45RO$^{int}$ CCR7+CD27+CD127+CD28+(CD45RA$^{int}$RO$^{int}$ $T_{SCM}$; A) and CD45RA+CD45RO$^-$ CCR7+CD27+CD127+CD28+ (CD45RA+ $T_{SCM}$; B) subsets at BL (n=6), at mid (months 6-8, n=5), late (months 9-11; n=5), and long-term time points (years 3-4, n=6) post infusion. Error bars represent the standard deviation. * P<0.05, ** P<0.01; Mann-Whitney test. C-D. The frequencies of CD58$^+$CD95$^+$ cells within the CD45RA$^+$RO$^-$ and CD45RA$^{int}$RO$^{int}$ subsets at years 3-4 were correlated with the estimated fold-expansion of CCR5 gene edited CD4+ T cells in PBMCs at the long term time point (number of CCR5 gene edited alleles at years 3-4 relative to number (dose) of CCR5 gene edited alleles infused). E, Longitudinal analysis of CD45RA$^+$RO$^-$CCR7$^+$CD27$^+$CD127$^+$CD28$^+$CD58$^+$CD95$^+$ (termed CD45RA$^+$RO$^-$ $T_{SCM}$) and CD45RA$^+$RO$^-$ CCR7$^+$CD27$^+$CD127$^+$CD28$^+$CD58$^+$CD95$^+$ (termed naïve) cell counts at BL (up to 3 months before infusion), and at mid (month 6), late (months 8-11), and long-term time points (years 3-4) post-infusion for the 6 subjects in which BL analysis was performed. F. Longitudinal analysis of CD45RA$^{int}$RO$^{int}$ CCR7$^+$CD27$^+$CD127$^+$CD28$^+$CD58$^+$CD95$^+$ (termed CD45RAi$^{int}$RO$^{int}$ $T_{SCM}$) and CD45RA$^{int}$RO$^{int}$ CCR7$^+$CD27$^+$CD127$^+$CD28$^+$CD58$^-$CD95$^-$ (termed CD45RA$^{int}$RO$^{int}$ CD95$^-$) cell counts at BL (up to 3 months before infusion), and at mid (month 6), late (months 8-11), and long-term time points (up to month 44) post-infusion for the 6 subjects in which BL analysis was performed.

Figure 11:
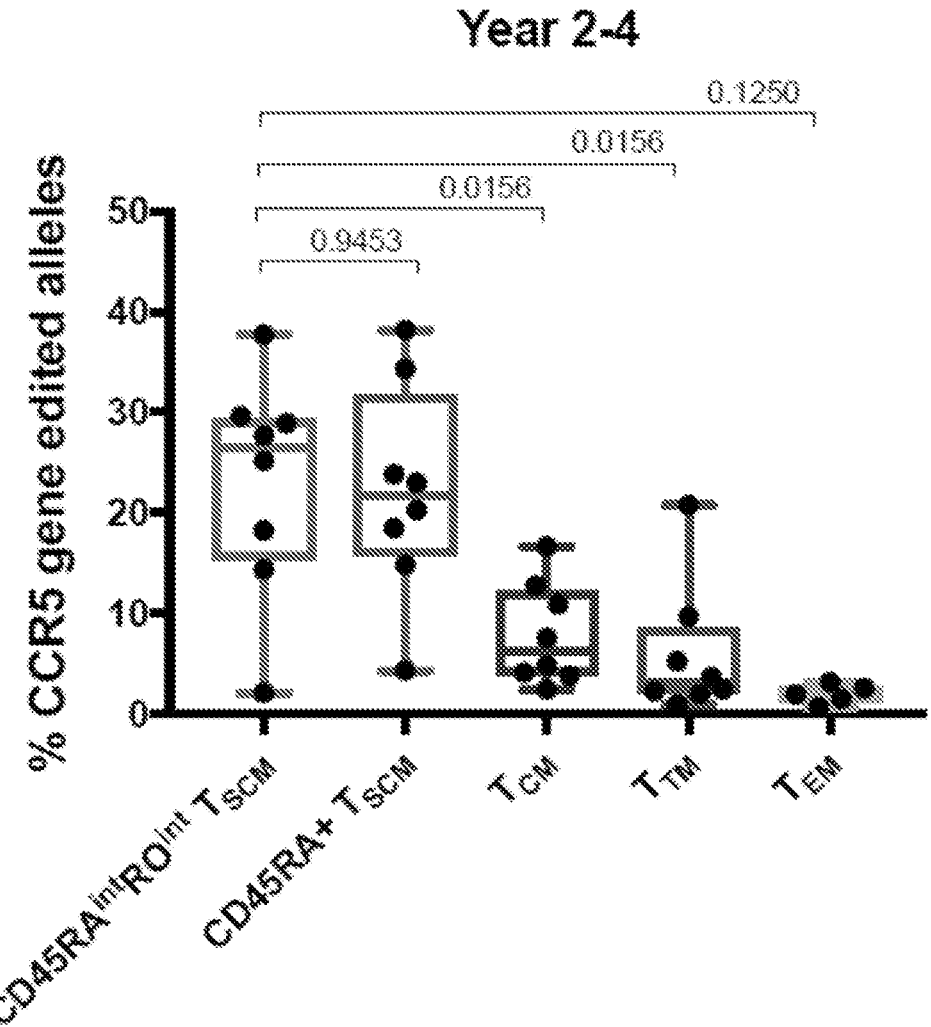

FIG. 11 illustrates a plot showing CD45RA$^{int}$RO$^{int}$ $T_{SCM}$ cells have higher levels of CCR5 gene edited alleles compared to other memory subsets. Box-plot with overlaid jitter of the frequencies of CCR5 gene edited alleles within sorted CD4+ T cell subsets at year 2-4 post infusion, measured by DNA sequencing of the diverse CCR5 ZFN-induced mutations. Lines represent the mean and standard deviation. Box plots show the 75th (upper edge), median (solid line in the box), and 25th percentile (lower edge). Whiskers are drawn from minimum to maximum values. Wilcoxon signed rank test P values shown.

Figure 12A:
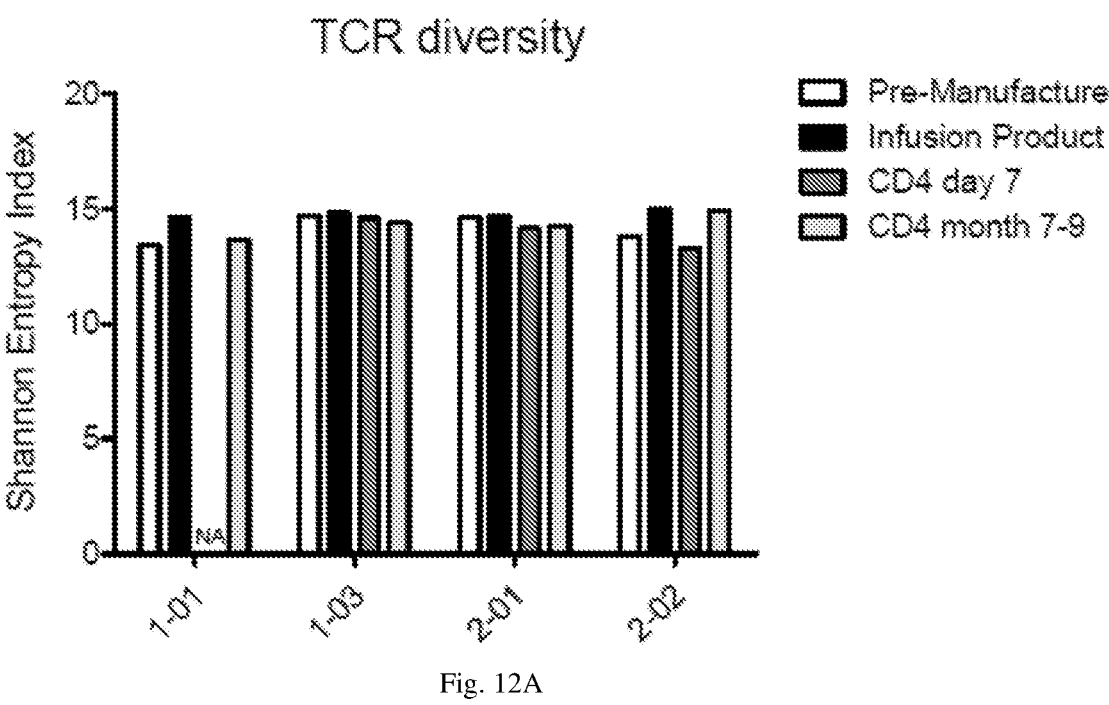
Figure 12B:
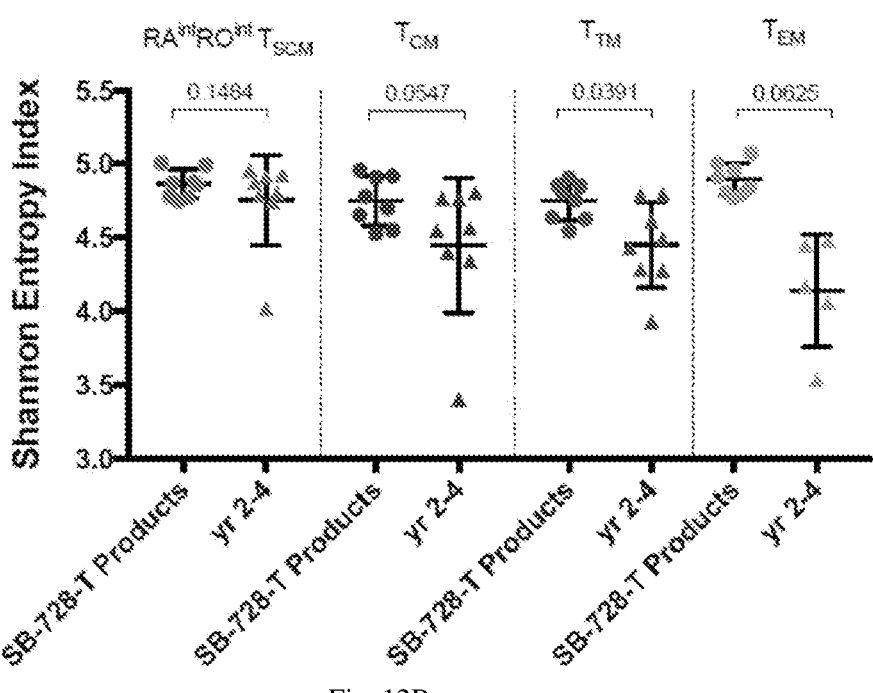

FIGS. 12(A-B) illustrate plots showing CCR5 gene edited T cells contribute to a polyclonal unbiased reconstitution of T cells. A. Bar plot showing the TCR diversity in pre-manufacture samples (CD4+ T cells purified from BL leukapheresis samples, n=4), SB-728-T products (n=4), purified CD4+ T cells at 7 days (peak of CCR5 gene edited cell expansion) (n=3) and 7-9 months post infusion (n=4). The Shannon Entropy Index was used to measure the diversity of the TCR clones. NA=sample was not available at this time point. B, Diversity of CCR5 gene edited alleles in CD4+ T cell subsets from SB-728-T products compared to that of subsets from long term time points post infusion (years 3-4)(n=8) using the Shannon Entropy Index. Lines represent the mean and standard deviation. Wilcoxon signed rank test P values shown.

Figure 13A:
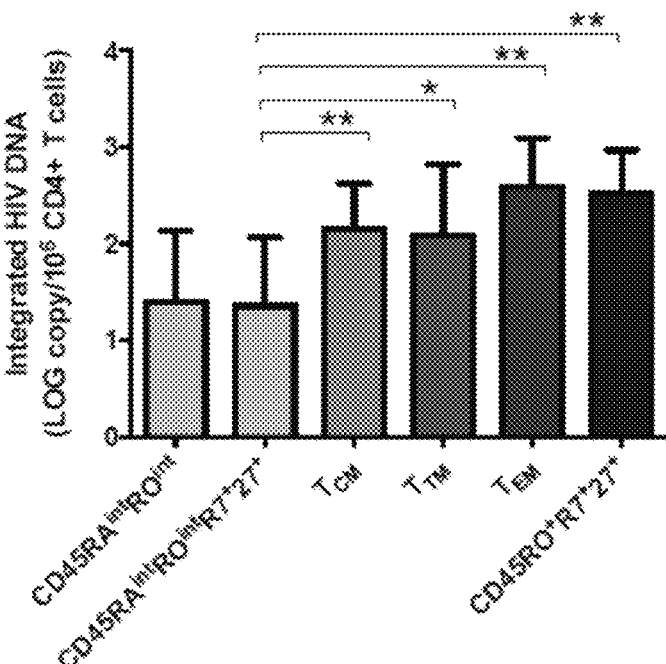
Figure 13B:
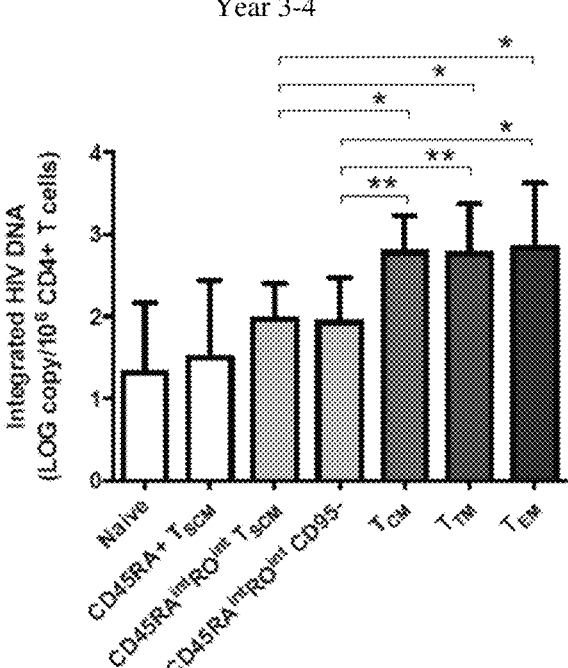

FIGS. 13(A-B) illustrate graphs showing CD45RA$^{int}$RO$^{int}$ $T_{SCM}$ cells are minor contributors of the total HIV reservoir. Histograms depicting the mean levels of integrated HIV DNA (log 10 copy/$10^6$ cells) in sorted CD45RA$^-$CD45RO$^+$subsets ($T_{CM}$, n=9; $T_{TM}$, n=8; $T_{EM}$, n=9; and CCR7+CD27-, n=9), and CD45RA$^{int}$CD45RO$^{int}$ subsets (total CD45RA$^{int}$CD45RO$^{int}$, n=9; and CD45RA$^{int}$CD45RO$^{int}$ CCR7+CD27+, n=9) in SB-728-T products (A), and in sorted CD45RA CD45RO+ subsets (($T_{CM}$, n=8; $T_{TM}$, n=7; and $T_{EM}$, n=8), CD45RA$^+$ CD45RO$^{int}$ subsets (CD95+; CD45RA+RO$^{int}$ $T_{SCM}$, n=8; and CD95-, n=8), and CD45RA+CD45RO subsets (CD95+; CD45RA$^+$ $T_{SCM}$), n=6; and CD95-; Naive, n=7) at 3-4 years post infusion (B). Error bars represent the standard deviation. * P<0.05**; P<0.01; Wilcoxon signed rank test.

Figure 14A:
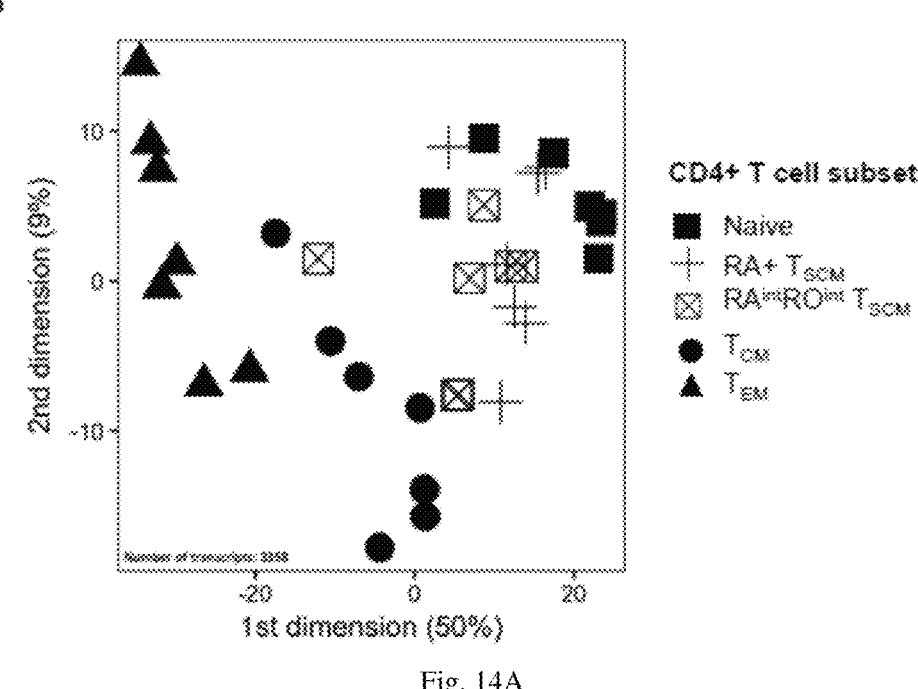
Figure 14B:
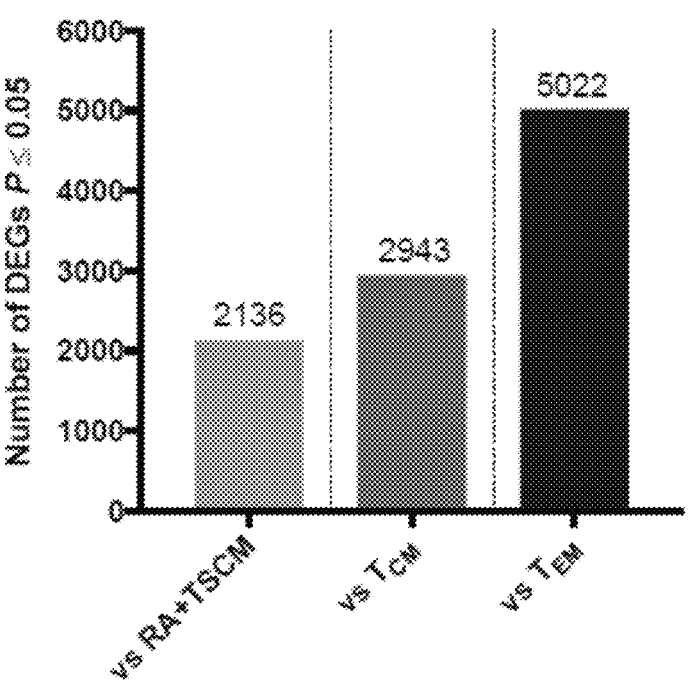

FIG. 14(A-B) illustrate plots showing CD45RA$^{int}$RO$^{int}$ $T_{SCM}$ cells constitute a distinct population than the previously described CD45RA$^+$ $T_{SCM}$ subset. A, Multi-dimensional Scaling (MDS plot) was used to highlight the transcriptomic variance of CD4+ T cell subsets at yr 3-4 post infusion. Euclidean distance was used and dimension reduction of the top variant genes based on a ANOVA (analysis of variance, F-test, n=3358 transcripts, P≤0.05) is represented. The 1st dimension explains 50% of the variance between CD4+ T cell subsets. Different subsets are represented by different symbols, n=7 samples per cell subset. B, Bar plot representing the number of differentially expressed genes (DEGs; P<0.05) between CD45RA$^{int}$RO$^{int}$ T$_{SCM}$ and CD45RA$^+$ T$_{SCM}$, T$_{CM}$, or T$_{EM}$.

Figure 15A:
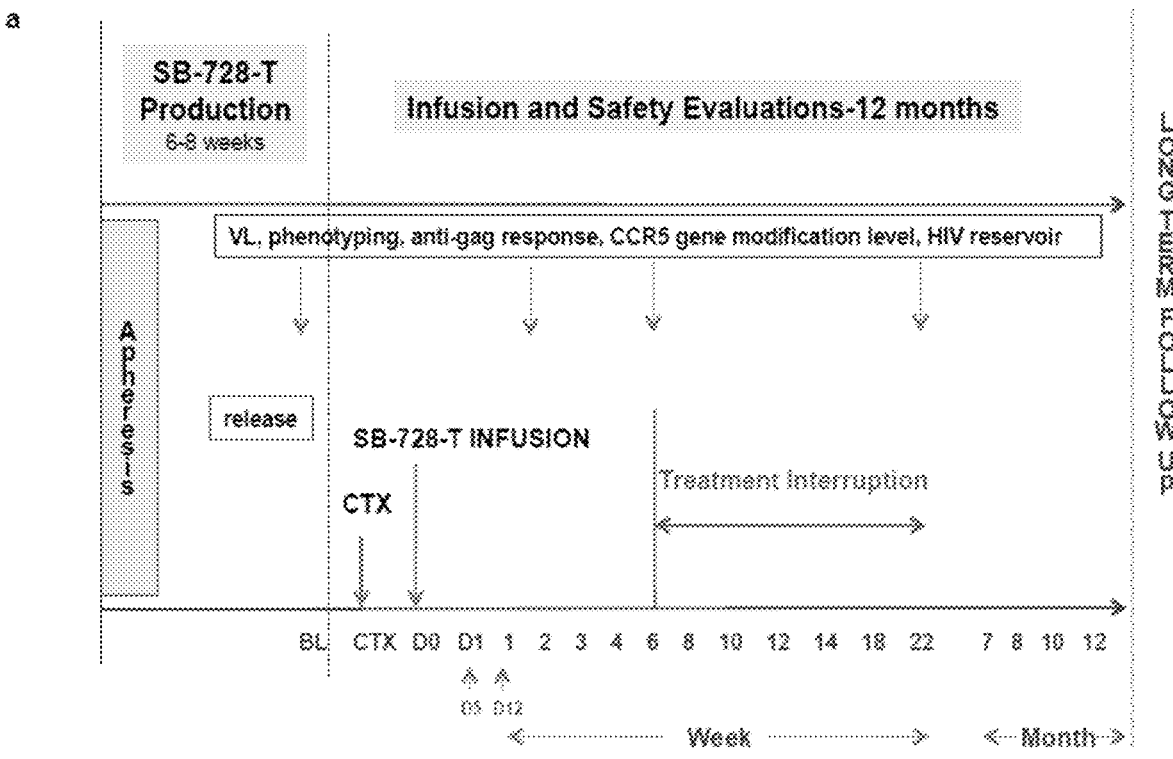
Figure 15B:
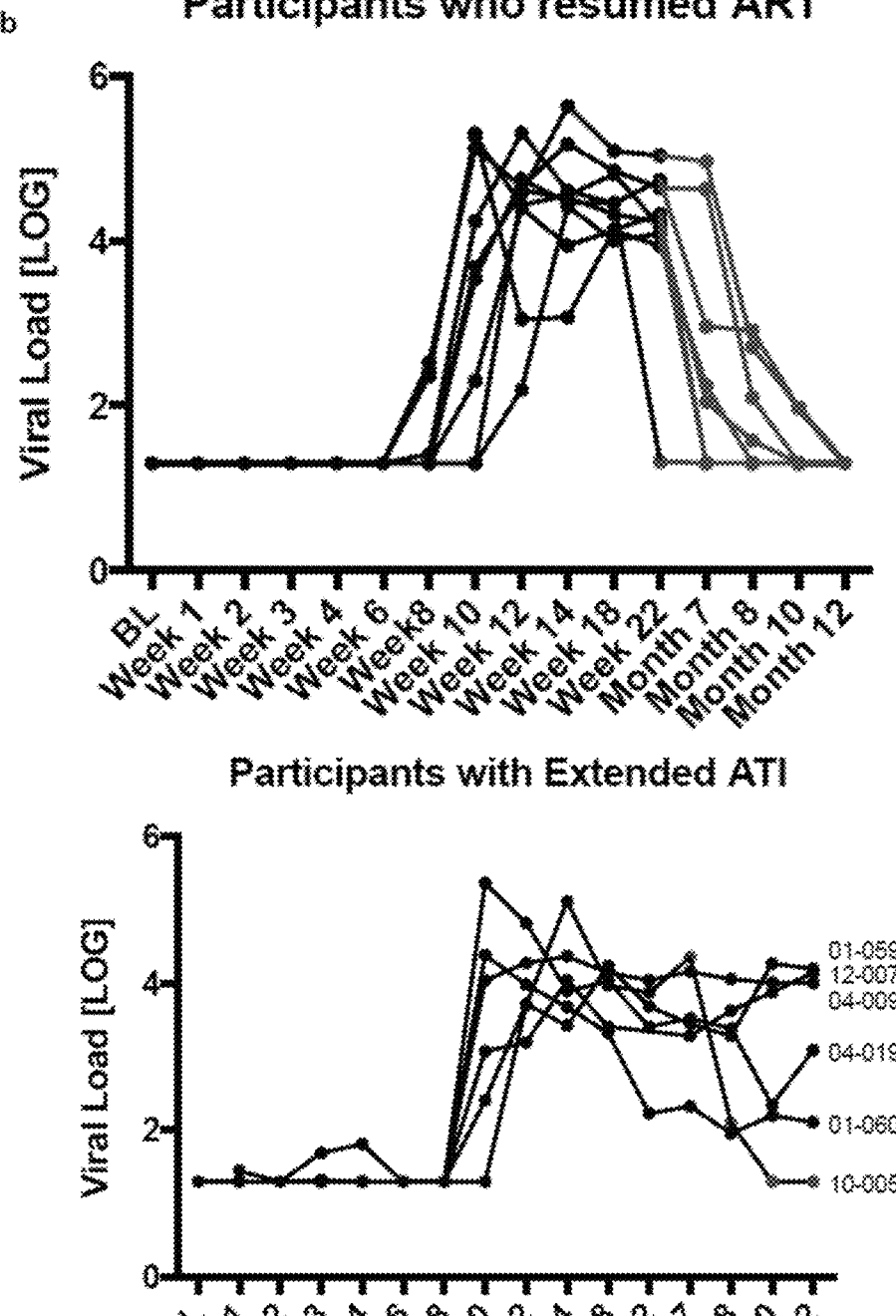

FIG. 15(A-B) illustrate plots showing viral loads of subjects who underwent analytical treatment interruption (ATI) post SB-728-T infusion in the 1101 study. A. Summary of the 1101 clinical trial. Subjects received an escalating dose of cytoxan (CTX) pre-conditioning 2 days prior to infusion. Subjects underwent an ATI at six weeks post infusion for an interval of 16 weeks. B, Viral loads (VL) are shown for the 9 subjects who resumed ART by week 22, and for the 6 subjects in which ATI was extended (for whom VL remained below 10,000 copies/mL and CD4+ T cell counts above 500 cells/µl). Red lines depict ART resumption.

Figure 16A:
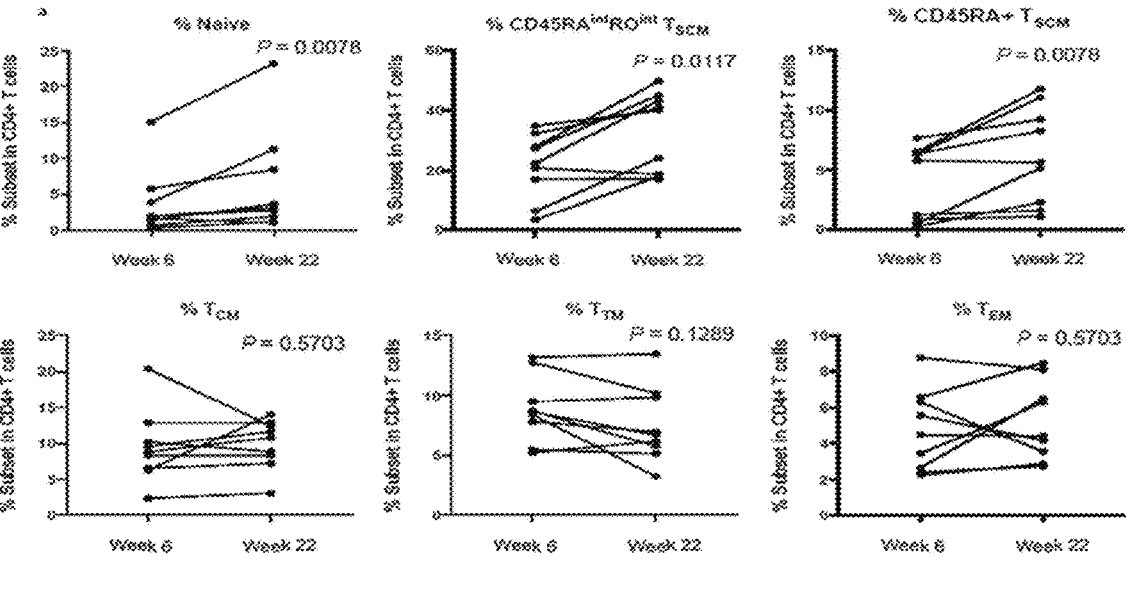
Figure 16B:
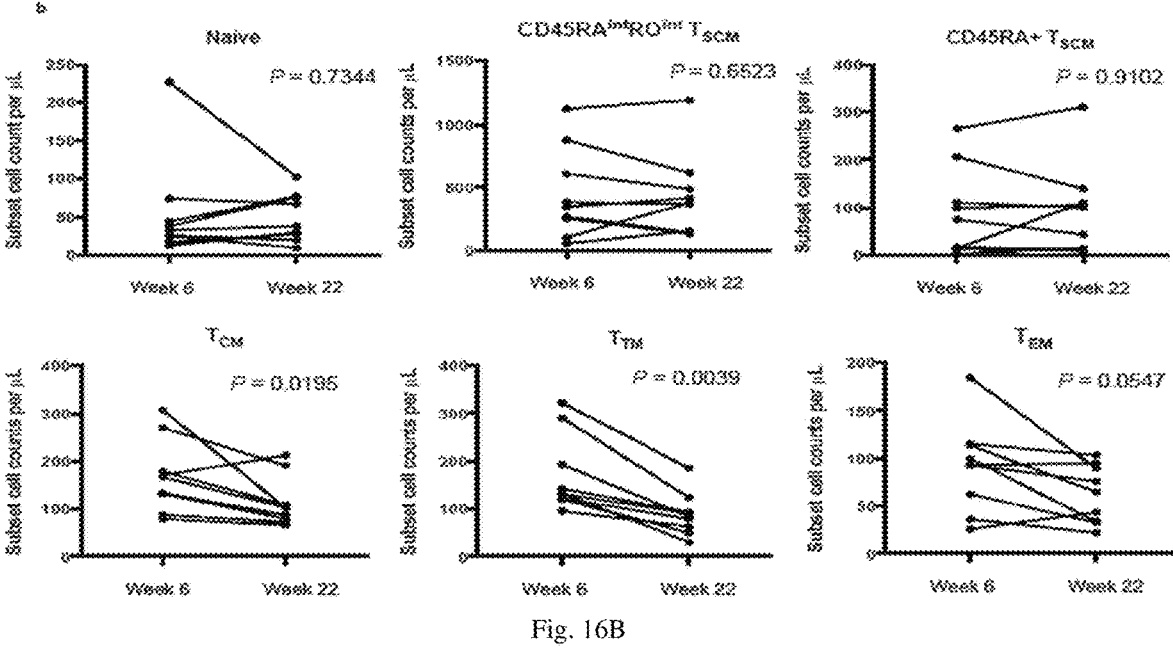

FIGS. 16(A-B) illustrate plots showing CD4+ T cell subset distribution and cell counts post infusion (week 6) and post treatment interruption (week 22) in the 1101 study. The frequency (A) and cell counts (B) of CD4 T cell subsets (naïve, CD45RA$^+$ T$_{SCM}$, CD45RA$^{int}$RO$^{int}$ T$_{SCM}$, T$_{CM}$, T$_{TM}$ and T$_{EM}$) are shown at 6 weeks post infusion (pre-ATI) and at 22 weeks post infusion (end of ATI); n=9. Wilcoxon signed rank test P values are shown.

Figure 17:
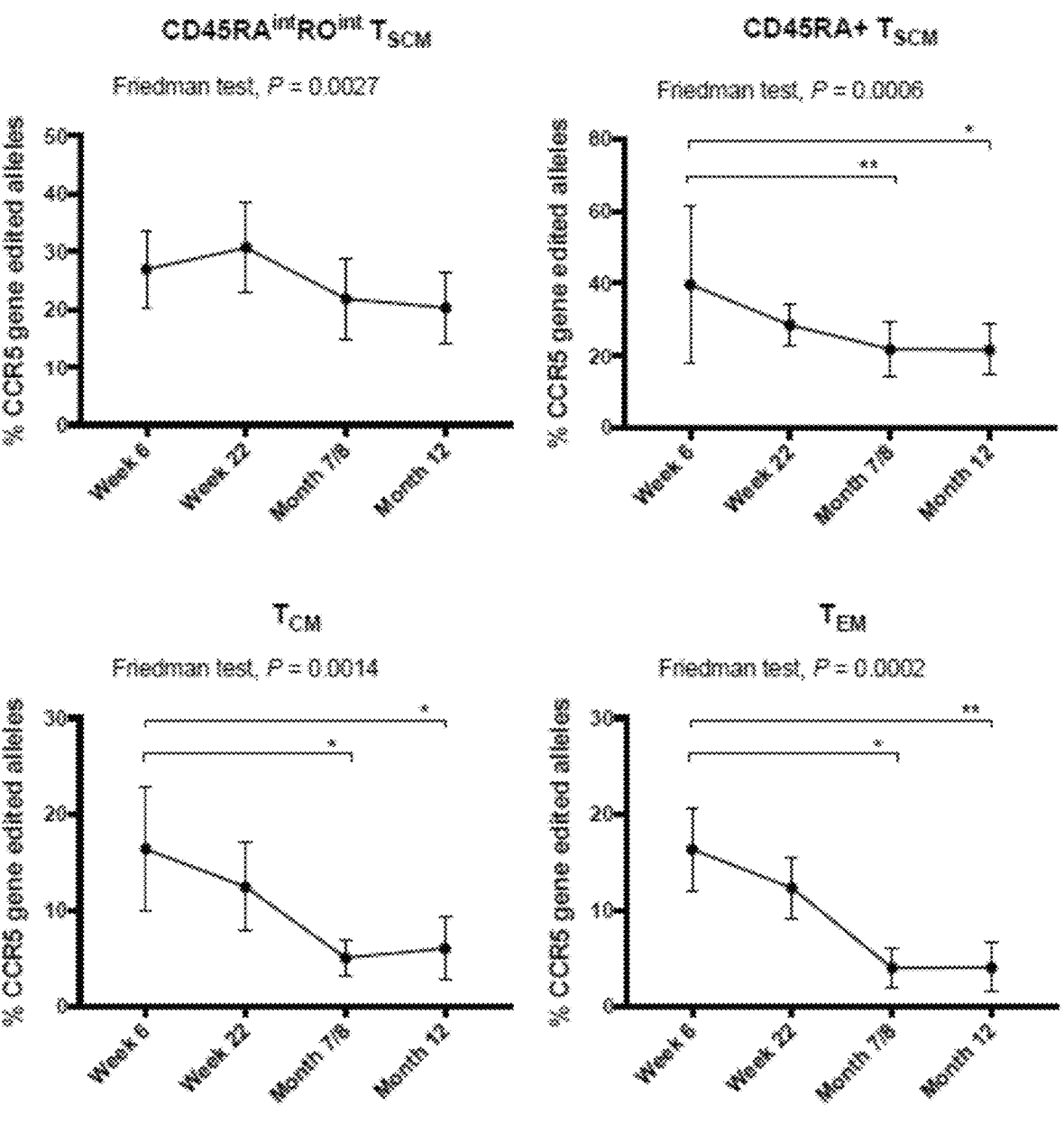

FIG. 17 illustrates Frequencies of CCR5 gene edited cells in CD4+ T cell subsets post ATI in the 1101 study. The frequency of CCR5 gene edited alleles, determined by DNA sequencing, is shown for CD4+ T cell subsets (CD45RA$^+$ T$_{SCM}$, CD45RA$^{int}$RO$^{int}$ T$_{SCM}$, T$_{CM}$, and T$_{EM}$) at week 6 (pre-ATI), week 22, month 7/8, and month 12 post infusion (during ATI) for participants who had extended ATI until at least month 12.

DETAILED DESCRIPTION

Unless defined otherwise, all technical and scientific terms used herein have the same meaning as commonly understood by one of ordinary skill in the art to which this invention belongs.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

"Activation", as used herein, refers to the state of a T cell that has been sufficiently stimulated to induce detectable cellular proliferation. Activation can also be associated with induced cytokine production, and detectable effector functions. The term "activated T cells" refers to, among other things, T cells that are undergoing cell division.

The term "antibody" as used herein, refers to an immunoglobulin molecule, which is able to specifically bind to a specific epitope on an antigen. Antibodies can be intact immunoglobulins derived from natural sources or from recombinant sources and can be immunoactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)2, as well as single chain antibodies and humanized antibodies (Harlow et al., 1988; Houston et al., 1988; Bird et al., 1988).

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

As used herein, the term "autologous" is meant to refer to any material derived from the same individual to which it is later to be re-introduced into the individual.

"Allogeneic" refers to a graft derived from a different animal of the same species.

"Xenogeneic" refers to a graft derived from an animal of a different species.

An "effective amount" as used herein, means an amount which provides a therapeutic or prophylactic benefit.

The term "expression" as used herein is defined as the transcription and/or translation of a particular nucleotide sequence driven by its promoter.

The term "specifically binds," as used herein, is meant a molecule, such as an antibody, which recognizes and binds to another molecule or feature, but does not substantially recognize or bind other molecules or features in a sample.

The term "inhibit," as used herein, means to reduce a molecule, a reaction, an interaction, a gene, an mRNA, and/or a protein's expression, stability, function or activity by a measurable amount or to prevent entirely. Inhibitors are compounds that, e.g., bind to, partially or totally block stimulation, decrease, prevent, delay activation, inactivate, desensitize, or down regulate a protein, a gene, and an mRNA stability, expression, function and activity, e.g., antagonists.

The terms "nucleic acid." "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of corresponding naturally-occurring amino acids.

"Binding" refers to a sequence-specific, non-covalent interaction between macromolecules (e.g., between a protein and a nucleic acid or between two nucleic acids). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$.

The terms "chimeric RNA", "chimeric guide RNA", "guide RNA", "single guide RNA" and "synthetic guide RNA" are used interchangeably and refer to the polynucleotide sequence comprising the guide sequence, the tracr sequence and the tracr mate sequence. The term "guide sequence" refers to the about 10-30 (10, 11, 12, 13, 14, 15, 16, 17, 18, 19, 20, 21, 22, 23, 24, 25, 26, 27, 28, 29, 30) base pair sequence within the guide RNA that specifies the target site and may be used interchangeably with the terms "guide" or "spacer". The term "tracr mate sequence" may also be used interchangeably with the term "direct repeat(s)".

"Complementarity" refers to the ability of a nucleic acid to form hydrogen bond(s) with another nucleic acid sequence by either traditional Watson-Crick or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

A "binding protein" is a protein that is able to bind to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

A "TALE DNA binding domain" or "TALE" is a polypeptide comprising one or more TALE repeat domains/units. The repeat domains are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein.

Zinc finger and TALE binding domains can be "engineered" to bind to a predetermined nucleotide sequence, for example via engineering (altering one or more amino acids) of the recognition helix region of a naturally occurring zinc finger or TALE protein. Therefore, engineered DNA binding proteins (zinc fingers or TALEs) are proteins that are non-naturally occurring. Non-limiting examples of methods for engineering DNA-binding proteins are design and selection. A designed DNA binding protein is a protein not occurring in nature whose design/composition results principally from rational criteria. Rational criteria for design include application of substitution rules and computerized algorithms for processing information in a database storing information of existing ZFP and/or TALE designs and binding data. See, for example, U.S. Pat. Nos. 8,586,526 6,140,081; 6,453,242; and 6,534,261; see also WO 98/53058; WO 98/53059; WO 98/53060; WO 02/016536 and WO 03/016496.

A "selected" zinc finger protein or TALE is a protein not found in nature whose production results primarily from an empirical process such as phage display, interaction trap or hybrid selection. See e.g., U.S. Pat. Nos. 8,586,526; 5,789, 538; 5,925,523; 6,007,988; 6,013,453; 6,200,759; as well as WO 95/19431; WO 96/06166; WO 98/53057; WO 98/54311; WO 00/27878; WO 01/60970 WO 01/88197; WO 02/099084.

"Recombination" refers to a process of exchange of genetic information between two polynucleotides. For the purposes of this disclosure, "homologous recombination (HR)" refers to the specialized form of such exchange that takes place, for example, during repair of double-strand breaks in cells via homology-directed repair mechanisms. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to re-synthesize genetic information that will become part of the target, and/or related processes. Such specialized HR often results in an alteration of the sequence of the target molecule such that part or all of the sequence of the donor polynucleotide is incorporated into the target polynucleotide.

In the methods of the disclosure, one or more targeted nucleases (e.g., CRISPR/Cas) as described herein create a double-stranded break in the target sequence (e.g., cellular chromatin) at a predetermined site, and a "donor" polynucleotide, having homology to the nucleotide sequence in the region of the break, can be introduced into the cell. The presence of the double-stranded break has been shown to facilitate integration of the donor sequence. The donor sequence may be physically integrated or, alternatively, the donor polynucleotide is used as a template for repair of the break via homologous recombination, resulting in the introduction of all or part of the nucleotide sequence as in the donor into the cellular chromatin. Thus, a first sequence in cellular chromatin can be altered and, in certain embodiments, can be converted into a sequence present in a donor polynucleotide. Thus, the use of the terms "replace" or "replacement" can be understood to represent replacement of one nucleotide sequence by another, (i.e., replacement of a sequence in the informational sense), and does not necessarily require physical or chemical replacement of one polynucleotide by another.

In any of the methods described herein, additional CRISPR/Cas nucleases and/or additional pairs of zinc-finger or TALEN proteins can be used for additional double-stranded cleavage of additional target sites within the cell.

In certain embodiments of methods for targeted recombination and/or replacement and/or alteration of a sequence in a region of interest in cellular chromatin, a chromosomal sequence is altered by homologous recombination with an exogenous "donor" nucleotide sequence. Such homologous recombination is stimulated by the presence of a double-stranded break in cellular chromatin, if sequences homologous to the region of the break are present.

In any of the methods described herein, the exogenous nucleotide sequence (the "donor sequence" or "transgene") can contain sequences that are homologous, but not identical, to genomic sequences in the region of interest, thereby stimulating homologous recombination to insert a non-identical sequence in the region of interest. Thus, in certain embodiments, portions of the donor sequence that are homologous to sequences in the region of interest exhibit between about 80 to 99% (or any integer therebetween) sequence identity to the genomic sequence that is replaced. In other embodiments, the homology between the donor and genomic sequence is higher than 99%, for example if only 1 nucleotide differs as between donor and genomic sequences of over 100 contiguous base pairs. In certain cases, a non-homologous portion of the donor sequence can contain sequences not present in the region of interest, such that new sequences are introduced into the region of interest. In these instances, the non-homologous sequence is generally flanked by sequences of 50-1,000 base pairs (or any integral value therebetween) or any number of base pairs greater than 1,000, that are homologous or identical to sequences in the region of interest. In other embodiments, the donor sequence is non-homologous to the first sequence, and is inserted into the genome by non-homologous recombination mechanisms.

Any of the methods described herein can be used for partial or complete inactivation of one or more target sequences in a cell by targeted integration of donor sequence that disrupts expression of the gene(s) of interest. Cell lines with partially or completely inactivated genes are also provided.

Furthermore, the methods of targeted integration as described herein can also be used to integrate one or more exogenous sequences. The exogenous nucleic acid sequence can comprise, for example, one or more genes or cDNA molecules, or any type of coding or non-coding sequence, as well as one or more control elements (e.g., promoters). In addition, the exogenous nucleic acid sequence may produce one or more RNA molecules (e.g., small hairpin RNAs (shRNAs), inhibitory RNAs (RNAis), microRNAs (miR-NAs), etc.).

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage half-domain" is a polypeptide sequence which, in conjunction with a second polypeptide (either identical or different) forms a complex having cleavage activity (preferably double-strand cleavage activity). The terms "first and second cleavage half-domains;" "+ and − cleavage half-domains" and "right and left cleavage half-domains" are used interchangeably to refer to pairs of cleavage half-domains that dimerize.

An "engineered cleavage half-domain" is a cleavage half-domain that has been modified so as to form obligate heterodimers with another cleavage half-domain (e.g., another engineered cleavage half-domain). Sec, also, U.S. Patent Publication Nos. 2005/0064474, 2007/0218528, 2008/0131962 and 2011/0201055, incorporated herein by reference in their entireties.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 10,000 nucleotides in length (or any integer value therebetween or thereabove), preferably between about 100 and 1,000 nucleotides in length (or any integer therebetween), more preferably between about 200 and 500 nucleotides in length.

A "homologous, non-identical sequence" refers to a first sequence which shares a degree of sequence identity with a second sequence, but whose sequence is not identical to that of the second sequence. For example, a polynucleotide comprising the wild-type sequence of a mutant gene is homologous and non-identical to the sequence of the mutant gene. In certain embodiments, the degree of homology between the two sequences is sufficient to allow homologous recombination therebetween, utilizing normal cellular mechanisms. Two homologous non-identical sequences can be any length and their degree of non-homology can be as small as a single nucleotide (e.g., for correction of a genomic point mutation by targeted homologous recombination) or as large as 10 or more kilobases (e.g., for insertion of a gene at a predetermined ectopic site in a chromosome). Two poly-nucleotides comprising the homologous non-identical sequences need not be the same length. For example, an exogenous polynucleotide (i.e., donor polynucleotide) of between 20 and 10,000 nucleotides or nucleotide pairs can be used.

Techniques for determining nucleic acid and amino acid sequence identity are known in the art. Typically, such techniques include determining the nucleotide sequence of the mRNA for a gene and/or determining the amino acid sequence encoded thereby, and comparing these sequences to a second nucleotide or amino acid sequence. Genomic sequences can also be determined and compared in this fashion. In general, identity refers to an exact nucleotide-to-nucleotide or amino acid-to-amino acid correspondence of two polynucleotides or polypeptide sequences, respectively. Two or more sequences (polynucleotide or amino acid) can be compared by determining their percent identity. The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, Advances in Applied Mathematics 2:482-489 (1981). This algorithm can be applied to amino acid sequences by using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov, Nucl. Acids Res. 14 (6): 6745-6763 (1986). An exemplary implementation of this algorithm to determine percent identity of a sequence is provided by the Genetics Computer Group (Madison, Wis.) in the "BestFit" utility application. Suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found on the internet. With respect to sequences described herein, the range of desired degrees of sequence identity is approximately 80% to 100% and any integer value therebetween. Typically the percent identities between sequences are at least 70-75%, preferably 80-82%, more preferably 85-90%, even more preferably 92%, still more preferably 95%, and most preferably 98% sequence identity.

Alternatively, the degree of sequence similarity between polynucleotides can be determined by hybridization of polynucleotides under conditions that allow formation of stable duplexes between homologous regions, followed by digestion with single-stranded-specific nuclease(s), and size determination of the digested fragments. Two nucleic acid, or two polypeptide sequences are substantially homologous to each other when the sequences exhibit at least about 70%-75%, preferably 80%-82%, more preferably 85%-90%, even more preferably 92%, still more preferably 95%, and most preferably 98% sequence identity over a defined length of the molecules, as determined using the methods above. As used herein, substantially homologous also refers to sequences showing complete identity to a specified DNA or polypeptide sequence. DNA sequences that are substantially homologous can be identified in a Southern hybridization experiment under, for example, stringent conditions, as defined for that particular system. Defining appropriate hybridization conditions is known to those with skill of the art. Sec, e.g., Sambrook et al., supra; Nucleic Acid Hybridization: A Practical Approach, editors B. D. Hames and S. J. Higgins, (1985) Oxford; Washington, D.C.; IRL Press).

Selective hybridization of two nucleic acid fragments can be determined as follows. The degree of sequence identity between two nucleic acid molecules affects the efficiency and strength of hybridization events between such molecules. A partially identical nucleic acid sequence will at least partially inhibit the hybridization of a completely identical sequence to a target molecule. Inhibition of hybridization of the completely identical sequence can be assessed using hybridization assays that are well known in the art (e.g., Southern (DNA) blot, Northern (RNA) blot, solution hybridization, or the like, see Sambrook, et al., Molecular Cloning: A Laboratory Manual, Second Edition, (1989) Cold Spring Harbor, N.Y.). Such assays can be conducted using varying degrees of selectivity, for example, using conditions varying from low to high stringency. If conditions of low stringency are employed, the absence of non-specific binding can be assessed using a secondary probe that lacks even a partial degree of sequence identity (for example, a probe having less than about 30% sequence identity with the target molecule), such that, in the absence of non-specific binding events, the secondary probe will not hybridize to the target.

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

An "accessible region" is a site in cellular chromatin in which a target site present in the nucleic acid can be bound by an exogenous molecule which recognizes the target site. Without wishing to be bound by any particular theory, it is believed that an accessible region is one that is not packaged into a nucleosomal structure. The distinct structure of an accessible region can often be detected by its sensitivity to chemical and enzymatic probes, for example, nucleases.

A "target site" or "target sequence" is a nucleic acid sequence that defines a portion of a nucleic acid to which a binding molecule will bind, provided sufficient conditions for binding exist.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases. Thus, the term includes "transgenes" or "genes of interest" which are exogenous sequences introduced into a cell.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer. An exogenous molecule can also be the same type of molecule as an endogenous molecule but derived from a different species than the cell is derived from. For example, a human nucleic acid sequence may be introduced into a cell line originally derived from a mouse or hamster. Methods for the introduction of exogenous molecules into plant cells are known to those of skill in the art and include, but are not limited to, protoplast transformation, silicon carbide (e.g., WHISKERS.TM.), Agrobacterium-mediated transformation, lipid-mediated transfer (i.e., liposomes, including neutral and cationic lipids), electroporation, direct injection, cell fusion, particle bombardment (e.g., using a "gene gun"), calcium phosphate co-precipitation, DEAE-dextran-mediated transfer and viral vector-mediated transfer.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

As used herein, the term "product of an exogenous nucleic acid" includes both polynucleotide and polypeptide products, for example, transcription products (polynucleotides such as RNA) and translation products (polypeptides).

A "fusion" molecule is a molecule in which two or more subunit molecules are linked, preferably covalently. The subunit molecules can be the same chemical type of molecule, or can be different chemical types of molecules. Examples of the first type of fusion molecule include, but are not limited to, fusion proteins (for example, a fusion between a ZFP or TALE DNA-binding domain and one or more activation domains) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid. A "fusion polypeptide" is a polypeptide comprising a polypeptide or portion (e.g., one or more domains) thereof fused or bonded to heterologous polypeptide. Examples of fusion polypeptides include immunoadhesins which combine a portion of the Cas protein with an immunoglobulin sequence, and epitope tagged polypeptides, which may comprise a Cas protein, for example, or portion thereof fused to a "tag polypeptide". The tag polypeptide has enough residues to provide an epitope against which an antibody can be made, yet is short enough such that it does not interfere with nuclease activity of Cas. Suitable tag polypeptides generally have at least six amino acid residues and usually between about 6-60 amino acid residues.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "gene." for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions. An "engineered gene" refers to a gene which has been altered in some manner such that it is non-identical with a wild type gene. Alterations can be in the form of targeted deletions, insertions and truncations. An engineered gene can comprise coding sequences from two heterologous genes or may comprise synthetic gene sequences. An engineered gene may also comprise changes in the coding sequence that are silent in the protein sequence (e.g., codon optimization). An engineered gene can also comprise a gene with altered regulatory sequences.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the activity of a gene. Modulation of expression can include, but is not limited to, gene activation and gene repression. Genome editing (e.g., cleavage, alteration, inactivation, random mutation) can be used to modulate expression. Gene inactivation refers to any reduction in gene expression as compared to a cell that does not include a CRISPR/Cas system as described herein. Thus, gene inactivation may be partial or complete.

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

"Eukaryotic" cells include, but are not limited to, fungal cells (such as yeast), plant cells, animal cells, mammalian cells and human cells (e.g., T-cells).

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a Cas DNA-binding domain is fused to an activation domain, the Cas DNA-binding domain and the activation domain are in operative linkage if, in the fusion polypeptide, the Cas DNA-binding domain portion is able to bind its target site and/or its binding site, while the activation domain is able to up-regulate gene expression. When a fusion polypeptide in which a Cas DNA-binding domain is fused to a cleavage domain, the Cas DNA-binding domain and the cleavage domain are in operative linkage if, in the fusion polypeptide, the Cas DNA-binding domain portion is able to bind its target site and/or its binding site, while the cleavage domain is able to cleave DNA in the vicinity of the target site.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one or more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. The ability of a protein to interact with another protein can be determined, for example, by co-immunoprecipitation, two-hybrid assays or complementation, both genetic and biochemical. See, for example, Fields et al. (1989) Nature 340:245-246; U.S. Pat. No. 5,585,245 and PCT WO 98/44350.

A "vector" is capable of transferring gene sequences to target cells. Typically, "vector construct," "expression vector," and "gene transfer vector," mean any nucleic acid construct capable of directing the expression of a gene of interest and which can transfer gene sequences to target cells. Thus, the term includes cloning, and expression vehicles, as well as integrating vectors.

A "reporter gene" or "reporter sequence" refers to any sequence that produces a protein product that is easily measured, preferably although not necessarily in a routine assay. Suitable reporter genes include, but are not limited to, sequences encoding proteins that mediate antibiotic resistance (e.g., ampicillin resistance, neomycin resistance, G418 resistance, puromycin resistance), sequences encoding colored or fluorescent or luminescent proteins (e.g., green fluorescent protein, enhanced green fluorescent protein, red fluorescent protein, luciferase), and proteins which mediate enhanced cell growth and/or gene amplification (e.g., dihydrofolate reductase). Epitope tags include, for example, one or more copies of FLAG, His, myc, Tap, HA or any detectable amino acid sequence. "Expression tags" include sequences that encode reporters that may be operably linked to a desired gene sequence in order to monitor expression of the gene of interest.

The terms "subject" and "patient" are used interchangeably and refer to mammals such as human patients and non-human primates, as well as experimental animals such as rabbits, dogs, cats, rats, mice, and other animals. Accordingly, the term "subject" or "patient" as used herein means any mammalian patient or subject to which the or stem cells of the invention can be administered. Subjects of the present invention include those that have been exposed to one or more chemical toxins, including, for example, a nerve toxin.

The term "therapeutic" as used herein means a treatment and/or prophylaxis. A therapeutic effect is obtained by suppression, remission, or eradication of a disease state.

The term "therapeutically effective amount" refers to the amount of the subject compound that will elicit the biological or medical response of a tissue, system, or subject that is being sought by the researcher, veterinarian, medical doctor or other clinician. The term "therapeutically effective amount" includes that amount of a compound that, when administered, is sufficient to prevent development of, or alleviate to some extent, one or more of the signs or symptoms of the disorder or disease being treated. The therapeutically effective amount will vary depending on the compound, the disease and its severity and the age, weight, etc., of the subject to be treated. To "treat" a disease as the term is used herein, means to reduce the frequency or severity of at least one sign or symptom of a disease or disorder experienced by a subject.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Embodiments described herein relate to a long-lived enriched population of CD4 T cells and CD 8 T cells (CD4/CD8 T cells) having a CD45RA$^{int}$CD45RO$^{int}$ phenotype, genetically modified and/or altered CD4/CD8 T cells having a CD45RA$^{int}$CD45RO$^{int}$ phenotype, and to their use in treating an HIV infected subject and particularly a latent HIV infection of a subject that has undergone and/or continues to undergo antiretroviral therapy. It was found that a subset CD4/CD8 T cells has phenotypic and molecular attributes of long-lived pluripotent stem cells. Like other known stem cell populations, this subset population has a low metabolic profile (upregulation of fatty acid metabolism and oxidative phosphorylation, and down regulation of cell cycling pathways) retains the capacity to self-renew, and can differentiate to effector cells. This subset is primarily characterized by intermediate co-expression of CD45RA and CD45RO (CD45RA$^{int}$CD45RO$^{int}$). CD4/CD8 T cells having a CD45RA$^{int}$CD45RO$^{int}$ phenotype can also express CD95 (Fas) CD127 (IL7R) and CD27. Addition of low doses of cytokines IL-7 and IL-15 can lead to the formation of an enriched population of CD4/CD8 cells having the CD45RA$^{int}$CD45RO$^{int}$ phenotype; while high doses of cytokines IL-7 and IL-15 can lead to effector differentiation of the cells.

In some embodiments, CD4/CD8 T cells having a CD45RA$^{int}$CD45RO$^{int}$ phenotype can be genetically modified such that they are devoid of a functional CCR5 and/or CXCR4 HIV co-receptor. Administration of CCR5 and/or CXCR4 gene edited autologous CD4/CD8 T cells having a CD45RA$^{int}$CD45RO$^{int}$ phenotype to an HIV infected subject can provide sustained increases in CD4+ T cell counts, restored T cell homeostasis, and a substantial decline in the size of the HIV reservoir in the subject.

The enriched population CCR5 and/or CXCR4 gene edited CD4/CD8 T cells having a CD45RA$^{int}$CD45RO$^{int}$ phenotype upon transplantation or administration to a subject have the ability to persist or survive long term in the subject. The persistence can correlate with the efficacy of a therapeutic T cell transplant in the treatment of a disease, such as an HIV infection. The greater the persistence of therapeutic T cells, the more likely a therapeutic regime is to be effective. Thus, long-lived, self-renewing and pluripotent CCR5 and/or CXCR4 gene edited CD4/CD8 T cells having a CD45RA$^{int}$CD45RO$^{int}$ phenotype can have a reduced cost of production, promote effector differentiation, and increase efficiency of treating latent HIV infection in a subject. Moreover, frequencies of these cells in the currently available HIV therapy products can be used as a biomarker and be predictive of successful intervention.

In some embodiment, the enriched population CCR5 and/or CXCR4 gene edited CD4/CD8 T cells having a CD45RA$^{int}$CD45RO$^{int}$ phenotype can persist in vivo for at least 1, 2, 3, 4, 5, 6, 12, 24, 36, 48 or 72 months longer than T cells without the CD45RA$^{int}$CD45RO$^{int}$ phenotype after administration to a subject. The enriched population CCR5 and/or CXCR4 gene edited CD4/CD8 T cells having the CD45RA (CD45RO$^{int}$ phenotype can also possess an increased ability to engraft in a subject after administration. In particular, the enriched population CCR5 and/or CXCR4 gene edited CD4/CD8 T cells having the CD45RA$^{int}$CD45RO$^{int}$ phenotype can possess an increased ability to engraft in a non-conditioned recipient.

The term "engraftment" refers to the ability of the transplanted cells to populate a recipient and survive in the immediate aftermath of their transplantation. Accordingly, engraftment is assessed in the short term after transplantation. For example, engraftment may refer to the number of cells descended from the transplanted cells that are detected in the first in vivo evaluation of an experiment, clinical trial or therapeutic protocol, e.g., at the earliest time point that transplanted cells or their descendants may be detected in a recipient. In one embodiment, engraftment is assessed at 0-12, 0-24, 0-48 or 0-72 h after transplantation. In another embodiment, engraftment is assessed at about 1, 2, 3, 4, 5, 6, 12, 24, 36, 48, 60 or 72 h after transplantation. In a preferred embodiment, engraftment is assessed at about 12 h after transplantation.

FIG. 1 illustrates a flow diagram illustrating a method of generating an enriched population of CD4/CD8 T cells having a CD45RA$^{int}$CD45RO$^{int}$ phenotype, which can be genetically modified such that they are devoid of a functional CCR5 and/or CXCR4 HIV co-receptor. In the method, at step 10, a naïve population of T-cells is isolated from a biological sample of a subject. The biological sample can include any T cell containing sample from the subject. Examples of subjects include humans, dogs, cats, mice, rats, and transgenic species thereof. Preferably, the subject is a human.

T cells can be obtained from a number of sources, including peripheral blood mononuclear cells, bone marrow, lymph node tissue, spleen tissue, and tumors. In some embodiments, the T cells can be obtained from a subject having HIV to be treated, i.e., autologous T-cells from the subject to be treated. In certain embodiments, T cells can be obtained from a unit of blood collected from a subject using any number of techniques known to the skilled artisan, such as ficoll separation. In some embodiments, cells from the circulating blood of an individual are obtained by apheresis or leukapheresis. The apheresis product typically contains lymphocytes, including T cells, monocytes, granulocytes, B cells, other nucleated white blood cells, red blood cells, and platelets. The cells collected by apheresis may be washed to remove the plasma fraction and to place the cells in an appropriate buffer or media for subsequent processing steps. In one embodiment, the cells can be washed with phosphate buffered saline (PBS). In an alternative embodiment, the wash solution lacks calcium and may lack magnesium or may lack many or all divalent cations. After washing, the cells may be resuspended in a variety of biocompatible buffers, such as, for example, Ca-free, Mg-free PBS. Alternatively, the undesirable components of the apheresis sample may be removed and the cells directly resuspended in culture media.

In another embodiment, T cells can be isolated from peripheral blood by lysing the red blood cells and depleting the monocytes, for example, by centrifugation through a PERCOLL gradient. Alternatively, T cells can be isolated from umbilical cord. In any event, a specific subpopulation of T cells can be further isolated by positive or negative selection techniques.

In some embodiments, the isolated T cells can include CD4+ T cells and/or CD8+ T cells. CD4 T cells and/or CD8

T cells (CD4/CD8 T cells) can be isolated from the biological sample by positive or negative selection. Negative selection can be accomplished using a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion.

Following isolation of the T cells from the biological sample, at step 20, the isolated CD4/CD8 T cells can be activated and/or expanded by any suitable method known in the art. In an embodiment of the invention, the T cells are activated and the numbers of T cells are expanded in the presence of one or more non-specific T cell stimuli (e.g., anti-CD3 and anti-CD28) and/or one or more cytokines, cytokines (e.g., IL-1b, IL-2, IL-4, IL-6, IL-7, IL-9, IL-10, IL-12, IL-15, IL-17, IL-21, IL-22, IL-23, IL-35, TGF-β, IFNα, IFNγ, TNFα) recombinant proteins, costimulatory molecules, lectins, ionophores, synthetic molecules, antigen presenting cells (APCs), artificial APCs or feeders. In some embodiments, the CD4/CD8 T cells can activated and the numbers of T cells are expanded by physically contacting the T cells with one or more non-specific T cell stimuli and/or one or more cytokines. Any one or more non-specific T cell stimuli may be used in the inventive methods. Examples of non-specific T cell stimuli include anti-CD3 antibodies and anti-CD28 antibodies. In some embodiments, the non-specific T cell stimulus may be anti-CD3 antibodies and anti-CD28 antibodies conjugated to beads. Any one or more cytokines may be used in the inventive methods. Exemplary cytokines include interleukin (IL)-2, IL-7, IL-21, and IL-15.

Following activation and/or expansion of the isolated CD4/CD8 T cells, at step 30, the CD4/CD8 T cells can be separated or sorted using, for example, flow cytometry, into an enriched population of CD4/CD8 T cells characterized by intermediate co-expression of CD45RA and CD45RO (CD45RA$^{int}$CD45RO$^{int}$). The method may comprise sorting the cells in any suitable manner. In some embodiments, the sorting is carried out using flow cytometry. The flow cytometry may be carried out using any suitable method known in the art. The flow cytometry may employ any suitable antibodies and stains. In some embodiments, the flow cytometry is polychromatic flow cytometry.

The enriched population of CD4/C8 T cells having a CD45RA$^{int}$CD45RO$^{int}$ phenotype produced by the processes described herein can include CD4/C8 T cells having a CD45RA$^{int}$CD45RO$^{int}$ as the majority cell type. In some embodiments, the processes described herein produce cell cultures and/or cell populations comprising at least about 99%, at least about 98%, at least about 97%, at least about 96%, at least about 95%, at least about 94%, at least about 93%, at least about 92%, at least about 91%, at least about 90%, at least about 89%, at least about 88%, at least about 87%, at least about 86%, at least about 85%, at least about 84%, at least about 83%, at least about 82%, at least about 81%, at least about 80%, at least about 79%, at least about 78%, at least about 77%, at least about 76%, at least about 75%, at least about 74%, at least about 73%, at least about 72%, at least about 71%, at least about 70%, at least about 69%, at least about 68%, at least about 67%, at least about 66%, at least about 65%, at least about 64%, at least about 63%, at least about 62%, at least about 61%, at least about 60%, at least about 59%, at least about 58%, at least about 57%, at least about 56%, at least about 55%, at least about 54%, at least about 53%, at least about 52%, at least about 51% or at least about 50% CD4/C8 T cells having a CD45RA$^{int}$CD45RO$^{int}$. In preferred embodiments, the cells of the cell cultures or cell populations comprise human cells.

The long lived CD4/CD8 T cells having a CD45RA$^{int}$CD45RO$^{int}$ phenotype can also be characterized by the expression of other cell surface markers. For example, the separated CD4/CD8 T cells having a CD45RA$^{int}$CD45RO$^{int}$ phenotype can express at least one of CD95, CD127, or CD27. In other embodiments, the CD4/CD8 T cells having a CD45RA$^{int}$CD45RO$^{int}$ phenotype can further intermediately express 4-1BB and optionally express OX40.

In other embodiments, the separated CD4/CD8 T-cells having a CD45RA$^{int}$CD45RO$^{int}$ phenotype can further express at least one of, at least two of, at least three of, at least four of, at least five of or more of IL17RA, CD5, IL2RG, IGF2R, SLC38A1, IL7R, SLC44A2, SLC2A3, CD96, CD44, CD6, CCR4, IL4R, or SLC12A7.

In some embodiments, the separated CD4/CD8 T cells can have a CD45RA$^{int}$CD45RO$^{int}$CD95+CD127+CD27+ phenotype. In other embodiments, the separated T-cells can have a CD45RA$^{int}$CD45RO$^{int}$CD95+CD127+CD27+IL7R+ CD44+ SCL38A1+IL2RG+CD6+CD5+ phenotype.

In some embodiments, prior to and/or after separation or sorting of the CD4/C8 T cells having a CD45RA$^{int}$CD45RO$^{int}$ phenotype, the isolated CD4-CD8 T cells having the CD45RA$^{int}$CD45RO$^{int}$ phenotype can be enriched by culturing the isolated CD4/CD8 T cells in a culture medium that includes low amount of IL-7 and/or IL-15. It was found that activated CD4/CD8 T cells cultured in low IL-7/IL-15 conditions (e.g., concentration of IL7/IL15 less than 10 ng/ml) can promote or form an enriched population of the CD4/C8 T cells having a CD45RA$^{int}$CD45RO$^{int}$ phenotype compared to activated CD4/CD8 T cells cultured in high IL-7/IL-15 conditions (e.g., concentration of IL-7/IL-15 greater than 10 ng/ml).

In some embodiments, the culture medium can include IL-7 and/or IL-15 at a concentration, for example, of less than about 100 ng/ml, less than about 95 ng/ml, less than about 90 ng/ml, less than about 85 ng/ml, less than about 80 ng/ml, less than about 75 ng/ml, less than about 70 ng/ml, less than about 65 ng/ml, less than about 60 ng/ml, less than about 55 ng/ml, less than about 50 ng/ml, less than about 45 ng/ml, less than about 40 ng/ml, less than about 35 ng/ml, less than about 30 ng/ml, less than about 25 ng/ml, less than about 20 ng/ml, less than about 15 ng/ml, less than about 10 ng/ml, less than about 5 ng/ml, less than about 4 ng/ml, less than about 3 ng/ml, less than about 2 ng/ml, or less than about 1 ng/ml.

Using the low IL-7/IL-15 concentration culture medium described herein, cell populations or cell cultures can be enriched in CD4/C8 T cells having a CD45RA CD45RO$^{int}$ phenotype content by at least about 2- to about 1000-fold as compared to untreated cell populations or cell cultures. In some embodiments, CD4/C8 T cells having a CD45RA$^{int}$CD45RO$^{int}$ phenotype can be enriched by at least about 5- to about 500-fold as compared to untreated cell populations or cell cultures. In other embodiments, CD4/C8 T cells having a CD45RA$^{int}$CD45RO$^{int}$ phenotype can be enriched from at least about 10- to about 200-fold as compared to untreated cell populations or cell cultures. In still other embodiments, CD4/C8 T cells having a CD45RA$^{int}$CD45RO$^{int}$ phenotype can be enriched from at least about 20- to about 100-fold as compared to untreated cell populations or cell cultures. In yet other embodiments, CD4/C8 T cells having a CD45RA$^{int}$CD45RO$^{int}$ phenotype can be enriched from at least about 40- to about 80-fold as compared to untreated cell populations or cell cultures. In certain embodiments, CD4/C8 T cells having a CD45RA$^{int}$CD45RO$^{int}$ phenotype can be enriched from at least about 2- to about 20-fold as compared to untreated cell populations or cell cultures.

In some embodiments, once separated or sorted, the CD4/CD8 T-cells can be cultured in a culture medium comprising TGFβ/IL1β to maintain the CD45RA$^{int}$CD45RO$^{int}$ phenotype. The addition of TGFβ and/or IL1β to the CD4/CD8 cells having a CD45RA$^{int}$CD45RO$^{int}$ phenotype can lead to the maintenance of the CD45RA$^{int}$CD45RO$^{int}$ phenotype prior to administration to a subject.

In some embodiments, the method can further include genetically modifying the CD4/CD8 T cells prior to or after activation and/or separation such that they are devoid of a functional CCR5 and/or CXCR4 HIV co-receptor. When HIV infects human T cells, it relies on association with the T cell receptor CD4 and one of two co-receptors, the chemokine receptor CCR5 or CXCR4, to gain entry into the cell. Natural CCR5 variants ("CCR5-Δ32") in the human population were identified who appear to be resistant to HIV infection, especially in the homozygous state. Thus, to prevent HIV from infecting T cells, and ultimately leading to T cell death and decreased immune function in the HIV infected patient, disruption of one or both of the co-receptors may be accomplished to render the cell resistant to the virus (see U.S. Pat. No. 7,951,925). Currently clinical trials are underway where HIV patient T cells are edited at the CCR5 locus ex vivo to knock out the CCR5 gene. These cells are then re-introduced into the patient to treat HIV.

In some embodiments, the CD4/CD8 T cells can be genetically modified such that the CD4/CD8 T cells are devoid of a functional CCR5 and/or CXCR4 HIV co-receptor before separating the population of CD4/CD8 T cells having the CD45RA$^{int}$CD45RO$^{int}$ phenotype from the isolated T-cells. In other embodiments, the population of CD4/CD8 T cells having the CD45RA$^{int}$CD45RO$^{int}$ phenotype can be genetically modified after separation from the isolated T-cells such that the population of CD4/CD8 T cells having the CD45RA$^{int}$CD45RO$^{int}$ phenotype are devoid of a functional CCR5 and/or CXCR4 HIV co-receptor.

In some embodiments, the genetic modification or genome editing of the CD4/CD8 T cells may be performed by transduction, transfection or electroporation. Transduction can performed with lentiviruses, gamma-, alpha-retroviruses or adenoviruses or with electroporation or transfection by nucleic acids (DNA, mRNA, miRNA, antagomirs, ODNs), proteins, site-specific nucleases (zinc finger nucleases, TALENs, CRISP/R), self replicating RNA viruses (e.g., equine encephalopathy virus) or integration-deficient lentiviral vectors.

In some embodiments, the CD4/CD8 T cells and/or the CD4/CD8 T cells having the CD45RA$^{int}$CD45RO$^{int}$ phenotype can be genetically modified by genome editing with engineered nucleases. Genome editing is a process of inserting, deleting, or modifying genomic sequences using sequence-specific nucleases. Several methods of genome editing currently exist, including meganucleases, zin-finger nucleases (ZFNs), transcription activator-like effector-based nucleases (TALENs), and the CRISPR-Cas system. These nucleases induce double-stranded DNA breaks that can subsequently be repaired by either non-homologous end joining (NHEJ) or homology dependent repair (HDR), which allows for insertion or modification of a gene using a template with homology to the DNA surrounding the double-stranded break. Traditionally, genome editing has been performed by transfecting or transducing cells with RNA or DNA that then produce the proteins and, in the case of the CRISPR-Cas system, the guide RNAs, required for genome editing.

For example, a double-strand break (DSB) for can be created by a site-specific nuclease such as a zinc-finger nuclease (ZFN) or TAL effector domain nuclease (TALEN). See, for example, Urnov et al. (2010) Nature 435 (7042): 646-51; U.S. Pat. Nos. 8,586,526; 6,534,261; 6,599,692; 6,503,717; 6,689,558; 7,067,317; 7,262,054, the disclosures of which are incorporated by reference in their entireties for all purposes.

Another nuclease system involves the use of a so-called acquired immunity system found in bacteria and archaca known as the CRISPR/Cas system. CRISPR/Cas systems are found in 40% of bacteria and 90% of archaca and differ in the complexities of their systems. See, e.g., U.S. Pat. No. 8,697,359. The CRISPR loci (clustered regularly interspaced short palindromic repeat) is a region within the organism's genome where short segments of foreign DNA are integrated between short repeat palindromic sequences. These loci are transcribed and the RNA transcripts ("pre-crRNA") are processed into short CRISPR RNAs (crRNAs). There are three types of CRISPR/Cas systems which all incorporate these RNAs and proteins known as "Cas" proteins (CRISPR associated). Types I and III both have Cas endonucleases that process the pre-crRNAs, that, when fully processed into crRNAs, assemble a multi-Cas protein complex that is capable of cleaving nucleic acids that are complementary to the crRNA.

In type II systems, crRNAs are produced using a different mechanism where a trans-activating RNA (tracrRNA) complementary to repeat sequences in the pre-crRNA. triggers processing by a double strand-specific RNase III in the presence of the Cas9 protein. Cas9 is then able to cleave a target DNA that is complementary to the mature crRNA however cleavage by Cas 9 is dependent both upon base-pairing between the crRNA and the target DNA, and on the presence of a short motif in the crRNA referred to as the PAM sequence (protospacer adjacent motif). In addition, the tracrRNA must also be present as it base pairs with the crRNA at its 3' end, and this association triggers Cas9 activity.

The Cas9 protein has at least two nuclease domains: one nuclease domain is similar to a HNH endonuclease, while the other resembles a Ruv endonuclease domain. The HNH-type domain appears to be responsible for cleaving the DNA strand that is complementary to the crRNA while the Ruv domain cleaves the non-complementary strand.

The requirement of the crRNA-tracrRNA complex can be avoided by use of an engineered "single-guide RNA" (sgRNA) that comprises the hairpin normally formed by the annealing of the crRNA and the tracrRNA (see Jinek et al (2012) Science 337:816 and Cong et al (2013) Sciencexpress/10.1126/science.1231143). In S. pyrogenes, the engineered tracrRNA: crRNA fusion, or the sgRNA, guides Cas9 to cleave the target DNA when a double strand RNA: DNA heterodimer forms between the Cas associated RNAs and the target DNA. This system comprising the Cas9 protein and an engineered sgRNA containing a PAM sequence has been used for RNA guided genome editing (see Ramalingam ibid) and has been useful for zebrafish embryo genomic editing in vivo (see Hwang et al (2013) Nature Biotechnology 31 (3): 227) with editing efficiencies similar to ZFNs and TALENs.

Specific nucleases can also be engineered to insert a peptide fusion inhibitor on to an HIV receptor to prevent HIV infection of T cells (see co-owned US patent publication no. 20120093787), where an example of such a peptide fusion inhibitor is C34 or fuzcon. Similarly HIV can be treated by using engineered nucleases to insert anti-HIV transgenes in safe harbor loci within the cell to combat the virus. Examples of such anti-HIV genes may be selected from the group consisting of a sequence encoding a zinc finger transcription factor that represses an HIV polyprotein, a sequence encoding a zinc finger transcription factor that represses expression of an HIV receptor, a CCR5 ribozyme, an siRNA sequence targeted to an HIV polyprotein, a sequence encoding a Trim5alpha restriction factor, a sequence encoding an APOBEC3G restriction factor, a sequence encoding a RevM10 protein, a sequence encoding C46, other anti-HIV genes, a suicide cassette and combinations thereof. Thus, the methods and compositions of the invention may be used to treat or prevent HIV with a CRISPR/Cas system where the single guide RNA comprises sequences to target the CCR5 or CXCR4 gene for integration of a suitable anti-HIV transgene.

In some embodiments, the genome editing can include cleavage with site-specific nucleases for targeted insertion into a chosen genomic locus (see, e.g., co-owned U.S. Pat. No. 7,888,121). Nucleases specific for targeted genes can be utilized such that the transgene construct is inserted by either homology directed repair (HDR) or by end capture during non-homologous end joining (NHEJ) driven processes. Targeted loci include "safe harbor" loci such as the AAVS1, HPRT and CCR5 genes in human cells, and Rosa26 in murine cells (see, e.g., U.S. Pat. Nos. 7,888,121; 7,972,854; 7,914,796; 7,951,925; 8,110,379; 8,409,861; 8,586,526; U.S. Patent Publications 20030232410; 20050208489; 20050026157; 20060063231; 20080159996; 201000218264; 20120017290; 20110265198; 20130137104; 20130122591; 20130177983 and 20130177960). Nuclease-mediated integration offers the prospect of improved transgene expression, increased safety and expressional durability, as compared to classic integration approaches that rely on random integration of the transgene, since it allows exact transgene positioning for a minimal risk of gene silencing or activation of nearby oncogenes.

Genome editing can also include the knocking out of genes in addition to insertion methods described above. In the absence of a donor nucleic acid, a cell with a cleaved genome will resort to the error prone NHEJ pathway to heal the break. This process often adds or deletes nucleotides during the repair process ("indels") which may lead to the introduction of missense or non-sense mutations at the target site.

For example, CCR5-specific zinc finger nucleases are being used in Phase I/II trials to create a non-functional CCR5 receptor in T-cells, and thus prevent HIV infection (see U.S. Pat. No. 7,951,925). These cells are then re-introduced into the patient to treat HIV. Thus, the methods and compositions of the invention may be used to disrupt CCR5 alleles with a CRISPR/Cas system where the single guide RNA comprises sequences to target a human CCR5 gene (chr3: 46411633-46417697), especially at or near the exon region (chr3: 46414394-46415452).

One especially preferred region for targeting the CCR5 gene for knock out is the region near the delta-32 mutation region (at or near chr3: 46414923-46415020). Another especially preferred region is around the chr3: 46414522-46414643, which encodes part of the second extracellular loop of the CCR5 protein. The region at or near the ATG protein translation initiation site (at or near chr3: 46414347-46414466) is also especially preferred for genome modification, such as fusion of a C34 peptide to the N-terminus of CCR5 by targeted integration for anti-HIV therapy.

Similar studies are in progress in animal models of CXCR4-dependent HIV where the CXCR4 is selectively disrupted, or disrupted in tandem with CCR5 to prevent HIV infection of T cells (see U.S. Patent Publication No. 20100291048). Thus, the methods and compositions described herein may be used to disrupt CXCR4 alleles with a CRISPR/Cas system where the single guide RNA comprises sequences to target a human CXCR4 gene (chr2: 136871919-136875725), especially at or near the exon 2 region (chr2: 136872439-136873482) and the region surrounding the small exon1 (chr2: 136875616-136875630). One preferred region for targeting the CXCR4 gene for knock out is the region at or near chr2: 136872863-136872982 that is an analog to the delta-32 mutation region in CCR5 gene. The region at or near chr2: 136875540-136875687 near the ATG protein translation initiation site of exon1 is especially preferred, and the region at or near chr2: 136873389-136873558 near the splicing site of exon2 is especially preferred for gene modification, such as fusion of a C34 peptide to the N-terminus of CXCR4 by targeted integration for anti-HIV therapy. Thus, a sgRNA can be designed to bind to sequences anywhere in the CCR5 or CXCR4 locus, including, but not limited to, a sequence in one or more of these preferred targeting regions.

The nucleases, polynucleotides encoding these nucleases, donor polynucleotides and compositions comprising the proteins and/or polynucleotides described herein may be delivered ex vivo to the CD4/CD8 T cells and/or CD4/CD8 T cells having a CD45RA$^{int}$CD45RO$^{int}$ phenotype by any suitable means.

Methods of delivering nucleases as described herein are described, for example, in U.S. Pat. Nos. 6,453,242; 6,503, 717; 6,534,261; 6,599,692; 6,607,882; 6,689,558; 6,824, 978; 6,933,113; 6,979,539; 7,013,219; and 7,163,824, the disclosures of all of which are incorporated by reference herein in their entireties.

Nucleases and/or donor constructs as described herein may also be delivered using vectors containing sequences encoding one or more of the CRISPR/Cas system(s). Any vector systems may be used including, but not limited to, plasmid vectors, DNA minicircles, retroviral vectors, lentiviral vectors, adenovirus vectors, poxvirus vectors; herpesvirus vectors and adeno-associated virus vectors, etc., and combinations thereof. Sec, also, U.S. Pat. Nos. 6,534,261; 6,607,882; 6,824,978; 6,933,113; 6,979,539; 7,013,219; and 7,163,824, and U.S. Publication No. 20140335063, incorporated by reference herein in their entireties. Furthermore, it will be apparent that any of these vectors may comprise one or more of the sequences needed for treatment. Thus, when one or more nucleases and a donor construct are introduced into the cell, the nucleases and/or donor polynucleotide may be carried on the same vector or on different vectors. When multiple vectors are used, each vector may comprise a sequence encoding one or multiple nucleases and/or donor constructs.

Conventional viral and non-viral based gene transfer methods can be used to introduce nucleic acids encoding nucleases and donor constructs in cells (e.g., mammalian cells) and target tissues. Non-viral vector delivery systems include DNA plasmids, DNA minicircles, naked nucleic acid, and nucleic acid complexed with a delivery vehicle such as a liposome or poloxamer. Viral vector delivery systems include DNA and RNA viruses, which have either episomal or integrated genomes after delivery to the cell. For a review of gene therapy procedures, see Anderson, Science 256:808-813 (1992); Nabel & Feigner, TIBTECH 11:211-217 (1993); Mitani & Caskey, TIBTECH 11:162-166 (1993); Dillon, TIBTECH 11:167-175 (1993); Miller, Nature 357:455-460 (1992); Van Brunt, Biotechnology 6 (10): 1149-1154 (1988); Vigne, Restorative Neurology and Neuroscience 8:35-36 (1995); Kremer & Perricaudet, British Medical Bulletin 51 (1): 31-44 (1995); Haddada et al., in Current Topics in Microbiology and Immunology Doerfler and Bohm (eds.) (1995); and Yu et al., Gene Therapy 1:13-26 (1994).

Methods of non-viral delivery of nucleic acids include electroporation, lipofection, microinjection, biolistics, virosomes, liposomes, immunoliposomes, polycation or lipid: nucleic acid conjugates, naked DNA, naked RNA, capped RNA, artificial virions, and agent-enhanced uptake of DNA. Sonoporation using, e.g., the Sonitron 2000 system (Rich-Mar) can also be used for delivery of nucleic acids.

Additional exemplary nucleic acid delivery systems include those provided by Amaxa Biosystems (Cologne, Germany), Maxcyte, Inc. (Rockville, Md.), BTX Molecular Delivery Systems (Holliston, Mass.) and Copernicus Therapeutics Inc, (see for example U.S. Pat. No. 6,008,336). Lipofection is described in e.g., U.S. Pat. Nos. 5,049,386; 4,946,787; and 4,897,355) and lipofection reagents are sold commercially (e.g., Dioctadecylamidoglycylspermine (tradename TRANSFECTAM) and 1-Propanaminium (tradename LIPOFECTIN). Cationic and neutral lipids that are suitable for efficient receptor recognition lipofection of polynucleotides include those of Feigner, WO 91/17424, WO 91/16024.

The preparation of lipid: nucleic acid complexes, including targeted liposomes such as immunolipid complexes, is well known to one of skill in the art (see, e.g., Crystal, Science 270:404-410 (1995); Blaese et al., Cancer Gene Ther. 2:291-297 (1995); Behr et al., Bioconjugate Chem. 5:382-389 (1994); Remy et al., Bioconjugate Chem. 5:647-654 (1994); Gao et al., Gene Therapy 2:710-722 (1995); Ahmad et al., Cancer Res. 52:4817-4820 (1992); U.S. Pat. Nos. 4,186,183, 4,217.344, 4,235,871, 4,261,975, 4,485, 054, 4,501,728, 4,774,085, 4,837,028, and 4,946,787).

Additional methods of delivery include the use of packaging the nucleic acids to be delivered into EnGeneIC delivery vehicles (EDVs). These EDVs are specifically delivered to target tissues using bispecific antibodies where one arm of the antibody has specificity for the target tissue and the other has specificity for the EDV. The antibody brings the EDVs to the target cell surface and then the EDV is brought into the cell by endocytosis. Once in the cell, the contents are released (see MacDiarmid et al. (2009) Nature Biotechnology 27 (7): 643).

The use of RNA or DNA viral based systems for the delivery of nucleic acids encoding engineered CRISPR/Cas systems take advantage of highly evolved processes for targeting a virus to specific cells in the body and trafficking the viral payload to the nucleus. Viral vectors can be administered directly to subjects (in vivo) or they can be used to treat cells in vitro and the modified cells are administered to subjects (ex vivo). Conventional viral based systems for the delivery of CRISPR/Cas systems include, but are not limited to, retroviral, lentivirus, adenoviral, adeno-associated, vaccinia and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system depends on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immunodeficiency virus (SIV), human immunodeficiency virus (HIV), and combinations thereof (see, e.g., Buchscher et al., J. Virol. 66:2731-2739 (1992); Johann et al., J. Virol. 66:1635-1640 (1992); Sommerfelt et al., Virol. 176:58-59 (1990); Wilson et al., J. Virol. 63:2374-2378 (1989); Miller et al., J. Virol. 65:2220-2224 (1991); PCT/US94/05700).

In applications in which transient expression is preferred, adenoviral based systems can be used. Adenoviral based vectors are capable of very high transduction efficiency in many cell types and do not require cell division. With such vectors, high titer and high levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., Virology 160:38-47 (1987); U.S. Pat. No. 4,797,368; WO 93/24641; Kotin, Human Gene Therapy 5:793-801 (1994); Muzyczka, J. Clin. Invest. 94:1351 (1994). Construction of recombinant AAV vectors are described in a number of publications, including U.S. Pat. No. 5,173,414; Tratschin et al., Mol. Cell. Biol. 5:3251-3260 (1985); Tratschin, et al., Mol. Cell. Biol. 4:2072-2081 (1984); Hermonat & Muzyczka, PNAS 81:6466-6470 (1984); and Samulski et al., J. Virol. 63:03822-3828 (1989).

At least six viral vector approaches are currently available for gene transfer in clinical trials, which utilize approaches that involve complementation of defective vectors by genes inserted into helper cell lines to generate the transducing agent.

pLASN and MFG-S are examples of retroviral vectors that have been used in clinical trials (Dunbar et al., Blood 85:3048-305 (1995); Kohn et al., Nat. Med. 1:1017-102 (1995); Malech et al., PNAS 94:22 12133-12138 (1997)). PA317/pLASN was the first therapeutic vector used in a gene therapy trial. (Blaese et al., Science 270:475-480 (1995)). Transduction efficiencies of 50% or greater have been observed for MFG-S packaged vectors. (Ellem et al., Immunol Immunother. 44 (1): 10-20 (1997); Dranoff et al., Hum. Gene Ther. 1:111-2 (1997).

Recombinant adeno-associated virus vectors (rAAV) are a promising alternative gene delivery systems based on the defective and nonpathogenic parvovirus adeno-associated type 2 virus. All vectors are derived from a plasmid that retains only the AAV 145 base pair (bp) inverted terminal repeats flanking the transgene expression cassette. Efficient gene transfer and stable transgene delivery due to integration into the genomes of the transduced cell are key features for this vector system. (Wagner et al., Lancet 351:9117 1702-3 (1998), Kearns et al., Gene Ther. 9:748-55 (1996)). Other AAV serotypes, including AAV1, AAV3, AAV4, AAV5, AAV6, AAV8, AAV9 and AAVrh10, and all variants thereof, can also be used in accordance with the present invention.

Replication-deficient recombinant adenoviral vectors (Ad) can be produced at high titer and readily infect a number of different cell types. Most adenovirus vectors are engineered such that a transgene replaces the Ad Ela, Elb, and/or E3 genes; subsequently the replication defective vector is propagated in human 293 cells that supply deleted gene function in trans. Ad vectors can transduce multiple types of tissues in vivo, including non-dividing, differentiated cells such as those found in liver, kidney and muscle. Conventional Ad vectors have a large carrying capacity. An example of the use of an Ad vector in a clinical trial involved polynucleotide therapy for anti-tumor immunization with intramuscular injection (Sterman et al., Hum. Gene Ther. 7:1083-9 (1998)). Additional examples of the use of adenovirus vectors for gene transfer in clinical trials include Rosenecker et al., Infection 24:1 5-10 (1996); Sterman et al., Hum. Gene Ther. 9:7 1083-1089 (1998); Welsh et al., Hum. Gene Ther. 2:205-18 (1995); Alvarez et al., Hum. Gene Ther. 5:597-613 (1997); Topf et al., Gene Ther. 5:507-513 (1998); Sterman et al., Hum. Gene Ther. 7:1083-1089 (1998).

Packaging cells are used to form virus particles that are capable of infecting a host cell. Such cells include 293 cells, which package adenovirus, and .psi.2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

Gene editing vectors can be delivered ex vivo to CD4/CD8 T cells and/or CD4/CD8 T cells having the CD45RA$^{int}$CD45RO$^{int}$ phenotype followed by reimplantation of the cells into a patient, usually after selection for cells which have incorporated the vector. Formulations including the gene editing vectors for ex vivo administration can include suspensions in liquid or emulsified liquids. The active ingredients often are mixed with excipients which are pharmaceutically acceptable and compatible with the active ingredient. Suitable excipients include, for example, water, saline, dextrose, glycerol, ethanol or the like, and combinations thereof. In addition, the formulation may contain minor amounts of auxiliary substances, such as, wetting or emulsifying agents, pH buffering agents, stabilizing agents or other reagents that enhance the effectiveness of the pharmaceutical composition.

The selected, enriched population CCR5 and/or CXCR4 gene edited CD4/CD8 T cells having the CD45RA$^{int}$CD45RO$^{int}$ phenotype produced by the methods described herein can be included in a composition, such as a pharmaceutical composition, for treating HIV infection in a subject. The composition can also include a pharmaceutically acceptable carrier. With respect to pharmaceutical compositions, the carrier can be any of those conventionally used for the administration of cells. Such pharmaceutically acceptable carriers are well-known to those skilled in the art and are readily available to the public. It is preferred that the pharmaceutically acceptable carrier be one which has no detrimental side effects or toxicity under the conditions of use.

The compositions can be prepared in unit dosage forms for administration to a subject. The amount and timing of administration are at the discretion of the treating clinician to achieve the desired outcome. The compositions can be formulated for systemic (such as intravenous) or local (such as intra-tumor) administration. In one example, an enriched population of CCR5 and/or CXCR4 gene edited CD4/CD8 T cells having the CD45RA$^{int}$CD45RO$^{int}$ phenotype is formulated for parenteral administration, such as intravenous administration. Compositions including enriched population of CCR5 and/or CXCR4 gene edited CD4/CD8 T cells having the CD45RA$^{int}$CD45RO$^{int}$ phenotype as disclosed herein can be used, for example, for the treatment of HIV in a subject.

The compositions for administration can include a solution of the enriched population of CCR5 and/or CXCR4 gene edited CD4/CD8 T cells having the CD45RA$^{int}$CD45RO$^{int}$ phenotype provided in a pharmaceutically acceptable carrier, such as an aqueous carrier. A variety of aqueous carriers can be used, for example, buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions, such as pH adjusting and buffering agents, toxicity adjusting agents, adjuvant agents, and the like, for example, sodium acetate, sodium chloride, potassium chloride, calcium chloride, sodium lactate and the like. The number of cells or concentration of the CCR5 and/or CXCR4 gene edited CD4/CD8 T cells having the CD45RA$^{int}$CD45RO$^{int}$ phenotype in these formulations can vary widely, and will be selected primarily based on fluid volumes, viscosities, body weight and the like in accordance with the particular mode of administration selected and the subject's needs. Actual methods of preparing such dosage forms for use in in gene therapy, immunotherapy and/or cell therapy are known, or will be apparent, to those skilled in the art.

In one example, the enriched population of CCR5 and/or CXCR4 gene edited CD4/CD8 T cells having the CD45RA$^{int}$CD45RO$^{int}$ phenotype can be added to an infusion bag containing 0.9% sodium chloride, USP, and in some cases administered at a dosage of from 0.5 to 15 mg/kg of body weight. An enriched population of CCR5 and/or CXCR4 gene edited CD4/CD8 T cells having the CD45RA$^{int}$CD45RO$^{int}$ phenotype can be administered by slow infusion, rather than in an intravenous push or bolus. In one example, a higher loading dose is administered, with subsequent, maintenance doses being administered at a lower level.

The dose, e.g., number of the CCR5 and/or CXCR4 gene edited CD4/CD8 T cells having the CD45RA$^{int}$CD45RO$^{int}$ phenotype administered should be sufficient to effect, e.g., a therapeutic or prophylactic response, in the subject or animal over a reasonable time frame. For example, the number of the CCR5 and/or CXCR4 gene edited CD4/CD8 T cells having the CD45RA$^{int}$CD45RO$^{int}$ phenotype should be sufficient to treat HIV over a period of from about 6 months, 1 year, 2 years, 3 years, 4 years or more from the time of administration. In certain embodiments, the time period could be even longer. The number of the CCR5 and/or CXCR4 gene edited CD4/CD8 T cells having the CD45RA "CD45RO$^{int}$ phenotype will be determined by, e.g., the efficacy of the CCR5 and/or CXCR4 gene edited CD4/CD8 T cells having the CD45RA$^{int}$CD45RO$^{int}$ phenotype and the condition of the animal (e.g., human), as well as the body weight of the animal (e.g., human) to be treated.

The number of the of CCR5 and/or CXCR4 gene edited CD4/CD8 T cells having the CD45RA$^{int}$CD45RO$^{int}$ phenotype also will be determined by the existence, nature and extent of any adverse side effects that might accompany the administration of an enriched population of CCR5 and/or CXCR4 gene edited CD4/CD8 T cells having the CD45RA$^{int}$CD45RO$^{int}$ phenotype. Typically, the attending physician will decide the number of the inventive CCR5 and/or CXCR4 gene edited CD4/CD8 T cells having the CD45RA™CD45RO$^{int}$ phenotype with which to treat each individual patient, taking into consideration a variety of factors, such as age, body weight, general health, diet, sex, route of administration, and the severity of the condition being treated. By way of example and not intending to limit the invention, the number of the CCR5 and/or CXCR4 gene edited CD4/CD8 T cells having the CD45RA$^{int}$CD45RO$^{int}$ phenotype can be about $10 \times 10^4$ to about $10 \times 10^{11}$ cells per infusion, about $10 \times 10^5$ cells to about $10 \times 10^9$ cells per infusion, or $10 \times 10^7$ to about $10 \times 10^9$ cells per infusion.

It is contemplated that the CCR5 and/or CXCR4 gene edited CD4/CD8 T cells having the CD45RA "CD45RO$^{int}$ phenotype can be used in methods of treating or preventing HIV infection in a subject in need thereof. In this regard, a method of treating or preventing HIV infection in a subject can include administering to the subject an enriched population of CCR5 and/or CXCR4 gene edited CD4/CD8 T cells can have a CD45RA$^{int}$CD45RO$^{int}$ phenotype described herein in an amount effective to treat or prevent HIV in a subject.

In some embodiments, administration of the composition or enriched T-cell population to a subject with HIV is capable of promoting at least one of a sustained increase in absolute CD4 cell numbers, restoration of HIV specific T cell immunity, and a substantial decay in HIV reservoir in the subject. In some embodiments, the subject has undergone and/or continues to undergo antiretroviral therapy The administered CCR5 and/or CXCR4 gene edited CD4/CD8 T cells having the CD45RA$^{int}$CD45RO$^{int}$ phenotype can be cells that are allogeneic or autologous to the host or subject. Preferably, the cells are autologous to the subject.

In some embodiments, the CCR5 and/or CXCR4 gene edited CD4/CD8 T cells having the CD45RA$^{int}$CD45RO$^{int}$ phenotype can be administered in combination with an activator of latent HIV expression. Several activators of latent HIV expression can be used in the compositions and methods described herein. For example, an activator of latent HIV expression can include, but is not limited to, histone deacetylase (HDAC) inhibitors and protein kinase C agonists.

It has been demonstrated that HDAC inhibitors induce the transcriptional activation of the HIV-1 promoter. An HDAC inhibitor may be any molecule that effects a reduction in the activity of a histone deacetylase. This includes proteins, peptides, DNA molecules (including antisense), RNA molecules (including iRNA agents and antisense) and small molecules. In some embodiments, a HDAC inhibitor is a small interfering RNA (siRNA), for example, a si/shRNA directed against HDAC1, 2, 3, 4, 5, 6, 7, 8, 9, 10, or 11. Non-limiting examples of such HDAC inhibitors are set forth below. It is understood that HDAC inhibitors include any salts, crystal structures, amorphous structures, hydrates, derivatives, metabolites, stereoisomers, structural isomers, and prodrugs of the HDAC inhibitors described herein.

In some embodiments, an HDAC inhibitor can include short-chain fatty acids (e.g., Sodium Butyrate, Isovalerate, Valerate, 4-Phenylbutyrate (4-PBA), Phenylbutyrate (PB), Propionate, Butyramide, Isobutyramide, Phenylacetate, 3-Bromopropionate, Tributyrin, Valproic acid (Vpa), Valproate, Valproate semisodium and pivaloyloxymethyl butyrate (PIVANEX)).

In other embodiments, an HDAC inhibitor can include a hydroxamic acid derivative (e.g., suberoylanilide hydroxamic acid (SAHA, vorinostat), Trichostatin analogs such as Trichostatin A (TSA) and Trichostatin C, m-Carboxycinnamic acid bishydroxamide (CBHA), Pyroxamide, Salicylbishydroxamic acid, Suberoyl bishydroxamic acid (SBHA), Azelaic bishydroxamic acid (ABHA) Azelaic-1-hydroxamate-9-anilide (AAHA), 6-(3-Chlorophenylurcido) carpoic hydroxamic acid (3Cl—UCHA), Oxamflatin [(2E)-5-[3-[(phenylsulfonyl)amino]phenyl]-pent-2-en-4-ynohy-droxamic acid], A-161906 Scriptaid, PXD-101 (Prolifix), LAQ-824, CHAP,MW2796, MW2996; or any of the hydroxamic acids disclosed in U.S. Pat. Nos. 5,369,108, 5,932,616, 5,700,811, 6,087,367, and 6,511,990). In certain embodiments, the HDAC inhibitor is SAHA.

In still other embodiments, an HDAC inhibitor can include benzamide derivatives (e.g., CI-994; MS-275 [N-(2-aminophenyl)-4-[N-(pyridin-3-yl methoxycarbonyl)ami-nomethyl]benzamide] and 3'-amino derivative of MS-275).

In yet other embodiments, an HDAC inhibitor can include cyclic peptides (e.g., Trapoxin A (TPX)-cyclic tetrapeptide (cyclo-(L-phenylalanyl-L-phenylalanyl-D-pipecolinyl-L-2-amino-8-oxo-9,10-epoxy decanoyl)), FR901228 (FK 228, depsipeptide), FR225497 cyclic tetrapeptide, Apicidin cyclic tetrapeptide [cyclo(N—O-methyl-L-tryptophanyl-L-isoleucinyl-D-pipecolinyl-L-2-amino-8-oxodecanoyl)], Apicidin Ia, Apicidin Ib, Apicidin Ic, Apicidin IIa, and Apicidin IIb, CHAP, HC-toxin cyclic tetrapeptide, WF27082 cyclic tetrapeptide, and Chlamydocin.

Additional HDAC inhibitors can include natural products, such as psammaplins and Depudecin, Electrophilic ketone derivatives such as Trifluoromethyl ketones, α-keto amides such as N-methyl-α-ketoamides, LSD1 polypeptide, TNF-alpha (TNFα), an inducible transcription factor NF-AT (nuclear factor of activated T cells), and Anti-IκBα or IκBε agents.

The CCR5 and/or CXCR4 gene edited CD4/CD8 T cells having the CD45RA$^{int}$CD45RO$^{int}$ phenotype alone or in combination with the activators of latent HIV expression described herein can be administered to a subject that is latently infected with HIV, e.g., a human latently infected with HIV. The subject can include a subject having a persistent HIV reservoir despite treatment with antiretroviral therapy (e.g., HAART). Thus, in some embodiments, the therapeutically effective amount is the amount of the CCR5 and/or CXCR4 gene edited CD4/CD8 T cells having the CD45RA$^{int}$CD45RO$^{int}$ phenotype to significantly decrease a latent HIV reservoir in a latently HIV infected subject.

In other embodiments, a therapeutically effective amount of CCR5 and/or CXCR4 gene edited CD4/CD8 T cells having the CD45RA$^{int}$CD45RO$^{int}$ phenotype, and optionally an activator of latent HIV expression, can be administered to the subject in combination with another therapeutic agent, which useful in the treatment of HIV infection, such as a component used for HAART or immunotoxins.

As noted above, the CCR5 and/or CXCR4 gene edited CD4/CD8 T cells having the CD45RA$^{int}$CD45RO$^{int}$ phenotype described herein may be combined with one or more additional therapeutic agents useful in the treatment of HIV infection. It will be understood that the scope of combinations of the CCR5 and/or CXCR4 gene edited CD4/CD8 T cells having the CD45RA$^{int}$CD45RO$^{int}$ phenotype with HIV/AIDS antivirals, immunomodulators, anti-infectives or vaccines is not limited to the following list, and includes in principle any combination with any pharmaceutical composition useful for the treatment of AIDS. The HIV/AIDS antivirals and other agents will typically be employed in these combinations in their conventional dosage ranges and regimens as reported in the art.

Examples of antiviral agents include (but not restricted) ANTIVIRALS Manufacturer (Tradename and/or Drug Name Location) Indication (Activity): abacavir GlaxoSmithKline HIV infection, AIDS, ARC GW 1592 (ZIAGEN) (nRTI); 1592U89 abacavir+GlaxoSmithKline HIV infection, AIDS, ARC (nnRTI); lamivudine+ (TRIZIVIR) zidovudine acemannan Carrington Labs ARC (Irving. Tex.) ACH 126443 Achillion Pharm. HIV infections, AIDS, ARC (nucleoside reverse transcriptase inhibitor); acyclovir Burroughs Wellcome HIV infection, AIDS, ARC, in combination with AZT AD-439 Tanox Biosystems HIV infection, AIDS, ARC AD-519 Tanox Biosystems HIV infection, AIDS, ARC adefovir dipivoxil Gilead HIV infection, AIDS, ARC GS 840 (RTI); AL-721 Ethigen ARC, PGL, HIV positive, (Los Angeles, Calif.), AIDS alpha interferon GlaxoSmithKline Kaposi's sarcoma, HIV, in combination w/Retrovir AMD3100 AnorMed HIV infection, AIDS, ARC (CXCR4 antagonist); amprenavir GlaxoSmithKline HIV infection, AIDS, 141 W94 (AGENERASE) ARC (PI); GW 141 VX478 (Vertex) ansamycin Adria Laboratories ARC LM 427 (Dublin, Ohio) Erbamont (Stamford, Conn.) antibody which neutralizes; Advanced Biotherapy AIDS, ARC pH labile alpha aberrant Concepts (Rockville, Interferon Md.) AR177 Aronex Pharm HIV infection, AIDS, ARC atazanavir (BMS 232632) Bristol-Myers-Squibb HIV infection, AIDS, ARC (ZRIVADA) (PI); beta-fluoro-ddA Nat'l Cancer Institute AIDS-associated diseases BMS-232623 Bristol-Myers Squibb/HIV infection, AIDS, (CGP-73547) Novartis ARC (PI); BMS-234475 Bristol-Myers Squibb/

HIV infection, AIDS, (CGP-61755) Novartis ARC (PI); capravirine Pfizer HIV infection, AIDS, (AG-1549, S-1153) ARC (nnRTI); CI-1012 Warner-Lambert HIV-1 infection cidofovir Gilead Science CMV retinitis, herpes, papillomavirus curdlan sulfate AJI Pharma USA HIV infection cytomegalovirus immune MedImmune CMV retinitis globin cytovene Syntex sight threatening CMV ganciclovir peripheral CMV retinitis delavirdine Pharmacia-Upjohn HIV infection, AIDS, (RESCRIPTOR) ARC (nnRTI); dextran Sulfate Ueno Fine Chem. Ind. AIDS, ARC, HIV Ltd. (Osaka, Japan) positive asymptomatic ddC Hoffman-La Roche HIV infection, AIDS, ARC (zalcitabine, (HMD) (nRTI); dideoxycytidine ddI Bristol-Myers Squibb HIV infection, AIDS, ARC; Dideoxyinosinc (VIDEX) combination with AZT/d4T (nRTI) DPC 681 & DPC 684 DuPont HIV infection, AIDS, ARC (PI) DPC 961 & DPC 083 DuPont HIV infection AIDS, ARC (nnRTRI); emvirine Triangle Pharmaceuticals HIV infection, AIDS, ARC (CO-ACTINON) (non-nucleoside reverse transcriptase inhibitor); EL10 Elan Corp, PLC HIV infection (Gainesville, Ga.) efavirenz DuPont HIV infection, AIDS, (DMP 266) (SUS-TIVA) ARC (nnRTI); Merck (STOCRIN) famciclovir Smith Kline herpes zoster, herpes simplex emtricitabine Triangle Pharmaceuticals HIV infection, AIDS, ARC FTC (CO-VIRACIL) (nRTI); Emory University emvirine Triangle Pharmaceuticals HIV infection, AIDS, ARC (COACTI-NON) (non-nucleoside reverse transcriptase inhibitor); HBY097 Hoechst Marion Roussel HIV infection, AIDS, ARC (nnRTI); hypericin VIMRx Pharm. HIV infection, AIDS, ARC recombinant human; Triton Biosciences AIDS, Kaposi's sarcoma, interferon beta (Almeda, Calif.); ARC interferon alfa-n3 Interferon Sciences ARC, AIDS indinavir; Merck (CRIXIVAN) HIV infection, AIDS, ARC, asymptomatic HIV positive, also in combination with AZT/ddI/ddC (PI); ISIS 2922 ISIS Pharmaceuticals CMV retinitis JE2147/AG1776; Agouron HIV infection, AIDS, ARC (PI); KNI-272 Nat'l Cancer Institute HIV-assoc. diseases lamivudine; 3TC Glaxo Wellcome HIV infection, AIDS, (EPIVIR) ARC; also with AZT (nRTI); lobucavir Bristol-Myers Squibb CMV infection; lopinavir (ABT-378) Abbott HIV infection, AIDS, ARC (PI); lopinavir+ritonavir Abbott (KA-LETRA) HIV infection, AIDS, ARC (ABT-378/r) (PI); mozenavir AVID (Camden, N.J.) HIV infection, AIDS, ARC (DMP-450) (PI); nelfinavir Agouron HIV infection, AIDS, (VIRACEPT) ARC (PI); nevirapine Bocheringer HIV infection, AIDS, Ingleheim ARC (nnRTI); (VIRAMUNE) novapren Novaferon Labs, Inc. HIV inhibitor (Akron, Ohio); pentafusaide Trimeris HIV infection, AIDS, ARC T-20 (fusion inhibitor); peptide T Peninsula Labs AIDS octapeptide (Belmont, Calif.) sequence PRO 542 Progenics HIV infection, AIDS, ARC (attachment inhibitor); PRO 140 Progenics HIV infection, AIDS, ARC (CCR5 co-receptor inhibitor); trisodium Astra Pharm. Products, CMV retinitis, HIV infection, phosphonoformate Inc other CMV infections; PNU-140690 Pharmacia Upjohn HIV infection, AIDS, ARC (PI); probucol Vyrex HIV infection, AIDS; RBC-CD4 Sheffield Med. Tech HIV infection, AIDS, (Houston Tex.) ARC; ritonavir Abbott HIV infection, AIDS, (ABT-538) (RITO-NAVIR) ARC (PI); saquinavir Hoffmann-LaRoche HIV infection, AIDS, (FORTOVASE) ARC (PI); stavudine d4T Bristol-Myers Squibb HIV infection, AIDS, ARC didehydrodeoxy-(ZERIT.) (nRTI); thymidine T-1249 Trimeris HIV infection, AIDS, ARC (fusion inhibitor); TAK-779 Takeda HIV infection, AIDS, ARC (injectable CCR5 receptor antagonist); tenofovir Gilcad (VIREAD) HIV infection, AIDS, ARC (nRTI); tipranavir (PNU-140690) Bochringer Ingelheim HIV infection, AIDS, ARC (PI); TMC-120 &

TMC-125 Tibotec HIV infections, AIDS, ARC (nnRTI); TMC-126 Tibotec HIV infection, AIDS, ARC (PI); valaciclovir GlaxoSmithKline genital HSV & CMV infections virazole Viratek/ICN (Costa asymptomatic HIV positive, ribavirin Mesa, Calif.) LAS, ARC; zidovudine; AZT GlaxoSmithKline HIV infection, AIDS, ARC, (RETROVIR) Kaposi's sarcoma in combination with other therapies (nRTI); [PI=protease inhibitor nnRTI=non-nucleoside reverse transcriptase inhibitor NRTI=nucleoside reverse transcriptase inhibitor].

The additional therapeutic agent may be used individually, sequentially, or in combination with the CCR5 and/or CXCR4 gene edited CD4/CD8 T cells having the CD45RA$^{int}$CD45RO$^{int}$ phenotype. Administration to a subject may be by the same or different route of administration or together in the same pharmaceutical formulation.

According to this embodiment, the CCR5 and/or CXCR4 gene edited CD4/CD8 T cells having the CD45RA$^{int}$CD45RO$^{int}$ phenotype and an activator of latent HIV expression may be coadministered with any HAART regimen or component thereof. The current standard of care using HAART is usually a combination of at least three nucleoside reverse transcriptase inhibitors and frequently includes a protease inhibitor, or alternatively a non-nucleoside reverse transcriptase inhibitor. Subjects who have low CD4+ cell counts or high plasma RNA levels may require more aggressive HAART. For subjects with relatively normal CD4$^+$ cell counts and low to non-measurable levels of plasma HIV RNA over prolonged periods (i.e., slow or non-progressors) may require less aggressive HAART. For antiretroviral-naive subject who are treated with initial antiretroviral regimen, different combinations (or cocktails) of antiretroviral drugs can be used.

Thus, in some embodiments, the CCR5 and/or CXCR4 gene edited CD4/CD8 T cells having the CD45RA$^{int}$CD45RO$^{int}$ phenotype and, optionally, an activator of latent HIV expression may be coadministered to the subject with a "cocktail" of nucleoside reverse transcriptase inhibitors, non-nucleoside HIV reverse transcriptase inhibitors, and protease inhibitors. For example, the CCR5 and/or CXCR4 gene edited CD4/CD8 T cells having the CD45RA$^{int}$CD45RO$^{int}$ phenotype and an HDAC inhibitor may be coadministered with a cocktail of two nucleoside reverse transcriptase inhibitors (e.g., ZIDOVUDINE (AZT) and LAMIVUDINE (3TC)), and one protease inhibitor (e.g., INDINAVIR (MK-639)). The CCR5 and/or CXCR4 gene edited CD4/CD8 T cells having the CD45RA$^{int}$CD45RO$^{int}$ phenotype and optionally an activator of latent HIV expression, such as an HDAC inhibitor, may also be coadministered to the subject with a cocktail of one nucleoside reverse transcriptase inhibitor (e.g., STAVUDINE (d4T)), one non-nucleoside reverse transcriptase inhibitor (e.g., NEVIRAPINE (BI-RG-587)), and one protease inhibitor (e.g., NELFINAVIR (AG-1343)). Alternatively, the CCR5 and/or CXCR4 gene edited CD4/CD8 T cells having the CD45RA$^{int}$CD45RO$^{int}$ phenotype and optionally an HDAC inhibitor may be coadministered to the subject with a cocktail of one nucleoside reverse transcriptase inhibitor (e.g., ZIDOVUDINE (AZT)), and two protease inhibitors (e.g., NELFINAVIR (AG-1343) and SAQINAVIR (Ro-31-8959)).

Coadministration in the context of this invention is defined to mean the administration of more than one therapeutic agent in the course of a coordinated treatment to achieve an improved clinical outcome. Such coadministration may also be coextensive, that is, occurring during overlapping periods of time.

In additional embodiments, immunotoxins can be coadministrered to a subject with the CCR5 and/or CXCR4 gene edited CD4/CD8 T cells having the CD45RA$^{int}$CD45RO$^{int}$ phenotype. An example of an immunotoxin is an immunotoxin targeted to an HIV protein expressed on the exterior of cells, such as the viral envelope glycoprotein or a portion thereof. The term "immunotoxin" refers to a covalent or non-covalent linkage of a toxin to an antibody, such as an anti HIV envelope glycoprotein antibody. The toxin may be linked directly to the antibody, or indirectly through, for example, a linker molecule. The toxin can be selected from the group consisting of ricin-A and abrin-A.

Activation of latent HIV expression (also referred to as reactivation of latent HIV expression) results in the conversion of latently infected cells to productively infected cells. This transition can be measured by any characteristic of active viral infection, e.g., production of infectious particles, reverse transcriptase activity, secreted antigens, cell-surface antigens, soluble antigens, HIV RNA and HIV DNA, etc. The methods described herein, may optionally include the step of determining or detecting activation of latent HIV expression. In one embodiment, such a method comprises determining or detecting an mRNA, e.g., an HIV mRNA. Other mRNAs, such as Tat mRNA, NF-κB mRNA, NF-AT mRNA and other mRNAs encoding polypeptides can also be determined using the well known methods including but not limited to hybridization and amplification based assays.

In another embodiment, amplification-based assays are used to measure the expression level of an HIV gene. In one embodiment, activation of latent HIV expression can be detecting by determining the expression level of an HIV polypeptide. The expression level of an HIV polypeptide may be determined by several methods, including, but not limited to, affinity capture, mass spectrometry, traditional immunoassays directed to HIV proteins (such as gp120 and reverse transcriptase), PAGE, Western Blotting, or HPLC as further described herein or as known by one of skill in the art.

Detection paradigms that can be employed to this end include optical methods, electrochemical methods (voltametry and amperometry techniques), atomic force microscopy, and radio frequency methods, e.g., multipolar resonance spectroscopy. Illustrative of optical methods, in addition to microscopy, both confocal and non-confocal, are detection of fluorescence, luminescence, chemiluminescence, absorbance, reflectance, transmittance, and birefringence or refractive index (e.g., surface plasmon resonance, ellipsometry, a resonant mirror method, a grating coupler waveguide method or interferometry).

In some embodiments, global sequencing and 454 pyrosequensing of HIV based vector constructs and the PCR products described herein can be performed to confirm the production and purity of an autologous virus population. 454 is a simple, efficient, and cost effective means to obtain approximate genetic diversity in the samples. In an exemplary embodiment, DNA vectors and plasma RNA will be amplified with bar-coded primers and then sequenced using a 454 JR to obtain an average of ~2000 reads per amplicon/sample.

The invention is further described in detail by reference to the following experimental examples. These examples are provided for purposes of illustration only, and are not intended to be limiting unless otherwise specified. Thus, the invention should in no way be construed as being limited to the following examples, but rather should be construed to encompass any and all variations which become evident as a result of the teaching provided herein.

Example

In this example, we show the immune reconstitution and virological outcomes from two independent clinical trials in which HIV-infected adults received a single infusion of CCR5 gene edited CD4+ T cells. In the first study (SB-728-0902 clinical trial), we found that this intervention led to higher CD4+ T cell numbers and restoration of global T cell homeostasis in a group of individuals who previously failed to normalize their CD4+ T cell counts despite long-term effective ART. Importantly, we observed a significant long-term decay of the size of the total HIV reservoir in the majority of participants, with a decrease in HIV DNA of over 1 $\log_{10}$ copies DNA per million cells in 4 out of the 9 individuals. Although these results were generated using measures of HIV DNA that do not include the HIV replication competent reservoir, the highly significant observed decrease in the HIV reservoir is in sharp contrast to the very stable levels reported during long-term ART and in recent clinical trials using latency reversal agents. These outcomes appeared to be due to the continuous replacement of short-lived HIV-infected cells by uninfected $CD45RA^{int}RO^{int}$ $T_{SCM}$-derived cells. In the second study (SB-728-1101 clinical trial), we confirmed that a single infusion of these CCR5 gene edited cells resulted in the generation of this novel $CD45RA^{int}RO^{int}$ $T_{SCM}$ subset and that a higher frequency of such cells was associated with improved control of HIV replication following ART interruption. These observations support a model in which CCR5 gene editing of memory CD4+ stem cells allow these cells to expand and differentiate into other memory subsets in the presence of virus and provide protection from infection to their progeny.

Materials and Methods

The SB-728-0902 clinical trial is a Phase 1, open label, uncontrolled, nonrandomized study of individuals with chronic HIV infection treated with ART (ClinicalTrials.gov #NCT01044654). The study was sponsored by Sangamo Therapeutics and was conducted at two centers in the United States between December 2009 and April 2014. The primary objective of the study was to assess the safety and tolerability of ascending dose of autologous CD4+ enriched T cells edited at the CCR5 gene by ZFNs (SB-728-T cells). Secondary objectives included the assessment of increases in CD4+ T cell counts, long-term persistence of CCR5 gene edited cells, homing to gut mucosa, and the effects on HIV viral persistence (HIV RNA and proviral DNA). A total of 9 participants were enrolled into three ascending dose cohorts, with three participants in each cohort. All participants were followed weekly for the initial 4 weeks and then monthly thereafter for one year, after which they were enrolled in a three-year safety study. Participant 1-01 underwent a treatment interruption between month 12 and 31.

The SB-728-1101 clinical trial is a Phase 1, open label, uncontrolled, nonrandomized study of individuals with chronic HIV infection treated with ART (ClinicalTrials.gov #NCT01543152). The study was sponsored by Sangamo Therapeutics and was conducted at 12 centers in the United States between March 2012 and January 2017. The primary objective of the study was to evaluate the safety and tolerability of escalating doses of cyclophosphamide (CTX) pre-treatment to promote CD4+ T cell expansion after administration of a single dose of SB-728-T cells. Participants received CTX at doses of 0.1 (Cohort 1, n=3), 0.5 (Cohort 2, n=6), 1.0 (Cohort 3, n=3), 1.5 (Cohort 5, n=3) and 2.0 g/m2 (Cohort 4, n=3) one day before infusion of SB-728-T cells. Participants subsequently received between ~10 to 40 billion SB-728-T cells. All participants were followed weekly for the initial 4 weeks, bi-monthly until week 14, monthly until week 22, and then every 2 months until month 12. ART was discontinued 6 weeks after SB-728-T infusion for a period of 16 weeks (FIG. 17A). Secondary objectives included the evaluation of the effect of SB-728-T cells on plasma HIV-1 RNA levels following ART interruption. During the treatment interruption, ART was reinstituted in participants whose CD4+ T cell counts dropped to <500 cells/u L and/or whose HIV-RNA increased to >100,000 copies/mL on three consecutive weekly measurements. All participants completed the 1-year study and were enrolled in a 3-year long-term safety study with the exception of one participant who withdrew from the study. One participant (03-003) did not interrupt ART.

The final clinical protocol, amendments, and consent documents were reviewed and approved by the NIH Recombinant DNA Advisory committee, as well as institutional review board and institutional biosafety committee (as required) at each study center. All participants provided written informed consent.

Enrollment Criteria

SB-728-0902 Trial

Eligible participants were 18 years of age or older and were infected with HIV, as documented by ELISA. Participants were aviremic (undetectable HIV RNA), receiving stable ART with CD4+ T cell counts between 200 and 500 cell/µL, had adequate venous access and no contraindications to leukapheresis. The key exclusion criteria included a SNP at the CCR5 zinc finger nuclease target region, current or prior AIDS diagnosis, receiving therapy with maraviroc or immunosuppressives, and hepatitis B or hepatitis C co-infection.

SB-728-1101 Trial

Eligible participants were 18 years of age or older and were infected with HIV, as documented by ELISA. Participants were aviremic on stable ART with CD4+ T cell counts >500/µL, had R5 tropic HIV, and willing to discontinue current ART during the treatment interruption. The key exclusion criteria included adenoviral neutralizing antibodies >40, a SNP at the CCR5 zinc finger nuclease target region, current or prior AIDS diagnosis, receiving therapy with maraviroc or immunosuppressives, and hepatitis B or hepatitis C co-infection.

Cell Manufacture

Briefly, participants underwent a 10L leukapheresis to collect, enrich, modify and expand autologous CD4+ T cells. SB-728-T refers to autologous CD4+ enriched T cells that have been transduced ex vivo with SB-728, a replication deficient recombinant Ad5/35 viral vector encoding the CCR5 specific ZFNs (SBS8196z and SBS8267), and includes a mixture of gene edited and un-edited cells. Expression of CCR5-specific ZFNs induces a double stranded break in the cell's DNA which is repaired by cellular machinery leading to random sequence insertions or deletions (indels) in ~25% of transduced cells. These indels disrupt the CCR5 coding sequence leading to frameshift mutation and termination of protein expression.

Cryopreserved Peripheral Blood Mononuclear Cells (PBMCs) Samples

SB-728-0902

Availability of cryopreserved samples at different time points varied between participants; consequently, time points were grouped into early (14-28 days), mid (4-7 months or 9-10 months), late (11-12 months), and long term (2-3 or 3-4 years) post infusion time points. Baseline samples included cryopreserved PBMCs from the initial leukapheresis (2-3 months before infusion) as well as from a small volume blood draw 1-2 weeks before infusion. PBMCs from participants 1-01, 1-02, and 1-03 were not cryopreserved until months 6 or 8 post infusion. Most participants agreed to a large volume blood draw (n=9, year 2-3) and/or leukapheresis (n=7, year 3-4) during the long-term follow-up period to allow for assays requiring large amount of cells, such as CCR5 sequencing and integrated HIV DNA quantification in sorted CD4+ T cell subsets. For certain assays, including the ICS assay and CD95 flow cytometry stainings, baseline samples for only 6 participants remained available. Manufacturing samples (SB-728-T products) were also available for all participants.

SB-728-1101

Clinical measures (CD4, CD8 counts, viral load (VL), and the Pentamer Duplication marker) were performed at every time point. Availability of cryopreserved PBMCs at baseline and pre-ATI were not available for Cohorts 1 and 2 participants; consequently immunological (T cell phenotyping, CCR5 DNA sequencing of ZFN mediated mutations in sorted CD4+ subsets) and virological (Integrated HIV DNA) measurements were only performed in participants from Cohorts 3-5. Baseline samples included cryopreserved PBMCs from the initial leukapheresis (2-3 months before infusion) as well as from a small volume blood drawn 1-2 weeks before infusion. Manufacturing samples (SB-728-T products) were also available for Cohorts 3-5 participants.

Rectal and Lymph Node Biopsies

Rectal biopsies were performed for participants of the SB-928-0902 trial at baseline, day 14, month 3, 6 and 12 (n varied between 3 and 9 participants per time point). Mucosal mononuclear cells were isolated from sigmoid colon biopsies obtained by endoscopy via a combination of collagenase digestion and teasing with 18G needles. Inguinal lymph nodes were biopsied from 3 volunteers at one time point (between 9 and 18 months post SB-728-T infusion). Tissues were processed into single cells as described in Anton et al[47] and genomic DNA were isolated for assessment of CCR5 gene modifications.

Quantification of CCR5 Gene Edited CD4+ T Cells by Polymerase Chain Reaction

ZFN-mediated gene modification can generate a wide range of frame-shift mutations to disrupt the CCR5 gene locus. A PCR-based assay was developed to measure the acquisition of a unique duplication of 5-nucleotide (Pentamer) DNA sequence, CTGAT, at the ZFN cleavage site in approximately 25% of the gene edited alleles. Genomic DNA (gDNA) was extracted from PBMCs using a commercially available kit (Masterpure DNA Purification kit, Epicenter, Madison, WI). A standard PCR was performed with 5 μg of gDNA to amplify a 1.1 kb region that contains CCR5 gene modifications. This 1.1 kb amplicon is subsequently evaluated with the two independent qPCRs, one specific for the Pentamer Duplication-CCR5 gene edited allele (by using a primer that contains the Pentamer Duplication), and a second that amplifies all CCR5 alleles. The ratio of Pentamer Duplication-specific templates and the total number of CCR5 alleles yields Pentamer Duplications per 1 million PBMCs. The assay has a sensitivity of one CCR5 gene edited allele per $10^5$ total CCR5 alleles. The frequency of CCR5 gene edited cells in PBMCs was estimated by multiplying the frequency of Pentamer Duplication gene edited cells by 4.

Quantification of CCR5 Gene Modification in SB-728-T Products Using Cel-I

The Cel-I nuclease specifically cleaves DNA duplexes at the sites of distortions created by either bulges or mismatches in the double helical DNA structure. We have adapted protocols using this enzyme for quantification of minor indels typically induced by ZFN-mediated gene modifications. Briefly, the genomic region of interest (CCR5) is PCR amplified, the PCR product is denatured and then allowed to re-anneal to permit wild type and non-homologous end joining-edited alleles to re-anneal together and create hetero-duplexes. The re-annealed PCR products are then digested with the Cel-I nuclease to cut the PCR-amplified DNA at the site of mismatches. Subsequently, the level of ZFN-mediated gene modification can be quantified by determining the ratio of the uncleaved parental fragment to the two lower migrating cleaved products.

Quantification of CCR5 Gene Modification Via Next-Generation Sequencing/MiSeq

The locus of interest (ZFN binding sites in CCR5) was PCR amplified from genomic DNA, and the levels of modification at each locus were determined by paired-end deep sequencing on an Illumina MiSeq sequencer. Paired sequences were merged via_SeqPrep (John St. John). A Needleman-Wunsch alignment was performed between the target amplicon genomic region and the obtained Illumina sequence to map indels. CCR5 sequencing was performed in sorted CD4+ T cell subsets from SB-728-0902 participants in SB-728-T products (n=9) and year 3-4 samples (n=8) as well as from SB-728-1101 Cohorts 3-5 participants in SB-728-T products (n=7) and weeks 6 and 22 samples (n=7). CCR5 gene edited memory subset cell counts were estimated by multiplying each memory subset cell counts by the frequency of CCR5 gene edited alleles within each memory subset as determined by CCR5 sequencing.

Cell Tracking of CCR5 Gene Edited CD45RA$^{int}$RO$^{int}$ T$_{SCM}$ Post SB-728-T Infusion Sequencing of CCR5 ZFN-mediated mutations in sorted CD4+ T cell subsets was used to track differentiation of CD45RA$^{int}$RO$^{int}$ T$_{SCM}$ cells post infusion. First, wild type CCR5 (amplicon) and sequences detected in only 1 of the samples sequenced were excluded from further analysis (~80% of unique CCR5 sequences). Then, for each donor, we identified the sequences expressed only in CD45RA$^{int}$RO$^{int}$ T$_{SCM}$ cells in SB-728-T products and then analyzed their distribution in CD4+ T cell memory subsets at year 3-4 samples (SB-728-0902) or weeks 6 and 22 samples (SB-728-1101).

Estimation of Expansion of SB-728-T Post Infusion

Figure 8A:
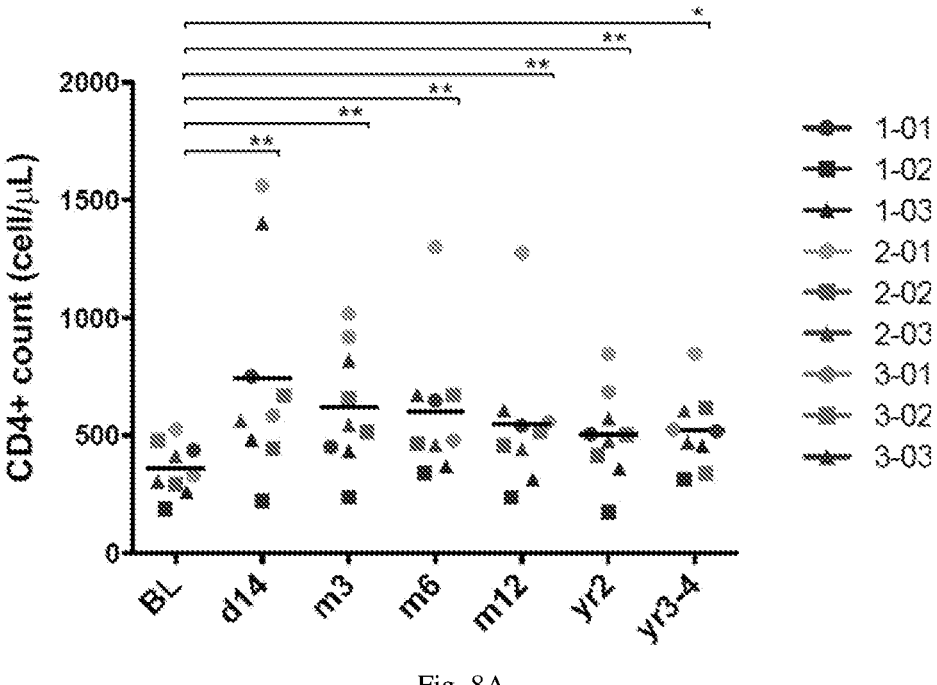
Figure 8B:
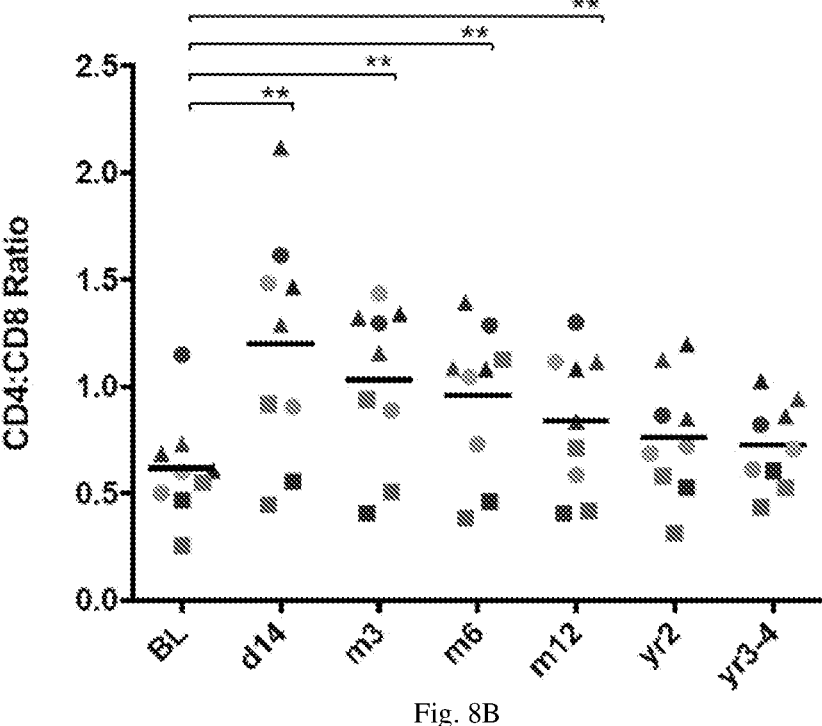
Figure 8C:
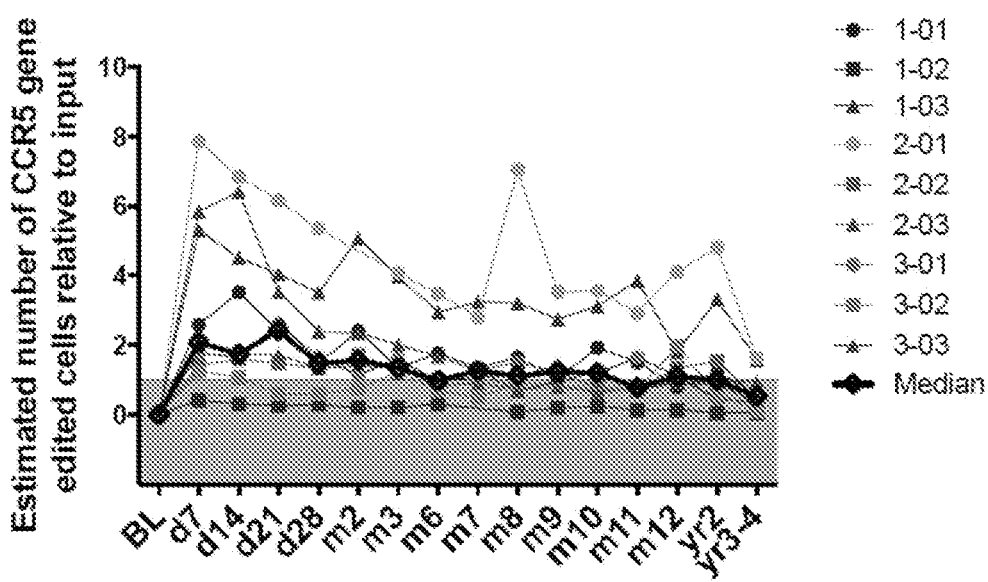
Figure 8D:
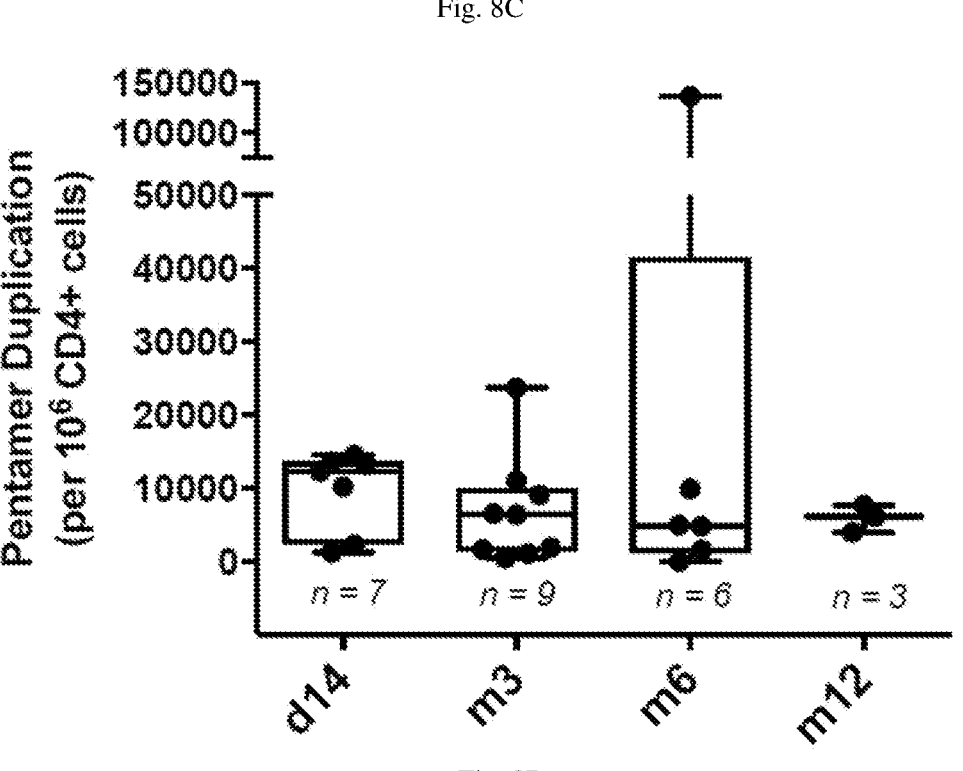
Figure 8E:
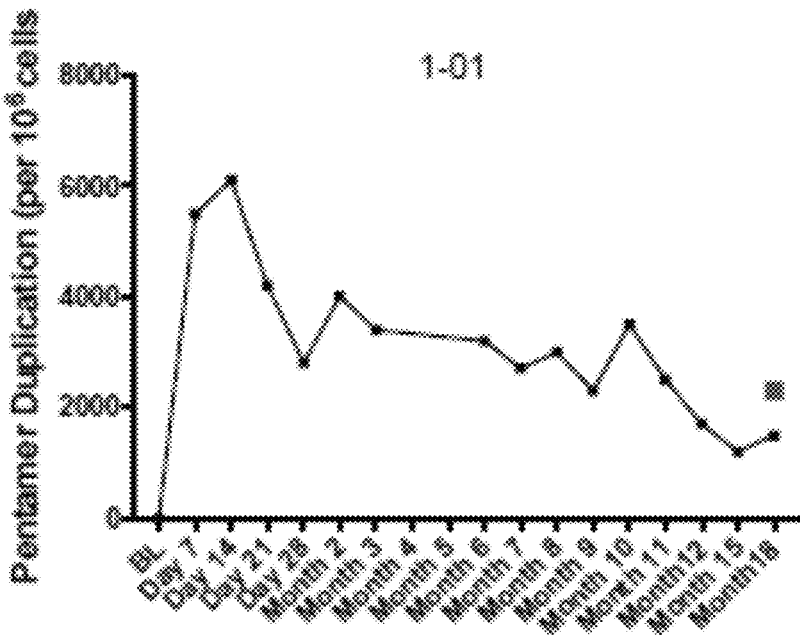
Figure 8E:
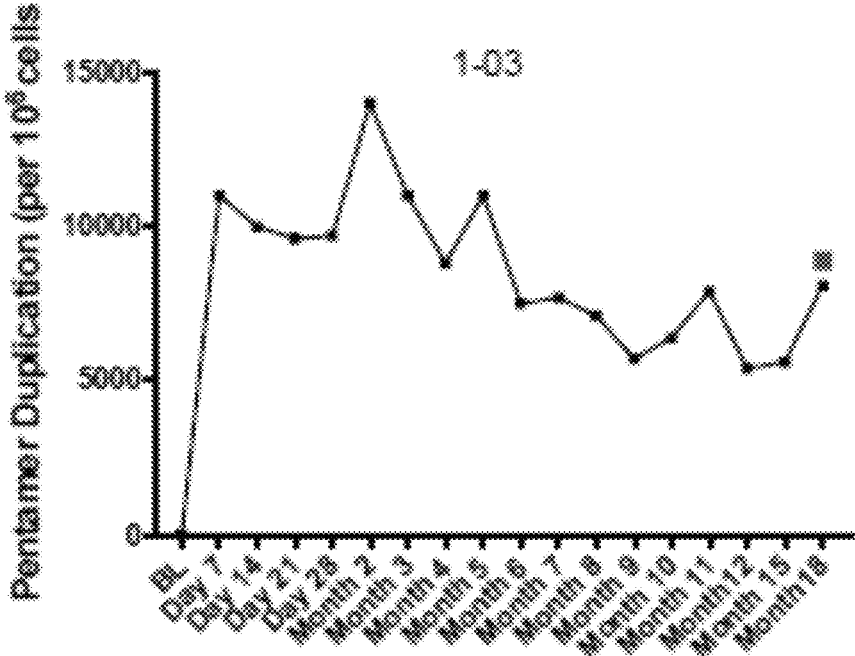
Figure 8E:
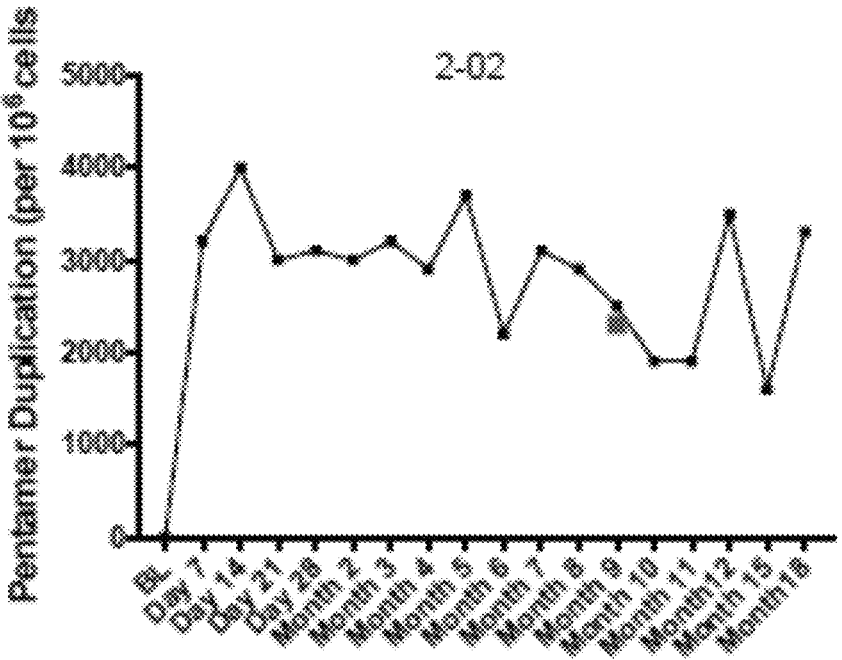

The level of CCR5 gene edited alleles persisting in a participant relative to the amount of CCR5 gene edited cells infused can be estimated using the measured values of CCR5 modification by the Pentamer Duplication marker and CD4+ cell count with the assumptions; 1) blood volume is 4.7 liters, 2) approximately 2.5% of all CD4+ T cells are found in the periphery[49] and 3) SB-728-T products distribution is similar to endogenous CD4+ T cells (levels of CCR5 modification in CD4+ T cells from the sigmoid and inguinal nodes are similar to that in the periphery, FIG. 8E).

Engraftment of SB-728-T=(% CD4 with the Pentamer Duplication marker)×(CD4 count)×(blood volume)×1/2.5%/(% SB-728-T with the Pentamer Duplication maker)×(Total SB-728-T infused)

Cell Phenotyping in SB-728-T Products, at Baseline and Post SB-728-T Infusion Samples Analysis and evaluation of co-inhibitory receptors on CD4+ and CD8+ subsets was performed using one million thawed PBMCs surface stained with either a T$_{SCM}$ panel or a negative regulator panel for 30 minutes at 4° C. prior to fixation with 2% FA (Sigma Aldrich) for 15 min at 22° C. Both panels included CD3 Alexa 700 (clone UCHT1) (BD Biosciences), CD4 Qdot 605 (clone S3.5) (Invitrogen), CD27 APCe780 (clone 0323) (cBioscience), CD8 PerCP (clone SK1), CD45RA BV650 (clone HI100), CD45RO PerCPe710 (clone UCHL1) (Biolegend), and aqua fluorescent reactive dye (a dead cell marker) (Invitrogen). The $T_{SCM}$ panel included CD95 PE-Cy7 (clone DX2), CD58 PE (clone 1C3), CD127 BV421 (clone HIL-7R-M21), CD28 APC (clone CD28.2), CD14 V500 (clone M5E2) (BD Biosciences), CD19 BV510 (clone H1B19) (Biolegend), and CCR7 FITC (clone 150503) (R&D). The negative regulator panel included CCR7 PE-CF594 (clone 150503), CTLA-4 APC (clone BNI3), CD31 PE (clone WM59) (BD Biosciences), Tim-3 BV421 (clone F38-2E2), PD-1 PE-Cy7 (clone EH12.2H7) (Biolegend), and LAG-3 FITC (clone 17B4) (Novus Biologicals). A minimum of 100,000 live cells were acquired within 24 hrs using a BD LSR-II and analyzed using FlowJo version 9.

Cell Sorting

For quantification of the Pentamer Duplication maker and levels of integrated DNA within CD4+ T cell subsets, CD4+ T cells were first isolated from PBMCs by negative magnetic selection (StemCell), and then surface stained with CD3 Alexa 700 (clone UCHT1), CD95 PE-Cy7 (clone DX2), CD58 PE (clone 1C3), CD127 BV421 (clone HIL-7R-M21), CD28 APC (clone CD28.2), CD14 V500 (clone M5E2) (all BD Biosciences), CD4 Qdot 605 (clone S3.5) (Invitrogen), CD27 APCe780 (clone 0323) (eBioscience), CD8 PerCP (clone SK1), CD45RA BV 650 (clone HI100), CD45RO PerCPe710 (clone UCHL1), CD19 BV 510 (clone H1B19) (Biolegend), CCR7 FITC (clone 150503) (R&D), and aqua fluorescent reactive dye (Invitrogen). Up to 200,000 total CD4+ T cells as well as CD4+ T cell subsets were then sorted with the FACSAria (Becton Dickinson) and stored as dry pellets at −80° C. until analysis. For gene array analysis of immune subsets, 10,000 sorted cells were collected directly into RNAse-free 1.5 mL eppendorf tubes containing 500u L of RLT buffer with 1% β-mercaptoethanol and stored at −80° C. until analysis.

HIV DNA in PBMCs. Total and Sorted CD4+ T Cell Subsets

Total HIV DNA in PBMCs was measured by droplet digital polymerase chain reaction. In brief, genomic DNA (gDNA) was extracted from PBMCs using a commercially available kit (Masterpure DNA Purification kit, Epicenter, Madison, WI). 2 µg of gDNA was digested with the restriction enzyme Ddel at 37° C. for 1 hour. PCR droplets were prepared according to manufacturer's recommendations. Briefly, a 20 µL of multiplex PCR mixture is prepared by mixing 250 or 500 ng of the digested gDNA with the DROPLET DIGITAL PCR (tradename DDPCR) 2× Master Mix and two Taqman primer/probe sets. PCR droplets were generated in a droplet generator cartridge (tradename DG8) using the QX-100 droplet generator, where each 20 µL PCR mixture was partitioned into approximately 15,000 nano-liter size droplets. PCR droplets were transferred into a 96-well PCR plate and sealed with foil. Standard PCR was performed with a Bio-Rad CIO00 Thermal Cycler (95° C. (60 sec), 40 cycles of 94° C. (30 sec)/60° C. (60 sec), 98° C. (600 sec)). HIV DNA copy number was evaluated using the QX-100 Droplet Digital PCR system (BioRad, Hercules, CA). The PCR-positive and PCR-negative droplets for HIV gag and RPP30 were determined and template concentrations were calculated by Poisson analysis. HIV copy number was determined by normalizing HIV gag concentration to RPP30 concentration. Integrated DNA was measured as previously described in purified CD4+ T cells from SB-728-0902 participants at baseline, in SB-728-T products, year 2-3 samples (n=9) and in sorted CD4+ T cell subsets in SB-728-T products and year 3-4 samples (n=8). Integrated DNA was also measured in purified CD4+ T cells as well as sorted CD4+ T cell subsets from SB-728-1101 Cohorts 3-5 participants in baseline, weeks 2-6 and 14-22 samples (n=8).

HIV Tropism Assay

HIV Tropism was evaluated using the commercial Trofile® DNA assay (Monogram BioSciences/LabCorp, South San Francisco, CA). Viral envelope DNA sequence was extracted from PBMCs. HIV tropism is determined using a cell based transduction assay where HIV env protein sequences are amplified from PBMC samples, subcloned as a library, packaged into lentiviral vectors, and evaluated using co-receptor restricted cell lines.

Intracellular Cytokine Staining

Thawed PBMCs were rested for 12 hours prior to stimulation of 2 million cells each with Brefeldin A (5 µg/mL) (Sigma Aldrich) and either gag peptides (1 µg/peptide/mL; NIH AIDS reagent program), Staphylococcal enterotoxin B (SEB; lug/mL) or complete media (mock) for 6 hours. Cells were then surface stained with CD3 Alexa 700 (clone UCHT1), CD8 Pacific Blue (clone RPA-T8), CCR7 PE-CF594 (clone 150503), CD14 V500 (clone M5E2) (BD Biosciences), CD4 Qdot 605 (clone S3.5), CD27 APCe780 (clone 0323) (Invitrogen), CD45RA BV 650 (clone HI100), CD19 BV 510 (clone H1B19) (Biolegend), and aqua fluorescent reactive dye (Invitrogen), permeabilised with 0.05% Saponin and stained intracellularly with IL-2 PerCP-Cy5.5 (clone MQ1-17H12), IFNγ APC (clone B27) and TNFα Alexa Fluor 488 (clone MAB11) (BD Biosciences) prior to fixation with 2% formaldehyde. Cells were acquired within 24 hours using a BD LSR-II. A minimum of 500,000 live events was acquired. Cells were analyzed using FlowJo version 9, and the Boolean gating function was used to determine the distribution of polyfunctional CD8+ T subsets.

T Cell Receptor (TCR) Repertoire

TCR repertoire analysis was performed with the immunoSEQ assay (Adaptive Biotechnologies, Seattle, WA). The immunoSEQ method amplifies rearranged TCR CDR3 sequences by multiplex PCR to explore all VB and JB combinations from isolated genomic DNA, and uses high-throughput sequencing technology to sequence TCR CDR3 chains to determine the composition of various T cell clones within each sample. TCR diversity is assessed using the Shannon entropy index, which accounts for both the number of unique clones (richness) and clone distribution (evenness) of the TCR VB CDR3 sequences present in each sample. A larger Shannon entropy index reflects a more diverse distribution of the TCR VB CDR3 sequences.

Gene Microarray and Analyses

Selected CD4+ or CD8+ subsets were sorted into RLT buffer as described above. Specifically, CD4+ $T_{CM}$, CD4+ $T_{TM}$, CD4+ $T_{EM}$ and CD8+total memory cells were sorted at baseline and month 12. In addition, CD4+ memory subsets were also sorted at year 3-4 and included CD45RA$^{int}$RO$^{int}$ $T_{SCM}$, $T_{CM}$, and $T_{EM}$ cells. Sorted cells were lysed for RNA extraction as per manufacturer's instructions (Qiagen, Valencia, CA). T7 oligo (dT) primed reverse transcription reactions were performed followed by in vitro transcription. These products underwent a second round of amplification (MessageAmp II aRNA Amplification kit by Life Technologies) yielding biotin-labeled aRNAs which were hybridized to the Illumina Human HT-12 version 4 Expression Bead- Chip according to the manufacturer's instructions and quantified using an Illumina iScan System.

Analysis of gene array output data was conducted using the R statistical language and the Linear Models for Microarray Data (LIMMA) statistical package from Bioconductor. Briefly, scanned array images were inspected for artifacts and unusual signal distribution within chips, and arrays with low overall intensity or variability were removed from analysis. Diagnostic plots such as density plots, box plots, and heatmaps of between-array distances were used to assess hybridization quality across chips. Intensities were log 2 transformed before being normalized using the quantile normalization method. Probes that did not map to annotated RefSeq genes and control probes were removed. Differentially expressed gene analysis was performed on CD4+ $T_{CM}$ (n=6), CD4+ TIM (n=9), CD4+ $T_{EM}$ (n=7) and CD8+total memory cells (n=9) at month 12 compared to baseline, and on CD4+CD45RA$^{int}$RO$^{int}$ $T_{SCM}$ compared to CD4+ Tom and $T_{EM}$ subsets at year 3-4 (n=7). The difference in gene expression level between the different time points or subsets was determined by performing longitudinal donor-paired analysis. The moderated t-test implemented in the LIMMA package was used to assess the statistical significance (P<0.05) of differential expression of genes between baseline and month. All microarray data have been deposited in GEO under accession number GSE66214.

We used Gene Set Enrichment Analysis (GSEA) to identify enriched biological pathways that are modulated in T memory cells post infusion (FIG. 4). GSEA is a statistical method to determine whether members of a particular gene set preferentially occur toward the top or bottom of a ranked-ordered gene list where genes are ranked by the strength of their association with the outcome of interest. More specifically, GSEA calculates an enrichment score (NES) that reflects the degree to which a set of genes is overrepresented among genes differently expressed. The significance of an observed NES is obtained by permutation testing: resorting the gene list to determine how often an observed NES occurs by chance. Leading Edge analysis is performed to examine the particular genes of a gene set contributing the most to the enrichment. We used the pre-ranked gene list option of GSEA and tested for the enrichment of MSigDB (http://software.broadinstitute.org/gsca/msigdb/) curated gene sets as well as custom gene sets to test the enrichment of Treg and STAT3 pathways within our data. We discarded gene sets with a false discovery rate (FDR)>25% and a nominal P value >0.05.

Figure 4A:
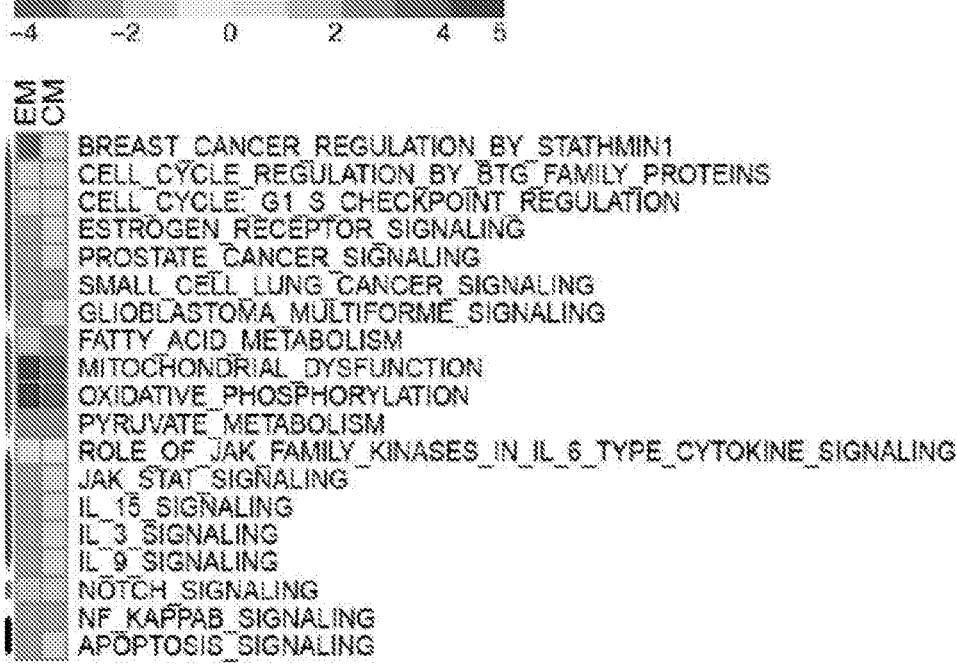
FIGS. 4(A-G) illustrate tables, graphs, and plots showing CD45RA$^{int}$RO$^{int}$ T$_{SCM}$ are distinct from previously identified CD45RA$^+$ T$_{SCM}$ cells. A. Heatmap of selected pathways significantly enriched in genes induced or repressed in CD45RA$^{int}$RO$^{int}$ T$_{SCM}$ compared to T$_{EM}$ and T$_{CM}$ in year 3-4 samples (n=7). A color gradient depicts the GSEA normalized enrichment score (NES ranging from −4 to +5)

We used GSEA as described above with the Fisher combined test approach to identify pathways that are enriched in CD4+CD45RA$^{int}$RO$^{int}$ $T_{SCM}$ versus CD4+ $T_{EM}$ as well as in CD4+CD45RA "RO" $T_{SCM}$ versus CD4+ $T_{EM}$ comparisons. Selected pathways significantly enriched in genes induced or repressed in CD45RA$^{int}$RO$^{int}$ $T_{SCM}$ compared to both $T_{EM}$ and $T_{CM}$ were grouped into several biological functions; cell cycle, cell metabolism, cytokine signaling, Notch signaling and apoptosis (FIG. 4A).

Figure 4B:
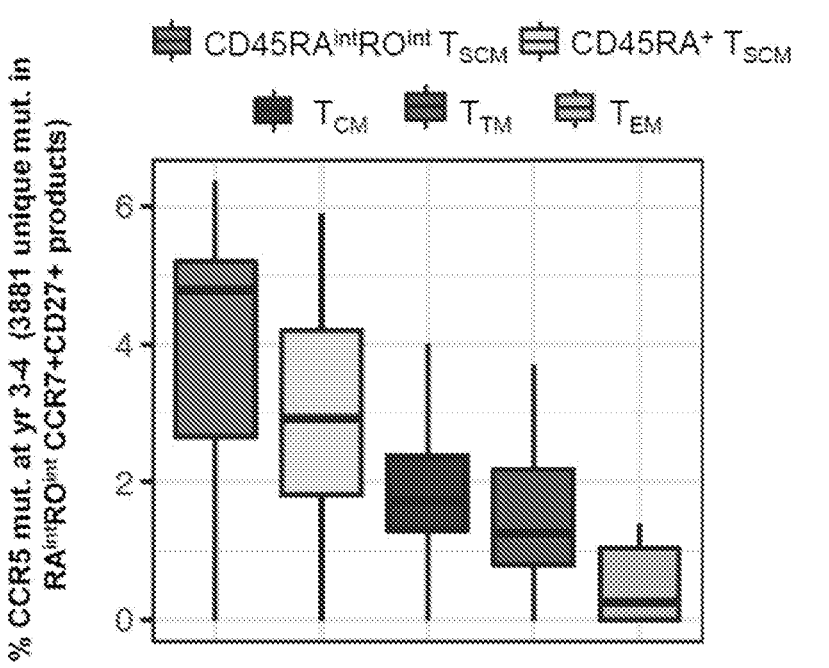
Figure 4C:
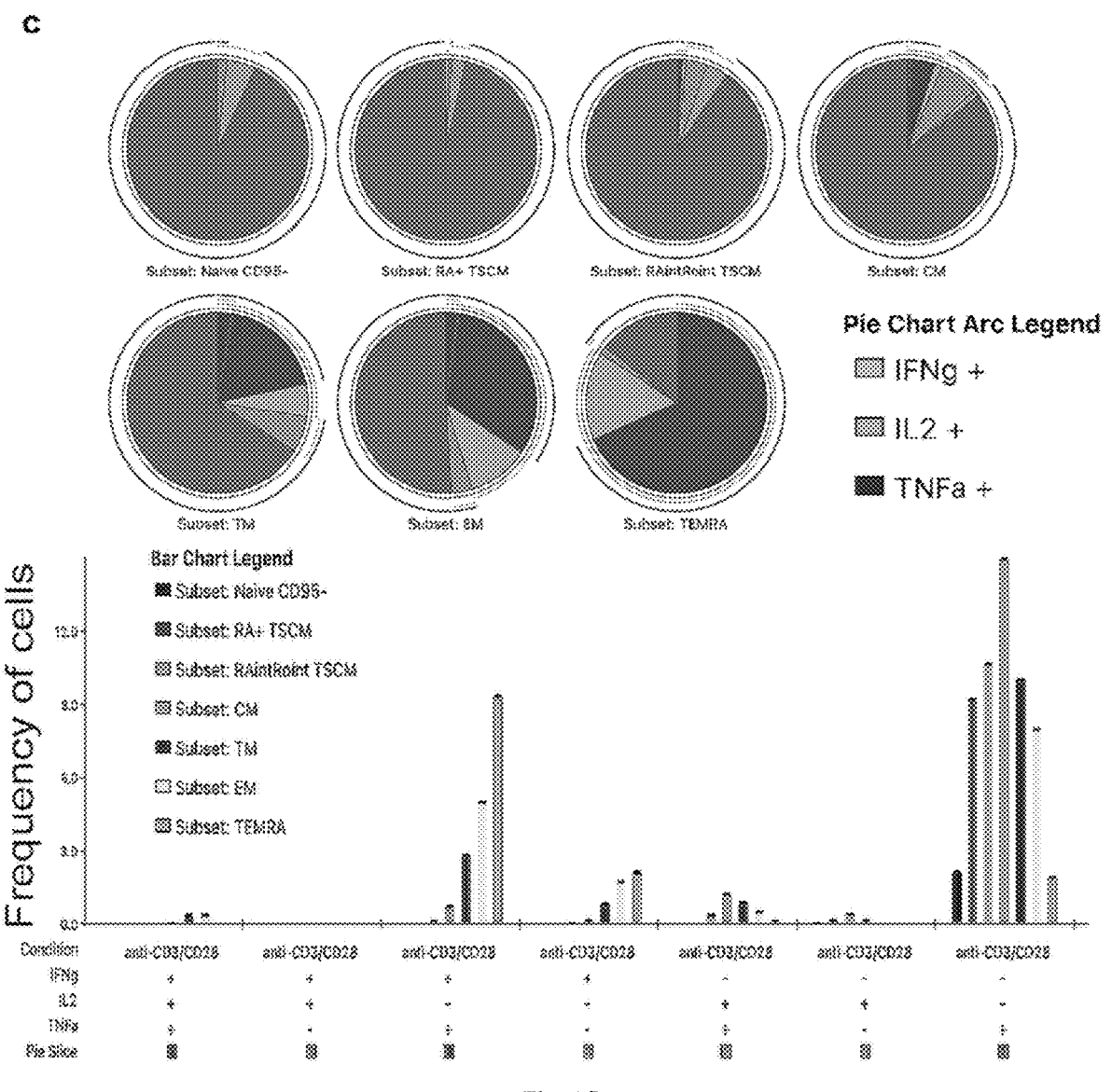
Figure 4D:
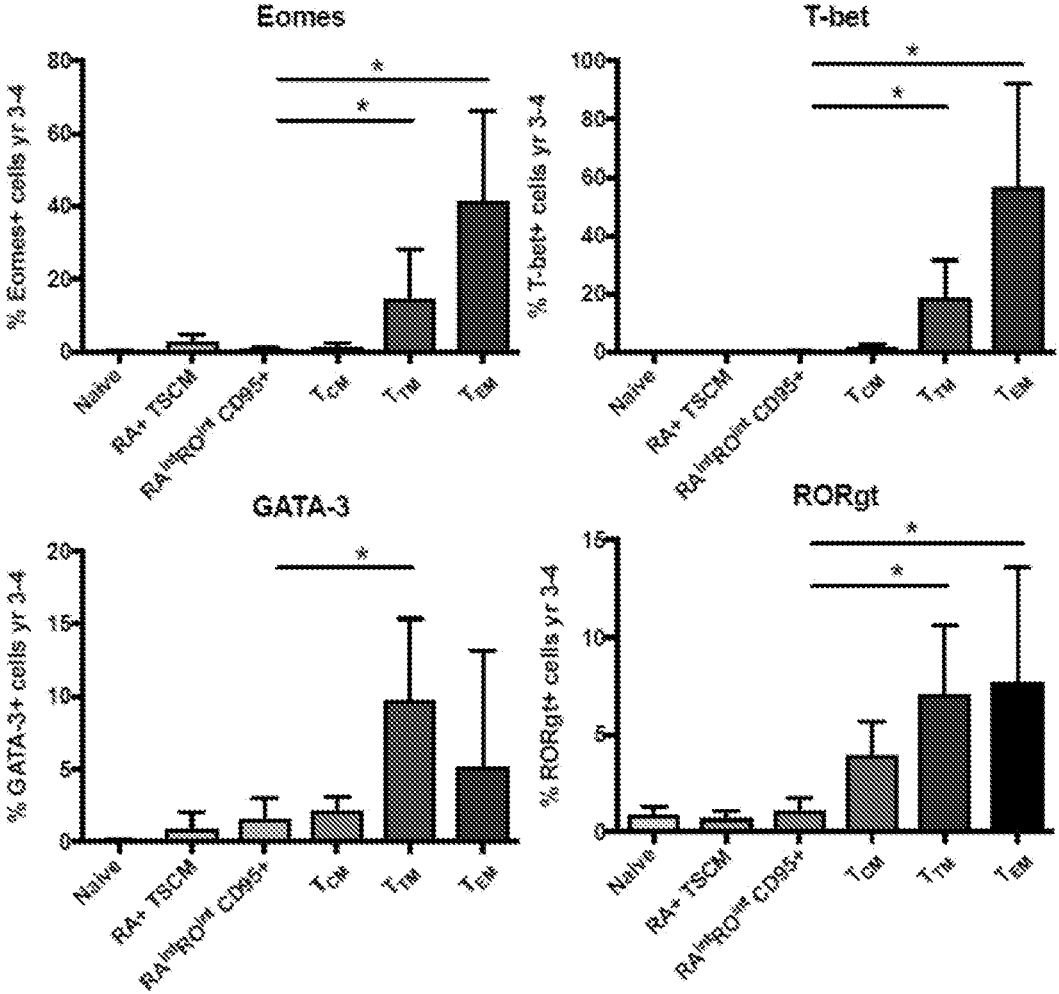

We used circle plots to represent the top enriched pathways that are increased or decreased at month 12 compared to baseline in CD4+ $T_{CM}$, $T_{EM}$ and $T_{TM}$ and CD8+total memory subsets (FIG. 4B,C). To assess whether gene expression profiles of CD4+ memory T cell subsets at 12 months post infusion mimicked the profile of immunological responders (IR), we performed GSEA analysis on a cohort of HIV-infected IR (n=20; CD4+count>500 cells/µL) and Immunological Non-Responder (INR; n=21; CD4+ count <350 cells/µL) participants of an independent cohort (The Cleveland Immune Failure-CLIF-Cohort). All pathways (5/5) that were up-regulated in CD4+ memory T cells at months 12 post SB-728-T products infusion were enriched in IR compared to INR (FIG. 4E, F); these pathways were associated with active metabolism (MYC, OX/PHOS) and proliferation (DNA repair).

To investigate the impact of SB-728-T products on inflammation and immune activation in CD4+ $T_{CM}$ and CD8+total memory cells at month 12 compared to baseline, we first performed a longitudinal donor-paired analysis using the LIMMA approach as described above. Genes were deemed differentially expressed between baseline and month 12 if the probability P was below 0.05. Differentially expressed genes that are induced by interferon type I (IFN I) were identified using the interferome database (http://interferome.its.monash.edu.au/interferome/home.jspx). Selected genes (up or downregulated at month 12 compared to baseline) were selected from each comparison and submitted to GeneMania web server (http://www.genemania.org/) to generate gene interaction networks using the co-expression interaction category.

We used linear regression analysis to identify genes expressed by CD45RA$^{int}$RO$^{int}$ $T_{SCM}$ in year 3-4 samples that correlated with the frequency of total HIV DNA copy per $10^6$ PBMCs at year 2-4 and CD45RA RO$^{int}$ $T_{SCM}$ counts at year 3-4. We fit a linear model (using R language) between gene expression in CD45RA$^{int}$RO$^{int}$ $T_{SCM}$ and the levels of these outcomes as continuous variables and used GSEA to associate a pathway positively or negatively with both of the readouts. We represented the pathways that are modulated in a similar fashion as well as those that are modulated in different directions in FIG. 4g. We highlighted the top pathways that are positively correlated with HIV reservoir size, as measured by total HIV DNA at years 2-4, as well as negatively correlated with CD45RA$^{int}$RO$^{int}$ $T_{SCM}$ count at year 3-4 (FIG. 4H,I) by plotting their normalized enrichment scores. This analysis was performed in 6 out of 7 participants; participant 1-02, who had low engraftment of CD45RA$^{int}$RO$^{int}$ $T_{SCM}$ cells post infusion, was removed from the analysis as it was identified as an outlier in our exploratory analysis.

Statistical Analysis

HIV Reservoir Analysis

The overall decay of the HIV reservoir post infusion (measured as total HIV DNA per $10^6$ PBMC) over time (in days) was modeled using a mixed-effect linear regression model with random intercept as implemented in the function lmer from the R package lme4. The P value associated to the model was estimated using the cftest function as implemented in the R's multicomp package.

Figure 2A:
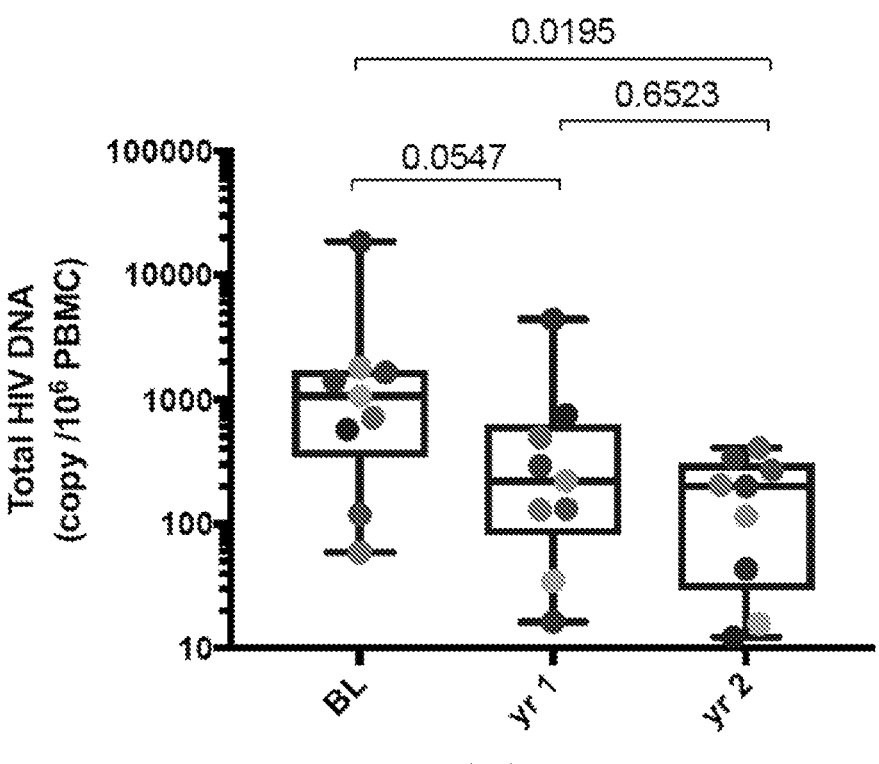
FIGS. 2(A-F) illustrate plots showing decay of the HIV reservoir post SB-728-T infusion correlates with persistence of CCR5 gene edited cells. A, Box-plot with overlaid jitter showing the frequency of cells harboring total HIV DNA per 10$^6$ PBMCs at baseline (BL), year 1, and year 2 post infusion. Box shows median, first and third quartiles, and whiskers extend to maximum and minimum values. Individual data points are shown for all 9 participants with colors corresponding to the different cohorts (cohort 1, 2 and 3 are shown in blue, green and red hues, respectively). BL values for subjects 1-01 and 1-02 were imputed as described in the materials and methods. * P<0.05; Wilcoxon rank-sum test. B, Frequencies of integrated HIV DNA copies per 10$^6$ purified CD4+ T cells are shown at BL and year 2-3 (long-term follow up). Participants in cohorts 1, 2 and 3 are shown in blue, green and red symbols, respectively. * P<0.05; Wilcoxon rank-sum test. C-D, Association between the change in the frequency of PBMCs harboring total HIV DNA at long term time points (Ratio of log 10 values at day 720 over day 0) and the fold-expansion of Pentamer Duplication marked cells at day 21 (C) and years 3-4 post infusion (D). Scatterplots and predictions from robust regression models are shown along with the 95% confidence intervals (shaded regions). E, Representative example of the bi-phasic decay analysis of the HIV DNA (participant 3-01) using Monolix, a software for parameter estimation in non-linear mixed effect models. The blue line represents the bi-phasic exponential fitted line to the HIV DNA copy per 10$^6$ PBMC (represented by the red stars). The lines represent the fast and slow decay and the plateau reached after the end of the slow decay phase, respectively. Inserts highlight the two intersection points that represent the beginning and end of the slow phase decay. F. Representative example of the estimated total HIV DNA per 10$^6$ PBMCs that are expected as a result of dilution (participant 3-01) post infusion (red line). Measured frequencies of total HIV DNA per 10$^6$ PBMCs (blue line) and the estimated frequency of total CCR5 gene edited cells per 10$^6$ PBMCs post infusion (purple line; calculated by multiplying the frequency of Pentamer Duplication marked cells by 4) are also shown.

To analyze the decay of the HIV reservoir for each individual, the frequency of total HIV DNA per $10^6$ PBMC over time was fitted for each individual, with a linear regression model using the GraphPad Prism v7.0 software. The P values and regression coefficients were calculated (FIG. 2A). The missing baseline values for participants 1-01 and 1-02 were calculated by the model fit intercept.

Clinical Data, CCR5 Modification, and Flow Cytometry

The paired Wilcoxon rank-sum two-tailed test was used to perform non-parametric donor-paired two-sided analysis of post infusion changes in CD4+total T cell and subset counts, CD4: CD8 ratio, T cell function, immune checkpoint blockers, and integrated HIV DNA compared to baseline. The Wilcoxon rank-sum two-tailed test was also used to compare the levels of CCR5 gene edited alleles between subsets and to compare the diversity of the TCR repertoire and CCR5 gene edited alleles between SB-738-T products and long-term time points. The Mann-Whitney two-tailed test was used to performed unpaired non-parametric two-sided comparisons in instances where the number of matched participants varied across time points and contained less than 6 matched pairs at a given time point, such as for the frequencies of CD95+ cells post infusion compared to baseline, and the levels of CCR5 gene edited alleles between the different CD4+ memory subsets in the SB-728-0902 study (Pentamer Duplication and CCR5 DNA sequencing). The Spearman's rho (p) test was used to perform non-parametric correlation analysis between various measures and clinical outcomes, including delta CD4+ T cell counts (SB-728-0902), changes in the size of the reservoir calculated using the ratio of the last measured values (year 2-4 time points) over baseline (SB-728-0902), and control of viral replication (SB-728-1101). We controlled for multiple comparison testing by calculating the FDR value using the original FDR method of Benjamini and Hochberg. A P value <0.05 and a Q value <0.25 were considered significant. These statistical analyses were performed using GraphPad Prism v7.0.

Statistical Analysis of Total HIV DNA Decay Post SB-728-T Products Infusion in SB-728-0902

In order to describe the decay of the HIV DNA post infusion that was observed in the six participants, statistical analysis was performed using Monolix version 2016RI, a statistical software package developed by Marc Lavielle and implemented in Matlab, that estimates parameter using a non-linear mixed effect model approach. An individual approach and a population approach (which compiled all six of the patients together) were used to estimate the biphasic exponential decay using the equation, $Y=a+b1*\exp(-r1*time)+b2*\exp(-r2*time)$ (Eq.1). Monolix implements a stochastic approximation of the Expectation maximization algorithm, using a Monte Carlo Markov Chain (MCMC) iterative algorithm. The MCMC iterative method uses the Metropolis-Hastings approach. To perform the fits, we considered different distributions for each of the biphasic decay model equation. The two decay rates, r1 and r2, were estimated following a logit-normal distribution, taking values between (0, 1). The slow and fast intercept parameters, b 1 and b2, along with the plateau parameter a, were estimated using a log-normal distribution, taking only positive values. To ensure model convergence, 2000 Monte Carlo iterations were used in the simulation step. The shape of the Monolix individual fits was also confirmed using a non-liner least squares estimation method, nlsLM package in R, for the same biphasic decay function.

To estimate the time where each of the fast and slow phases of the HIV DNA started dominating, we plotted the slopes associated with each of the fast and slow phases using the following equations:

$$\text{Slope\_fast}=(a+b1+b2)*\exp(-r1*time) \quad \text{(Eq. 2)}$$

$$\text{Slope\_slow}=(a+b2)*\exp(-r2*time) \quad \text{(Eq. 3)}$$

The intersection between the two slopes (Eq. 2&3) is the time where the slow phase begins dominating the fast decay phase. Similarly, the intersection between the slow phase (Eq. 3) and the plateau line, indicated the time where the slow decay phase ended and the HIV DNA reached a new frequency level estimated by the plateau. The calculations for each of the six patients were performed using MATLAB.2016.

Similarly, to estimate the percentage contribution for both the fast and slow phases on the total HIV DNA decay, we used the following equations:

$$\text{Percent\_Fast: } \Phi=b1/(Y0-\text{Plateau})*0.01; \ YO=a+b1+b2 \ (HIV \ DNA \text{ copy at } t=0 \text{ days})$$

$$\text{Percent\_Slow: } Y=100-\Phi$$

Model Selection and Diagnosis

Compared to the population approach results, the individual approach resulted in a better fit. To evaluate the difference between each of the R and Monolix fits, and the individual versus population fitting results, Akiake Information Criterion (AIC) and the Bayesian Information Criterion (BIC) were used. Having a smaller AIC and BIC indicates the most parsimonious model, which was better achieved using an individual approach in Monolix.

Mathematical Model of the Dynamics of CD4+ T-Cell

To investigate the persistence of the CCR5-gene edited memory CD4+ T-cell, we developed a mathematical model to describe the dynamics of the memory CD4+ T-cell population. We divided the memory CD4+ T-cells in to two populations, CCR5-gene edited and non-edited memory CD4+ T-cells. The model considers naïve (N), stem memory $CD45RA^{int}RO^{int}$ (TSCM2, TSCM2$_{GE}$), stem memory $CD45RA^{+}$ (TSCM1, TSCM1$_{GE}$), central memory (CM, CM$_{GE}$), transitional memory (TM, TM$_{GE}$) and effector memory (EM, EM$_{GE}$), where a GE subscript refers to the CCR5 gene-edited CD4 T-cells. The differential equations describing this system are:

$$\frac{dN}{dt} = \lambda - dN\,N + \varphi N\,N + pN\,N$$

$$\frac{dTSCM1}{dt} = -dTS1\,TSCM1 - \varphi TS1\,TSCM1 + pTS1\,TSCM1$$

$$\frac{dTSCM2}{dt} = -dTS2\,TSCM2 - \varphi TS2\,TSCM2 + pTS2\,TSCM2$$

$$\frac{dCM}{dt} =$$
$$-dC\,CM - \varphi C\,CM + pC\,CM + \varphi TS2\,TSCM2 + \varphi TS1\,TSCM1 + \varphi N\,N$$

$$\frac{dTM}{dt} = -dT\,TM - \varphi T\,TM + \varphi T\,TM + \varphi C\,CM$$

$$\frac{dEM}{dt} = -dE\,EM + \varphi T\,TM + pE\,EM$$

$$\frac{dTSCM1_{GE}}{dt} =$$
$$-dTS1_{GE}TSCM1_{GE} - \varphi TS1_{GE}TSCM1_{GE} + pTS1_{GE}TSCM1_{GE}$$

$$\frac{dTSCM2_{GE}}{dt} =$$
$$-dTS2_{GE}TSCM2_{GE} - \varphi TS2_{GE}TSCM2_{GE} + pTS2_{GE}TSCM2_{GE}$$

$$\frac{dCM_{GE}}{dt} = -dC_{GE}CM_{GE} + \varphi TS1_{GE}TSCM1_{GE} +$$
$$pC_{GE}CM_{GE} + \varphi TS2_{GE}TSCM2_{GE} - \varphi C_{GE}CM_{GE}$$

$$\frac{dTM_{GE}}{dt} = -dT_{GE}TM_{GE} + \varphi C_{GE}CM_{GE} + pT_{GE}TM_{GE} - \varphi T_{GE}TM_{GE}$$

$$\frac{dEM_{GE}}{dt} = -dE_{GE}EM_{GE} + \varphi T_{GE}TM_{GE} + pE_{GE}EM_{GE}$$

Using an individual fitting approach in Monolix R2018, we fit both CCR5-gene edited and non-gene edited CD4+ T-cell memory subsets data counts for the 5 patients whom they had an extended ATI interruption period (week 6-month 12) To the ODE model. Given the small sample size, we adopted an individual fitting routine to parameterize the model parameters as described in the previous section (Statistical analysis of total HIV DNA Decay post SB-728-T products infusion in SB-728-0902). For all model parameters, we assumed a log-normal distribution, taking only positive values.

Global Sensitivity Analysis

To determine which parameter most affect cell population magnitude, we performed a sensitivity analysis test using Latin Hypercube Sampling (LHS) and Partial Rank Correlation Coefficients (PRCC) measuring the liner association between model parameters and model outputs. This test allows to study the sensitivity between multiple parameters and model outputs, simultaneously. Given the uncertainty in parameter distributions, we vary the model parameters using a uniform distribution, where the maximum and minimum are taken from the 5 individual fits obtained for each Subject. The monotonicity relationship between model parameters and outputs was confirmed. To ensure accuracy, PRCC values were obtained using 100,000 bins in MAT-LAB.

Estimation of HIV DNA Decay Due to Dilution of Infused Cells in SB-728-0902

The HIV DNA decay post infusion in a participant from the SB-728-0902 study due to dilution by the amount of cells infused can be estimated using the measured values of CCR5 gene modification by the Pentamer Duplication marker and of CCR5 gene modification in SB-728-T products using Cel-I nuclease, with the assumptions; 1) one gene edited allele represents one gene edited cell, 2) CD4+ T cells from SB-728-T products do not contain cells with HIV DNA, and 3) un-edited cells persist similarly to CCR5 gene edited cells post infusion (participants remained on ART).

Estimated frequency of CCR5 gene edited cells in PBMCs=frequency of Pentamer Duplication per $10^6$ PBMCs at each time point*4/1000

Estimated frequency of infused cells in PBMCs=frequency of CCR5 gene edited cells in PBMCs at each time point*(100/frequency of CCR5 gene edited cells in SB-728-T products, as determined by Cel-I nuclease)

Estimated decay of HIV DNA due to infused cells=baseline frequency of cells with HIV DNA*frequency of infused cells in PBMCs for each time point/100

Estimated frequency of HIV DNA due to infused cells=baseline frequency of cells with HIV DNA-estimated decay of HIV DNA due to infused cells for each time point Outliers Participant 1-02 had elevated anti-adenovirus titers which may have impeded on the levels of engraftment of CCR5 gene edited cells and persistence of CD45RA$^{int}$RO$^{int}$ T$_{SCM}$ cells, a population highly enriched in gene edited cells (SB-728-T products are derived from transduction with recombinant Ad5/F35 adenoviral vector encoding the CCR5 targeting ZFNs), and therefore was excluded from selective analyses focused on correlating the expansion of CCR5 gene edited cells and the CD45RA$^{int}$RO$^{int}$ T$_{SCM}$ subset with HIV reservoir decay (such as in FIG. 1c-d, FIG. 2d-c, and FIG. 3g-i).

Results

A Single SB-728-T Infusion LED to a Continuous Decrease in the Size of the HIV Reservoir that Correlates with the Expansion and Persistence of CCR5 Gene Edited Cells The clinical study SB-728-0902 evaluated nine HIV-infected adults on long-term ART who had failed to increase CD4+ T cell counts to levels above 500 cells/μL. At baseline, participants had been on effective ART for 7 to 22 years and had a mean CD4+ T cell count of 363 cells/μL. CD4+ T cell counts were inversely correlated with the levels of integrated HIV DNA (referred to here as the HIV reservoir) at the baseline visit (P=0.017). All participants received a single infusion of ZFN-mediated CCR5 gene edited CD4+ T cells.

Figure 10A:
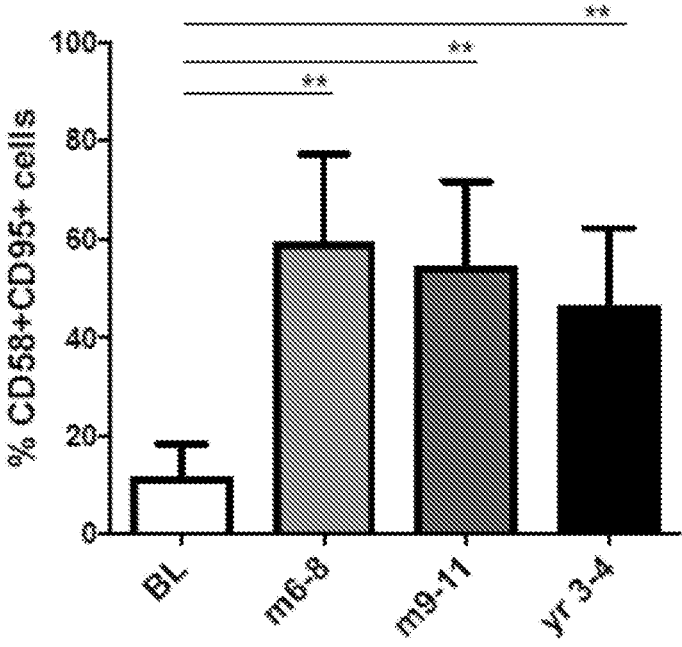
Figure 10B:
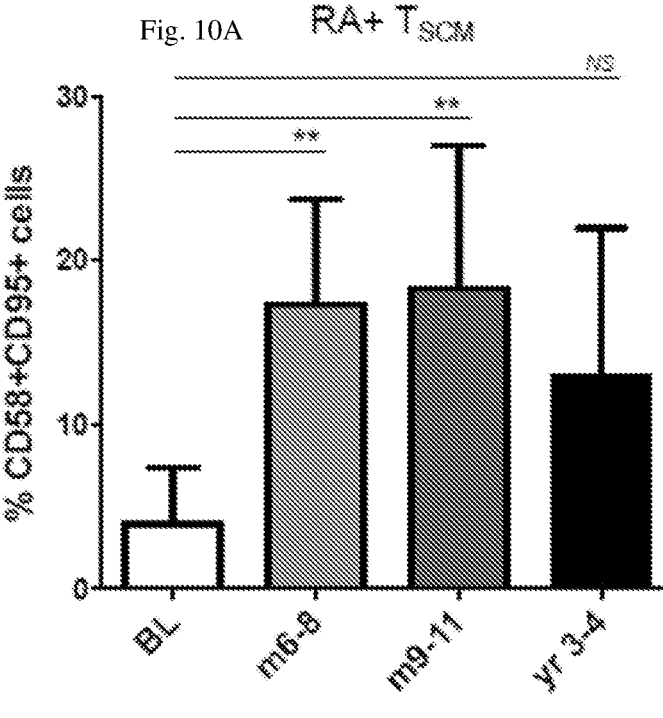
Figures 10C, 10D:
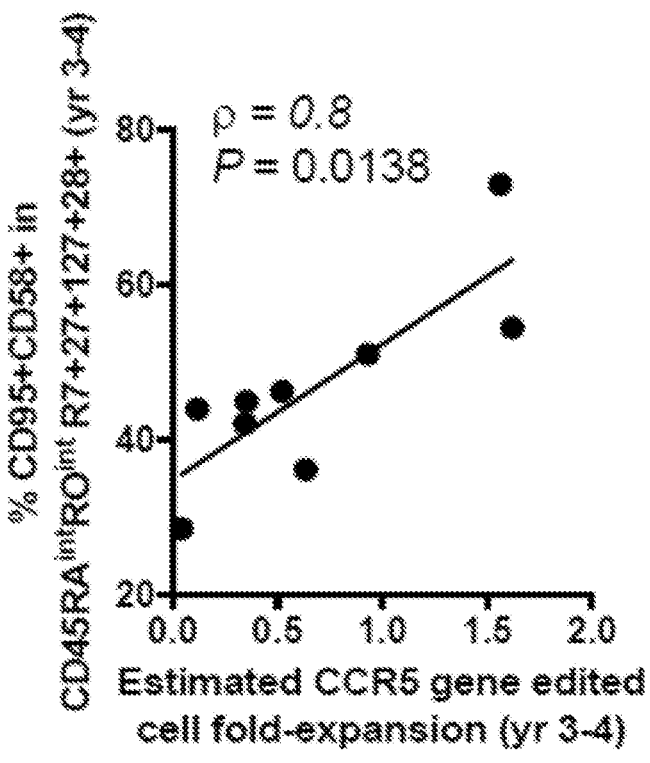
Figure 10E:
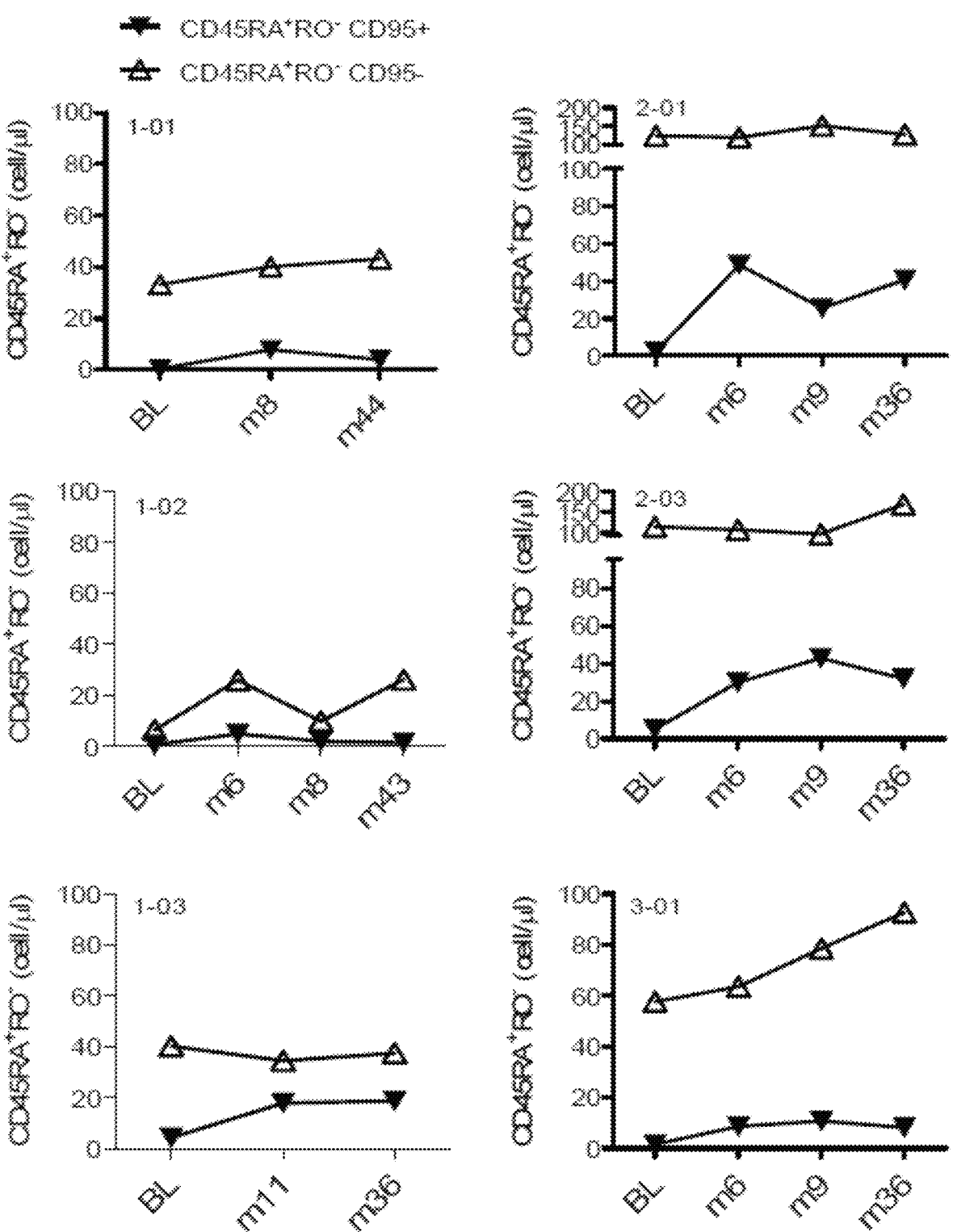
Figure 10F:
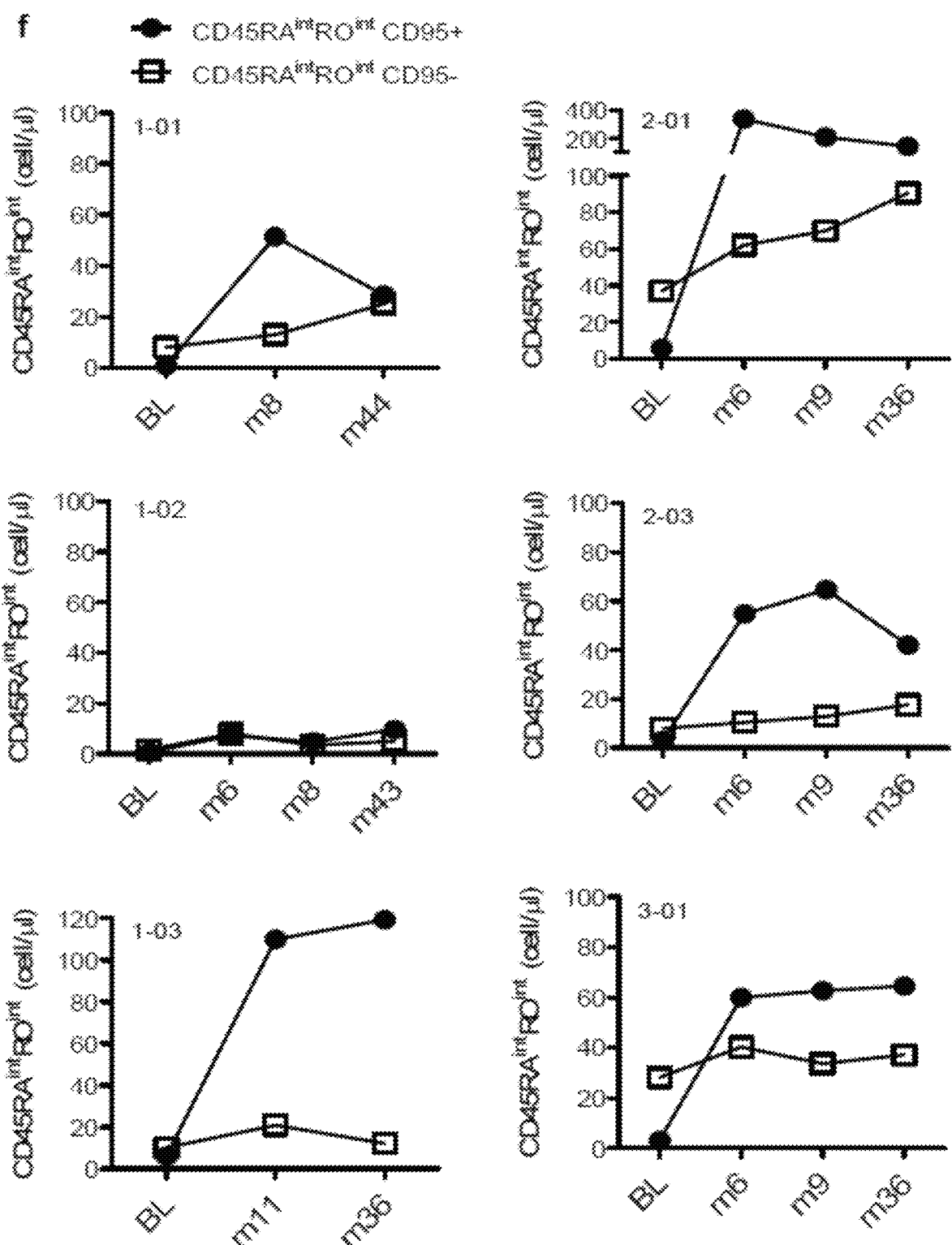

Peripheral CD4+ T cells counts (and the CD4: CD8 ratio) increased within 7 days after the infusion, as expected (see online discussion; FIG. 10A, 10B). Remarkably, this increase was sustained, with CD4+ T cell counts remaining significantly above baseline for 3-4 years during the longitudinal observation (P=0.024) (FIG. 10A). Expansion of CCR5 gene edited cells peaked at 7-21 days post infusion (median 2.4-fold expansion at 21 days; FIG. 10c) and was associated with increased CD4+ T cell counts. CCR5 gene edited CD4+ T cells were detected for up to 4 years in PBMCs (mean of 0.8% marked PBMCs and mean of 2.7% marked CD4+ T cells) and up to 12 months (last measured time point) in rectal biopsies and lymph nodes (FIG. 10d, 10c).

Figure 2B:
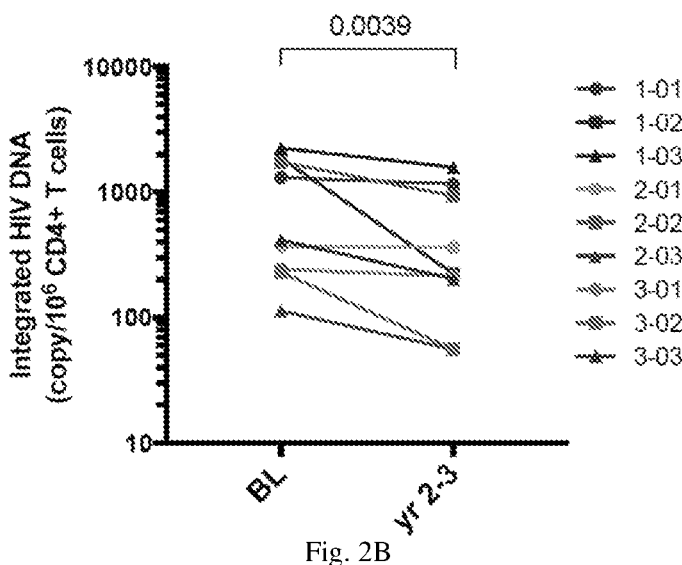
Figure 2C:
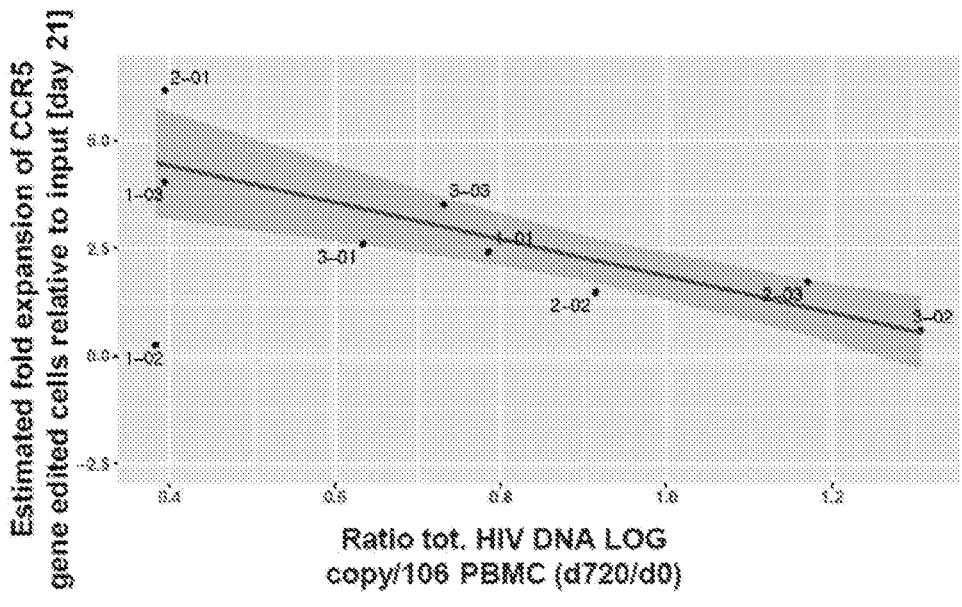
Figure 2D:
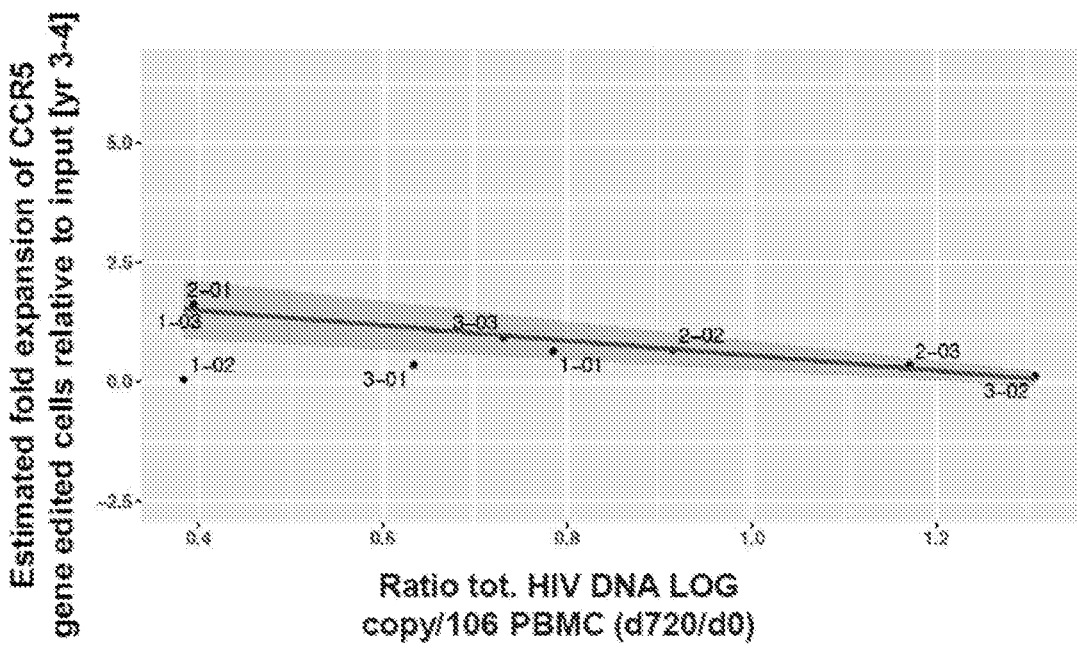

We next determined if the restoration of CD4+ T cell counts post SB-728-T infusion led to a reduction in the frequency of circulating cells containing HIV DNA. We observed a significant decrease in the levels of total HIV DNA was observed two years post infusion when compared to baseline (P=0.0195; mean decay of −0.91 log 10, 95% confidence interval (CI)-1.71 to −0.11) (FIG. 2A). Furthermore, a significant decay in frequencies of CD4+ T cells with integrated DNA (FIG. 2B) was also observed post infusion. Higher levels of CCR5 gene edited cell expansion at early (21 days) and long-term time points (~3-4 years) correlated with greater sustained reduction in HIV DNA levels (r2=0.62, P=0.0014 and r2=0.91, 0.0003, respectively) (FIGS. 2C and 2D). These results strongly suggest that persistence of infused CD4+ T cells has an impact on the decay of the HIV reservoir size.

Figure 2E:
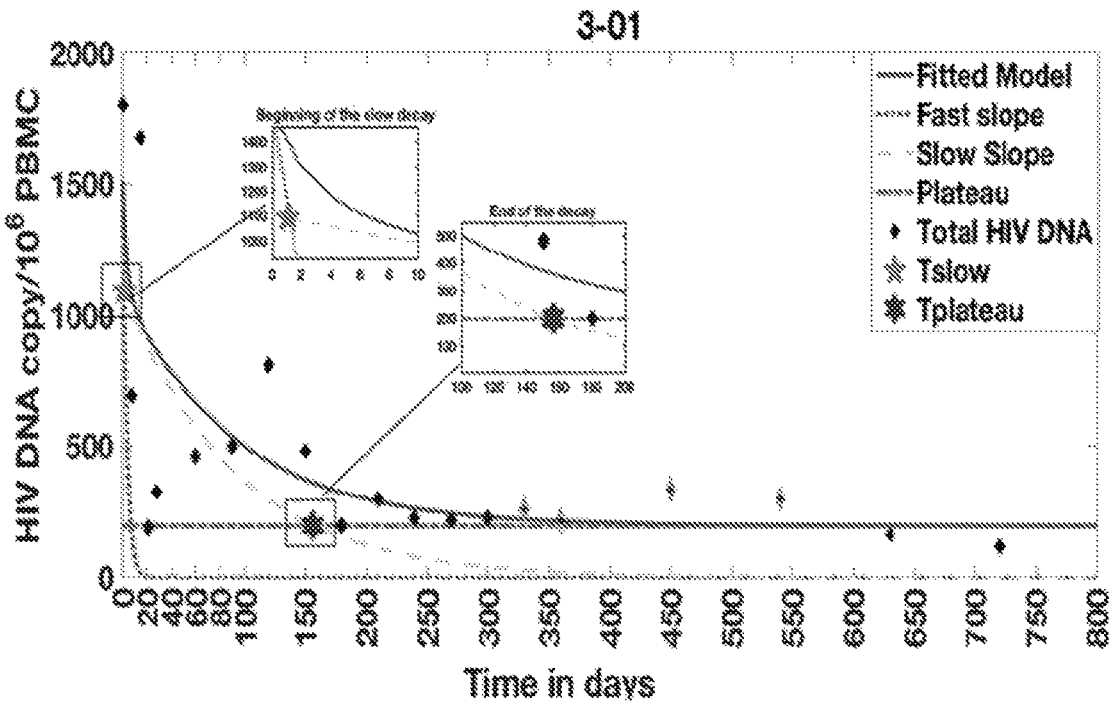
Figure 2F:
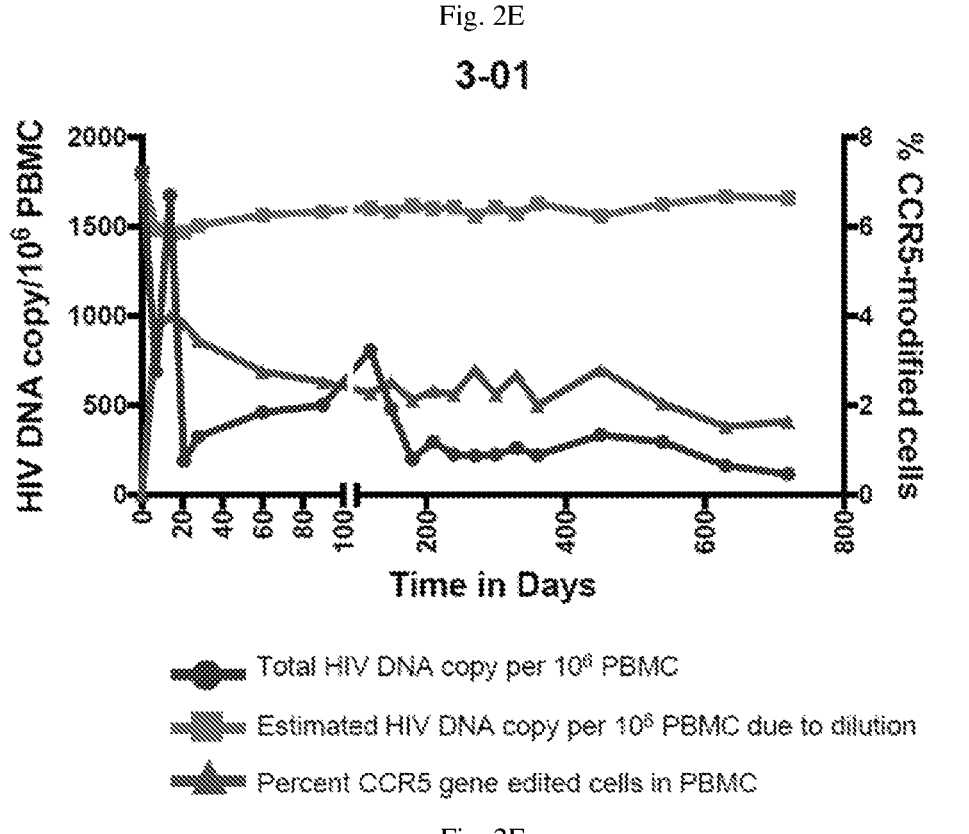

Interestingly, CD4+ T cells from SB-728-T products showed significantly lower frequencies of latently-infected cells than CD4+ T cells from baseline (P=0.004, FIG. 16A). A two-phase decay model was used to determine if the persistence of infused cells with low levels of integrated HIV DNA solely contributed to the decay of the HIV reservoir through dilution during the peak proliferation of infused cells. The slope of HIV DNA decay was greatest during the first 1-15 days of infusion during which a mean of 30.47% (95% CI, 9.664-51.28) of the decline was observed. After which the levels of HIV DNA continued to decrease at a slower rate with a half-life of 211 days (95% CI; 56-365). This slower decay phase accounted for the majority of the decrease in HIV DNA (mean of 69.5% of the decline) (FIG. 2E). The estimated frequency of cells with HIV DNA as a result of dilution was subsequently calculated for each time point (FIG. 2F). We found that the observed frequencies of cells with HIV DNA became lower than those estimated by dilution alone after approximately 100 days, demonstrating that dilution alone could not account for the long-term decrease in frequencies of HIV-infected cells. Our analysis suggests that persistence of infused cells leads to HIV decay through mechanisms which may include restored T cell homeostasis and/or replenishment of the CD4+ T cell pool by uninfected cells.

Figures 3A, 3B:
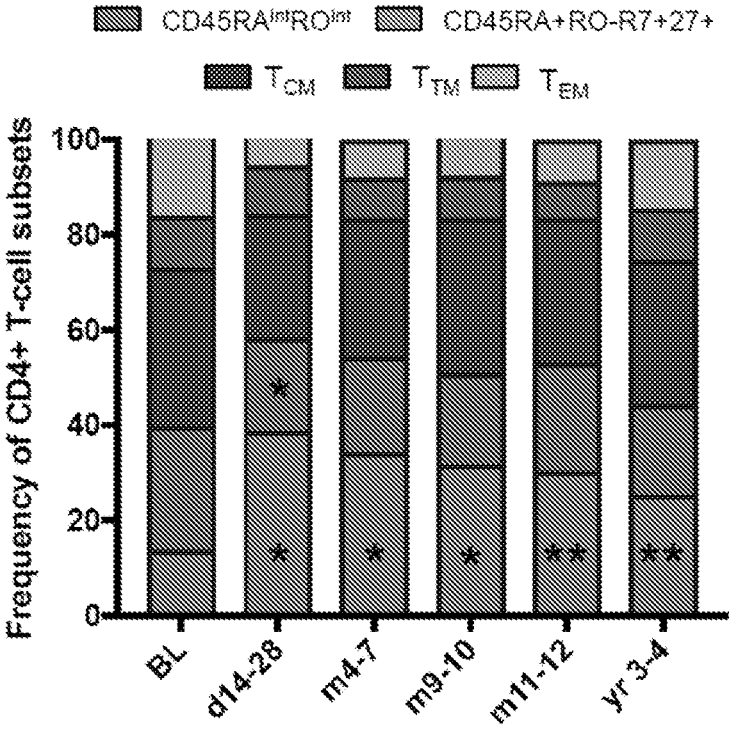
FIGS. 3(A-D) illustrate graphs and plots showing identification of a novel memory stem cell CD4+ T cell subset (CD45RA$^{int}$RO$^{int}$ cells expressing CD95) that contributes to the persistence of CCR5 gene edited T cells and total CD4+ T cells but contributes minimally to the CD4+ T cell reservoir. A, Bar chart depicting the mean distribution of naïve, T$_{CM}$, T$_{TM}$, T$_{EM}$, and CD45RA$^{int}$RO$^{int}$ frequencies in CD4+ T cells at BL (7 days to 3 months prior to infusion; n=9), early (day 14-28; n=6), mid (month 4-7, n=7), and long-term time points (year 3-4, n=9) post infusion. * P<0.05, ** P<0.01; Wilcoxon rank-sum test. B, Median frequency of the Pentamer Duplication marker per 10$^6$ cells measured in sorted T$_{CM}$, T$_{TM}$, and T$_{EM}$ memory subsets at d14-m4 (n=7 for all 3 subsets), m6-8 (n=7, 7, and 6, respectively), m11-12 (n=7, 7, and 6, respectively), and yr3-4 (n=7, 7, and 5, respectively), and in CD45RA$^+$ T$_{SCM}$ and CD45RA$^{int}$RO$^{int}$ T$_{SCM}$ at m9-10 (n=6 and 5, respectively), m11-12 (n=3 and 5, respectively), and yr3-4 (n=7 and 8, respectively) post infusion. N/A=not done; limitations in cryopreserved PBMCs prevented quantification of T$_{SCM}$ subsets at early time points. C. Box-plots with overlaid jitter depicting the percent contribution of each subset towards the CD4+ T cell HIV reservoir in year 3-4 samples (n=8 due to limitations in cell availability). Box shows median, first and third quartiles, and whiskers extend to maximum and minimum values. P values of Wilcoxon rank-sum test are shown. D. 3-D scatter plot showing the change in the frequency of PBMCs harboring total HIV DNA post infusion (Ratio of log 10 values at day 720 over day 0) as a function of CD45RA$^{int}$RO$^{int}$ T$_{SCM}$ cell counts at years 3-4, the frequency of Pentamer Duplication in CD45RA$^{int}$RO$^{int}$ T$_{SCM}$ at years 3-4, and the ratio of the frequency of Pentamer Duplication in CD45RA$^{int}$RO$^{int}$ T$_{SCM}$ by the frequency of Pentamer Duplication in T$_{EM}$ at years 3-4. A sparse linear multivariate model was built to predict reservoir decay. The multivariate regression model predicting the best reservoir decay contained three features: CD45RA$^{int}$RO$^{int}$ T$_{SCM}$ cell counts at years 3-4 (z-axis), log 10 Pentamer Duplication levels in CD45RA$^{int}$RO$^{int}$ T$_{SCM}$ at years 3-4 (x-axis), and Ratio Pentamer Duplication CD45RA$^{int}$RO$^{int}$ T$_{SCM}$/T$_{EM}$ at years 3-4 (y-axis). Each dot in the scatter plot corresponds to a participant with dot size proportional to the HIV DNA day 720/BL ratio, with a greater decay symbolized by a smaller dot size.

A Novel Memory Stem Cell-Like CD4+ T Cell Subset Contributes to Restoration of T Cell Homeostasis and Correlates with Reservoir Decay To investigate the mechanisms leading to the reconstitution of CD4+ T cells, a longitudinal analysis of the distribution of CD4+ T cell subsets post infusion was performed. Our study showed the specific increase of T cells expressing intermediate levels of CD45RA and CD45RO (termed "CD45RA$^{int}$RO$^{int}$") (FIG. 3A). CD45RA$^{int}$RO$^{int}$ cells were present in the SB-728-T products, were highly enriched in CCR5 gene edited alleles and significantly increased in absolute numbers at every time point analyzed post infusion. Importantly, changes in CD45RA$^{int}$RO$^{int}$ cell counts post infusion, but not of other memory subsets, significantly correlated with long-term increases of CD4+ T cell counts (Table 1). The frequency of CD95+CD58+ cells (markers expressed in T$_{SCM}$ within the CD45RA$^{int}$RO$^{int}$ and CD45RA$^{+}$RO$^{-}$ subsets correlated positively with expansion of CCR5 gene edited cells. Levels of the Pentamer Duplication marker (a sequence tag of CCR5 gene edited cells) were specifically enriched within CD45RA$^{int}$RO$^{int}$ CD95+ cells (referred to as CD45RA "(RO$^{int}$ T$_{SCM}$) and CD45RA$^{+}$ RO$^{-}$ CD95+ cells (referred to as CD45RA$^{+}$ T$_{SCM}$) with approximately 14- and 21-fold higher levels in CD45RA$^{int}$RO$^{int}$ T$_{SCM}$ compared to central memory (T$_{CM}$) or transitional memory (T$_{TM}$) cells at years 3-4; respectively (FIG. 3B). Sequencing of gene editing driven CCR5 DNA mutations confirmed the long-term enrichment of CCR5 gene edited alleles in CD45RA$^{int}$RO$^{int}$ T$_{SCM}$ (range of 14.4% to 37.7% compared to a range of 2.5% to 16.7% in T$_{CM}$. 1% to 16.7% in Try, and 0.7% to 2.59% in T$_{EM}$). Of note, the diversity of these mutations did not vary in CD45RA$^{int}$RO$^{int}$ T$_{SCM}$ between SB-728-T products and year 3-4 time point samples indicating that these cells most likely represent a long-lived memory subset that contributes to the long-term polyclonal persistence of CCR5 gene edited cells. Moreover, the persistence of CD45RA$^{int}$RO$^{int}$ T$_{SCM}$ but not that of CD45RA$^{int}$RO$^{int}$ CD95- or CD45RA$^{+}$ T$_{SCM}$ cells at year 3-4 time points significantly correlated with increased total CD4+ T cell counts (Table 1). Altogether, these results indicate that infusion of SB-728-T leads to a novel T$_{SCM}$-like subset that is associated with long term persistence of CCR5 gene mutations and reconstitution of CD4+ T cells.

TABLE 1

Correlation of increase in circulating CD4+ T cell subsets
(delta cell count) at early (day 14), mid (month 4-7),
late (month 11-12) and long-term time points
(years 3-4) with immune reconstitution (delta CD4+
count) at the same time points.

| | | Shearman's rho ρ | P value | q value (FDR) | n |
|---|---|---|---|---|---|
| Delta CD4+ count (cell/μL) days 14-28 | Delta T$_{CM}$ (cell/μL) d14-28 | 0.9429 | 0.0167 | 0.0417 | 6 |
| | Delta T$_{TM}$ (cell/μL) d14-28 | 1 | 0.0028 | 0.0139 | 6 |
| Delta CD4+ count (cell/μL) months 4-7 | Delta T$_{CM}$ (cell/μL) m4-7 | 0.8333 | 0.0154 | 0.0769 | 8 |
| | Delta T$_{TM}$ (cell/μL) m4-7 | 0.7619 | 0.0368 | 0.0867 | 8 |
| Delta CD4+ count (cell/μL) months 11-12 | Delta T$_{CM}$ (cell/μL) m11-12 | 0.9 | 0.0255 | 0.0101 | 9 |
| | Delta T$_{TM}$ (cell/μL) m11-12 | 0.75 | 0.0255 | 0.0319 | 9 |
| | Delta Total CD45RA$^{int}$RO$^{int}$ (cell/μL) m11-12 | 0.8667 | 0.0045 | 0.0113 | 9 |
| Delta CD4+ | Delta Total CD45RA$^{int}$RO$^{int}$ (cell/μL) yr3-4 | 0.8870 | 0.0014 | 0.0143 | 9 |

TABLE 1-continued

Correlation of increase in circulating CD4+ T cell subsets
(delta cell count) at early (day 14), mid (month 4-7),
late (month 11-12) and long-term time points
(years 3-4) with immune reconstitution (delta CD4+
count) at the same time points.

| | | Shearman's rho ρ | P value | q value (FDR) | n |
|---|---|---|---|---|---|
| count (cell/μL) years 3-4 | Delta CD45RA$^{int}$RO$^{int}$ T$_{SCM}$ (cell/μL) yr3-4 | 0.8857 | 0.0333 | 0.1417 | 6 |
| | Delta RA$^{int}$RO$^{int}$ CD95$^-$ | 0.1429 | 0.8028 | | 6 |
| | Delta RA$^{+}$RO$^{-}$ CD95+ | 0.7143 | 0.1361 | | 6 |
| | Delta RA$^{+}$RO$^{-}$ CD95– | –0.2000 | 0.7139 | | 6 |

T$_{CM}$ cells are defined as CD45RA_, CD45RO$_+$, CCR97$_+$, and CD27$_+$
T$_{TM}$ cells are defined as CD45RA_, CD45RO$_+$, CCR79_, and CD27$_+$
CD45RA$_{int}$RO$_{int}$ T$_{SCM}$ are defined as CD45RA$_{int}$, CD495RO$_{int}$, CCR7$_+$, CD27$_+$, CD127$_+$, CD28$_+$, CD58$_+$, and CD95 Results are shown only for significant correlations with P < 0.05 and false discovery rate (FDR) < 0.25

Figure 3C:
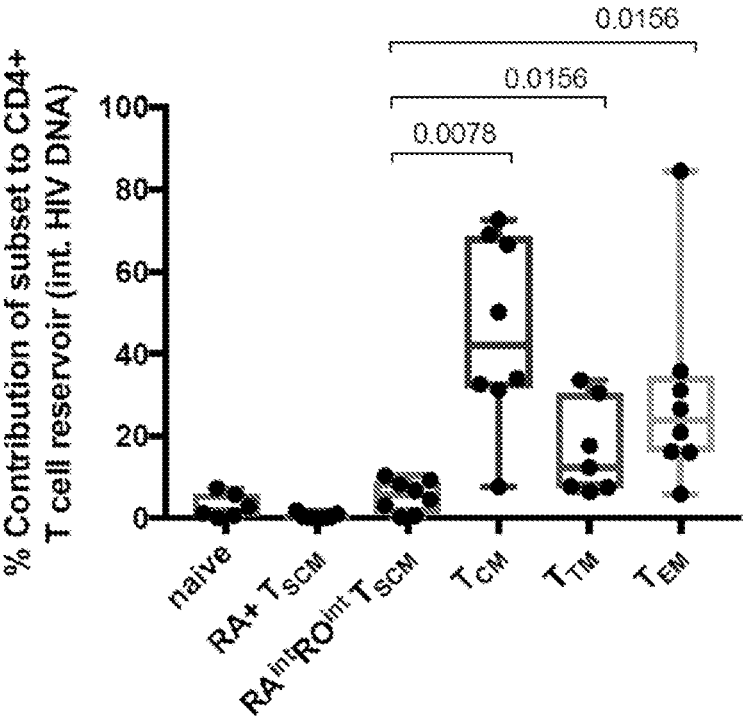

The presence of CCR5 gene mutations in short-lived memory cells such as T$_{EM}$ at years 3-4 post infusion (FIG. 3B) suggests that CCR5 gene edited cells within long-lived memory cells such as T$_{SCM}$ and T$_{CM}$ are differentiating into T$_{EM}$ resulting in maintenance of a small subset of CCR5 gene edited T$_{EM}$ cells up to 3-4 yrs post infusion. To investigate the role of CD45RAW RO$^{int}$ T$_{SCM}$ on the decay of the HIV reservoir, we first quantified levels of integrated HIV DNA in SB-728-T products and at year 3-4 samples in CD4+ T cell subsets and found that CD45RA$^{int}$RO$^{int}$ T$_{SCM}$ cells had significantly lower levels of integrated HIV DNA compared to other memory subsets (1.99 log 10, 95% CI: 1.64-2.34 in CD45RA$^{int}$RO$^{int}$ T$_{SCM}$ at years 3-4 vs. 2.8 log 10, 95% CI; 2.48-3.13 in T$_{CM}$ P=0.016, 2.79 log 10 95% CI: 2.31-3.28 in T$_{TM}$ P=0.016, 2.87 log 10 95% CI: 2.28-3.45 in T$_{EM}$ P=0.023). Moreover, only 5.3% of CD45RA$^{int}$RO$^{int}$ T$_{SCM}$ cells contributed to the CD4+ T cell HIV reservoir in year 3-4 samples, (FIG. 3c) whereas other memory subsets contributed significantly higher frequencies of cells to the pool of cell with HIV tot DNA [45.5% for T$_{CM}$ (P=0.0078). 16.5% for T$_{TM}$ (P=0.0156), and 29.6% for T$_{EM}$ (P=0.0156)].

Figure 3D:
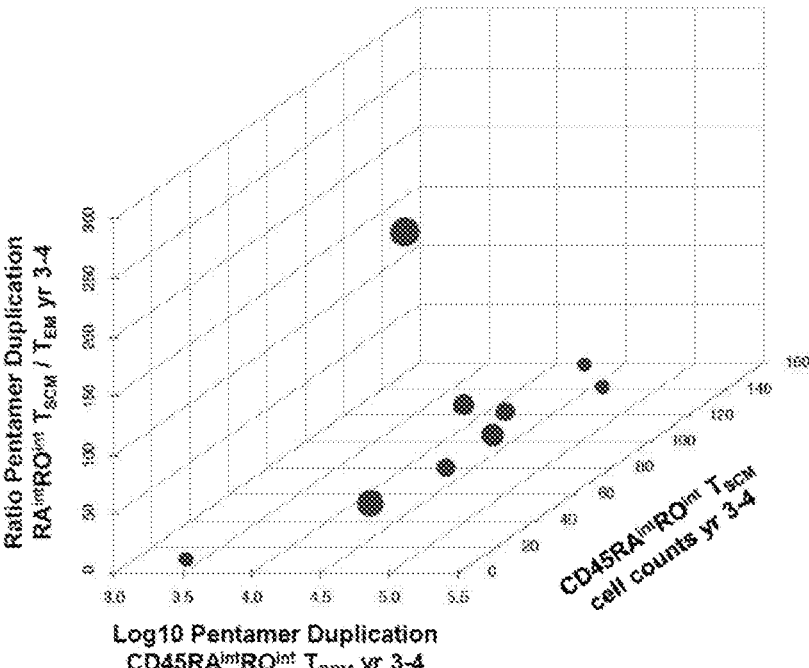

Differentiation of CD45RA$^{int}$RO$^{int}$ T$_{SCM}$ cells that harbor low levels of integrated HIV DNA into other memory subsets could provide a mechanism underlying the decay of the HIV reservoir in total CD4+ T cells. To investigate this, a sparse linear multivariate model was built to predict the change in the frequency of PBMCs harboring total HIV DNA post infusion that included CD45RA$^{int}$RO$^{int}$ T$_{SCM}$ cell counts, the frequency of Pentamer Duplication in CD45RA$^{int}$RO$^{int}$ T$_{SCM}$ cells as well as the number of shared mutations between CD45RA$^{int}$RO$^{int}$ T$_{SCM}$ and T$_{EM}$ as possible independent variables. Our analysis indicated that a greater decay in the HIV reservoir post infusion was best predicted by higher CD45RA$^{int}$RO$^{int}$ T$_{SCM}$ cell counts at yr 3-4 (P=0.0018), higher frequency of Pentamer Duplication in CD45RA$^{int}$RO$^{int}$ T$_{SCM}$ at yr 3-4 (P=0.005), and lower ratio of the frequency of Pentamer Duplication in CD45RA RO$^{int}$ T$_{SCM}$ by the frequency of Pentamer Duplication in T$_{EM}$ at years 3-4 ((P=0.0014) (adjusted R2=0.99, F-test: P=0.0008; FIG. 3D). These results demonstrate that long-term persistence of CD45RA$^{int}$RO$^{int}$ T$_{SCM}$ cell counts and maintenance of a subset of CCR5 gene edited cells within the T$_{EM}$ population is important for reduction of the HIV reservoir, and suggest that CD45RA$^{int}$RO$^{int}$ Tsc cells can differentiate into, and replenish the pool of more differentiated memory cells with a detectable proportion of cells harboring CCR5 gene edited alleles that would be resistant to infection.

CD45RA$^{int}$RO$^{int}$ T$_{SCM}$ Express Genes Associated with Quiescence and Self-Renewal and can Differentiate into Other Memory Subsets Our results demonstrating the persistence of CD45RA$^{int}$RO$^{int}$ T$_{SCM}$ and their impact on long-term CD4+ T cell reconstitution suggested that these cells express genes and pathways that confer long-term persistence. Transcriptional analysis of sorted CD4+ T cell subsets was performed on samples from 3-4 years post infusion. Multi-dimensional scaling of gene expression variance showed greater dissimilarity between CD45RA$^{int}$RO$^{int}$ T$_{SCM}$ and T$_{CM}$ and T$_{EM}$ than with CD45RA$^+$ T$_{SCM}$. In addition, a larger number of differentially expressed genes (DEGs) was found when comparing CD45RA$^+$ T$_{SCM}$ to T$_{EM}$ than to Tom and CD45RA$^+$ T$_{SCM}$ (5022 vs. 2943, vs. 2136). Gene Set Enrichment Analysis (GSEA) showed that CD45RA$^{int}$RO$^{int}$ T$_{SCM}$ cells were enriched in genes involved in stemness (such as the Notch signaling pathway, required for Wnt-mediated maintenance of undifferentiated HSCs) and in metabolic pathways that contribute to cell persistence such as fatty acid oxidation, oxidative phosphorylation and pyruvate metabolism. Genes associated with apoptosis, effector function, cell cycle, and JAK-STAT signaling were down-regulated when compared to both Tom and T$_{EM}$ (FIG. 4A), suggesting that CD45RA$^{int}$RO$^{int}$ T$_{SCM}$ cells are more quiescent than other memory subsets.

To assess the capacity of CD45RA$^{int}$RO$^{int}$ T$_{SCM}$ to differentiate into other memory subsets, we sequenced the CCR5 ZFN mediated mutations in sorted CD4+ T cell subsets and identified sequences that were unique to CD45RA$^{int}$RO$^{int}$ T$_{SCM}$ cells in SB-728-T products (n=3, 881). Distribution analysis of these sequences 3-4 years post infusion in the various CD4+ T cell memory subsets (FIG. 4B) showed that CD45RA$^{int}$RO$^{int}$ T$_{SCM}$-unique mutations were detected in all memory T cell subsets including short-lived T$_{EM}$ (0.49% (95% CI: 0%-1.36%). These results demonstrate that CD45RA "(RO$^{int}$ T$_{SCM}$ cells can differentiate into and replenish the pool of more differentiated memory cells. To further characterize the differentiation status of CD45RA$^{int}$RO$^{int}$ T$_{SCM}$ compared to other memory subsets, we investigated by flow cytometry their polyfunctional response following stimulation with anti-CD3/28 coated beads (FIG. 4c), SEB or PMA/Ionomycin. Our analysis placed the CD4+CD45RA$^{int}$RO$^{int}$ T$_{SCM}$ cells as less differentiated than T$_{CM}$ T$_{TM}$, and T$_{EM}$. The undifferentiated status of CD45RA$^{int}$RO$^{int}$ T$_{SCM}$ cells was confirmed by analyzing the expression levels of transcription factors associated with Th1 (T-bet and Eomes), Th2 (GATA-3) and Th17 (RORgt) lineage commitment. Similar to naïve cells and CD45RA+ T$_{SCM}$, CD45RA$^{int}$RO$^{int}$ T$_{SCM}$ cells did not express Th-specific transcription factors (FIG. 3d). Further analysis of immune checkpoint markers showed that CD45RA$^{int}$ (RO$^{int}$ CD95+ cells have significantly lower levels of PD-1, TIGIT, and SLAM than T$_{TM}$ and T$_{EM}$ suggesting that CD45RA$^{int}$RO$^{int}$ CD95+ cells are less exhausted than other memory subsets (FIG. 28B). Altogether, these results indicate that CD45RA$^{int}$RO$^{int}$ T$_{SCM}$ exhibit stem cell properties that include longevity and multipotency and are precursors to the more differentiated than T$_{CM}$, T$_{EM}$ and T$_{EM}$ memory cells.

Figure 4E:
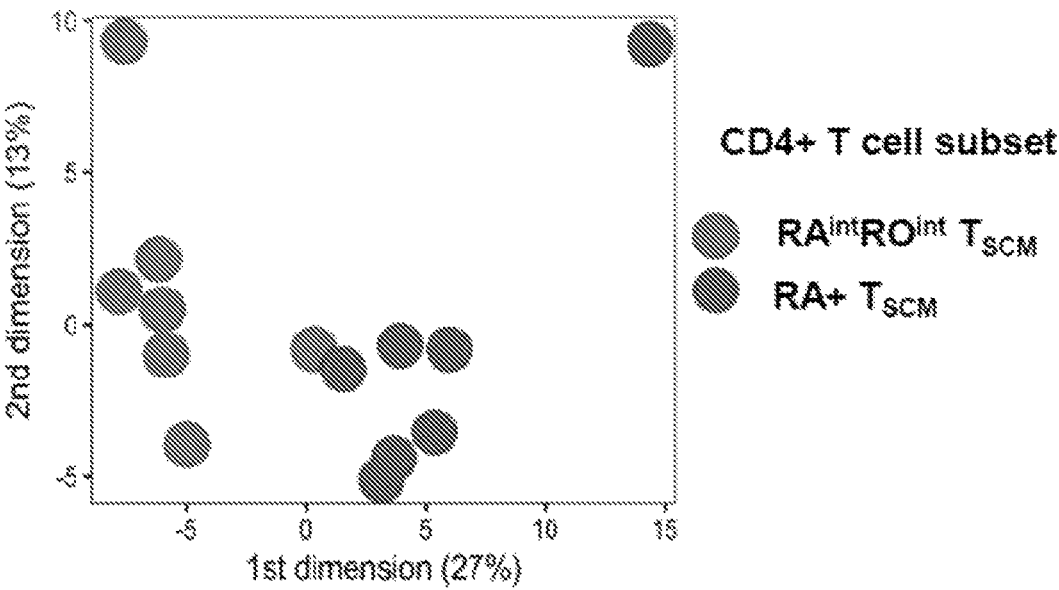
Figure 4F:
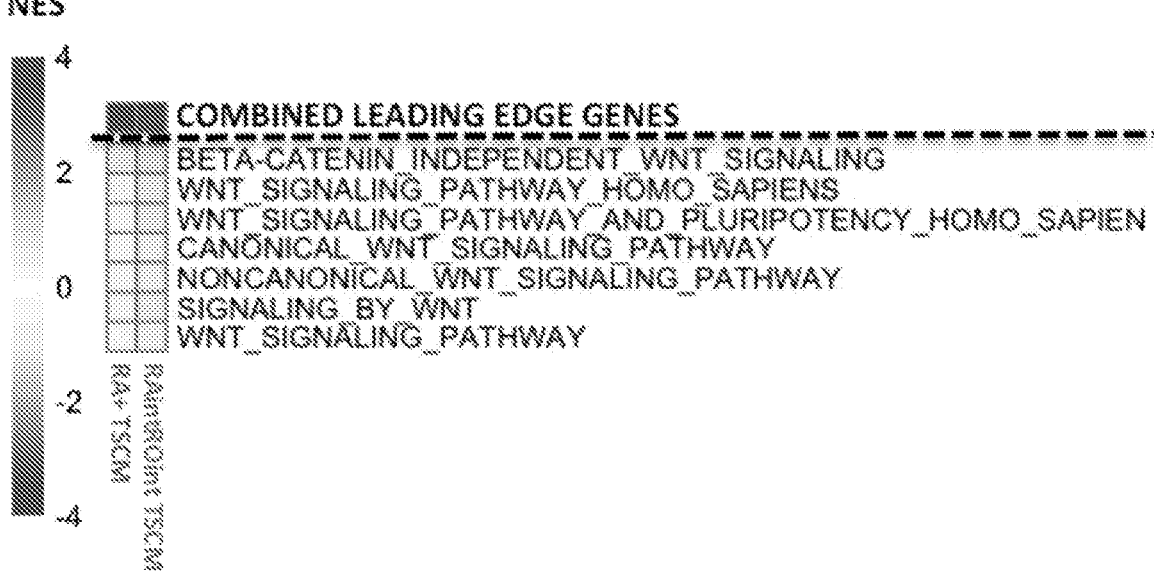
Figure 4G:
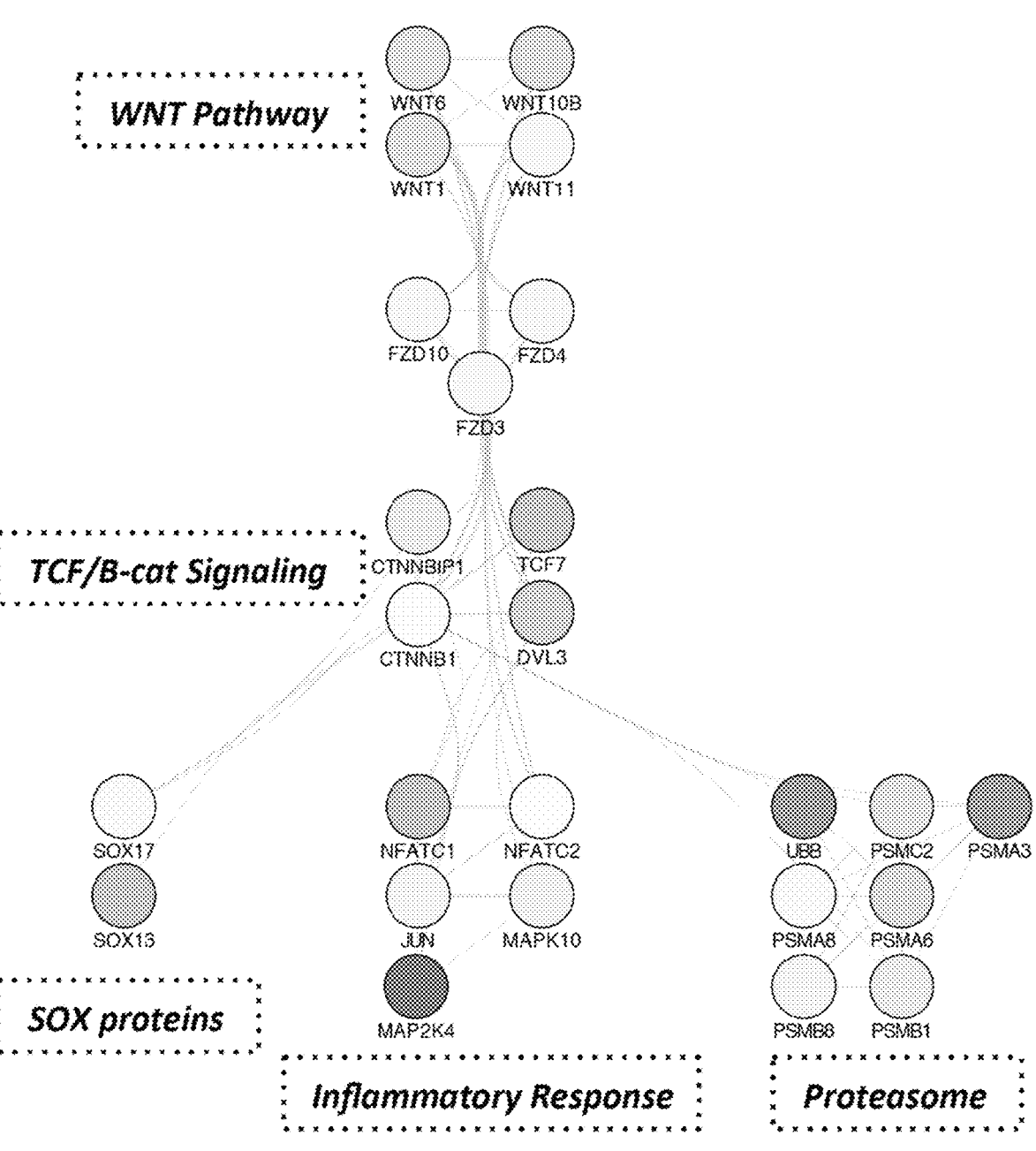

We next compared the transcriptomes of CD45RA$^{int}$RO$^{int}$ T$_{SCM}$ and CD45RA+T$_{SCM}$ cells to investigate differences in gene expression and specifically of pathways involved in self-renewal including Wnt-signaling cascade (FIG. 4F)-a pathway implicated in maintaining the "stem-like" phenotype of T cells. Multi-dimensional scaling of gene expression variance showed that the previously characterized CD45RA+CD95+T memory stem cells (T$_{SCM}$) were transcriptionally distinct from the CD45RA$^{int}$RO$^{int}$ T$_{SCM}$ population described in this study (FIG. 4E). A closer look at the combined leading-edge genes of these genesets revealed upregulation in expression of several genes that are crucial to maintain stemness. These included Wnt factors and their receptors (Frizzled—FZDs)—which as indicated above are known to initiate stem-ness maintenance cascade (FIG. 4G). This was coupled with downstream signaling cascade that included DVLs, beta-catenin and TCF7-genes known to prevent effector T cell differentiation. Further downstream mechanisms of stemness defined by upregulation of SOX genes was also observed (FIG. 4g). Interestingly, CD45RA$^{int}$RO$^{int}$ T$_{SCM}$ was enriched in pro-inflammatory (MAPKs, Jun, NFATs) and apoptotic (PSMs) genesets when compared to their CD45RA$^+$ T$_{SCM}$ counterpart (FIG. 4G). The enhancement of pro-inflammatory signatures in this subset could point to an increase in their ability to differentiate into more "effector" like cells. Interestingly, the combined leading-edge genes associated with the Wnt-signaling cascade were positively correlated with the long-term increases in CD4+ T cell counts and negatively correlated with the reduction of the HIV reservoir post infusion.

All together, these results confirm that cells of the CD45RA$^{int}$RO$^{int}$ T$_{SCM}$ phenotype constitute a novel and distinct T$_{SCM}$ subset that have features of long-lived and undifferentiated memory cells.

The Frequencies of CCR5 Gene Edited CD45RA$^{int}$RO$^{int}$ T$_{SCM}$ Correlate with Control of Viral Load in Participants Who Underwent Treatment Interruption 6 Weeks Post SB-728-T Infusion We next assessed the impact of infusion of CCR5 gene edited CD4+ T cells, including CD45RA$^{int}$RO$^{int}$ T$_{SCM}$, on control of viremia upon cessation of ART treatment. We analyzed samples from an independent clinical trial (SB-728-1101 study; n=15; 5 cohorts; see Material and Methods) in which participants underwent an analytical treatment interruption (ATI) at six weeks post infusion of SB-728-T products. Analysis of viral load levels showed significantly lower viral loads during ATI (at week 22) than their historic pre-ART viral load set point (P=0.0067) (FIG. 5A), indicating that infusion of SB-728-T products may have led to transient but incomplete control of viremia in the majority of the participants. ATI was extended in six individuals that showed viral load measurements below 10,000 copies/mL and CD4+ T cell counts above 500 cells/μl at week 22 who then spent 0.5-2 years on ATI. Viral load at month 12 for the 5 participants that remained on ATI at that time point ranged from 130 to 16,000 copies/mL. One of these individuals (01-060) had a protective human leukocyte antigen (HLA) allele; HLA-B57.

Figure 5A:
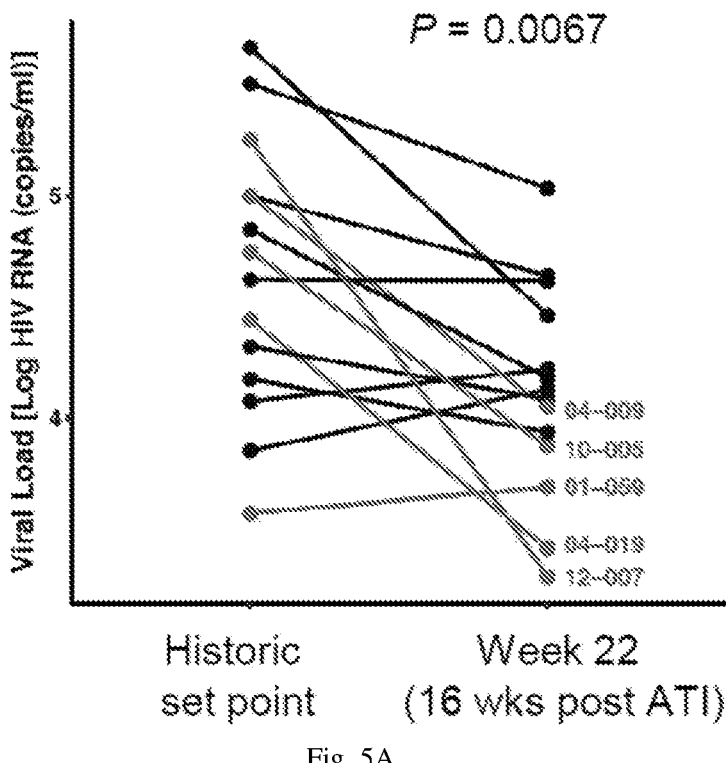
Figure 5B:
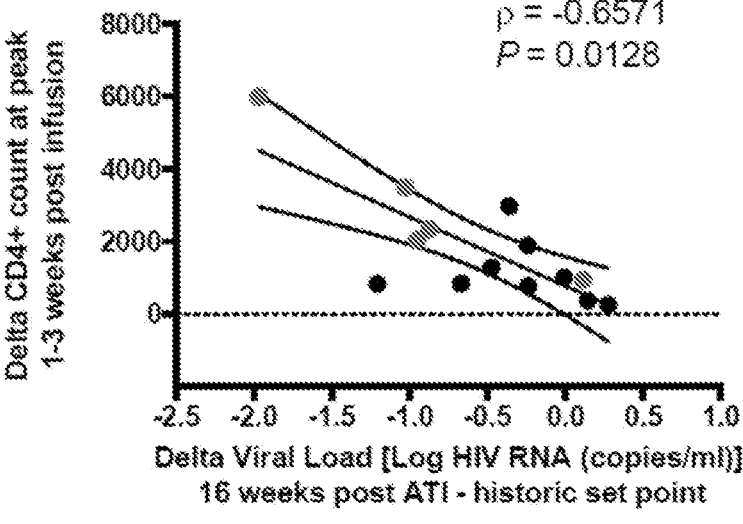
Figure 5C:
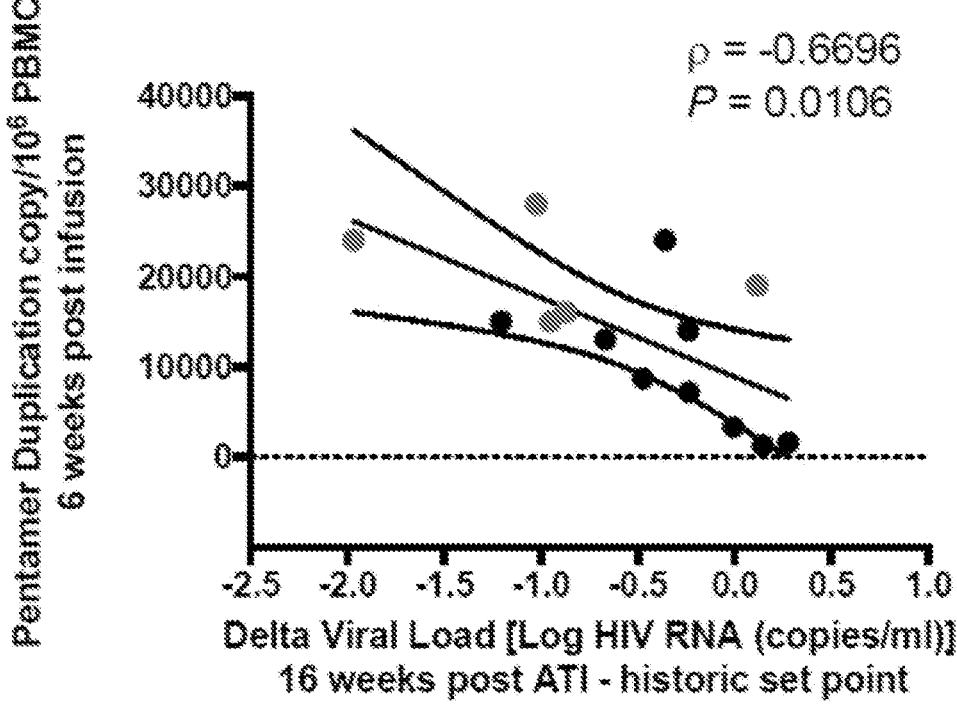
Figure 5D:
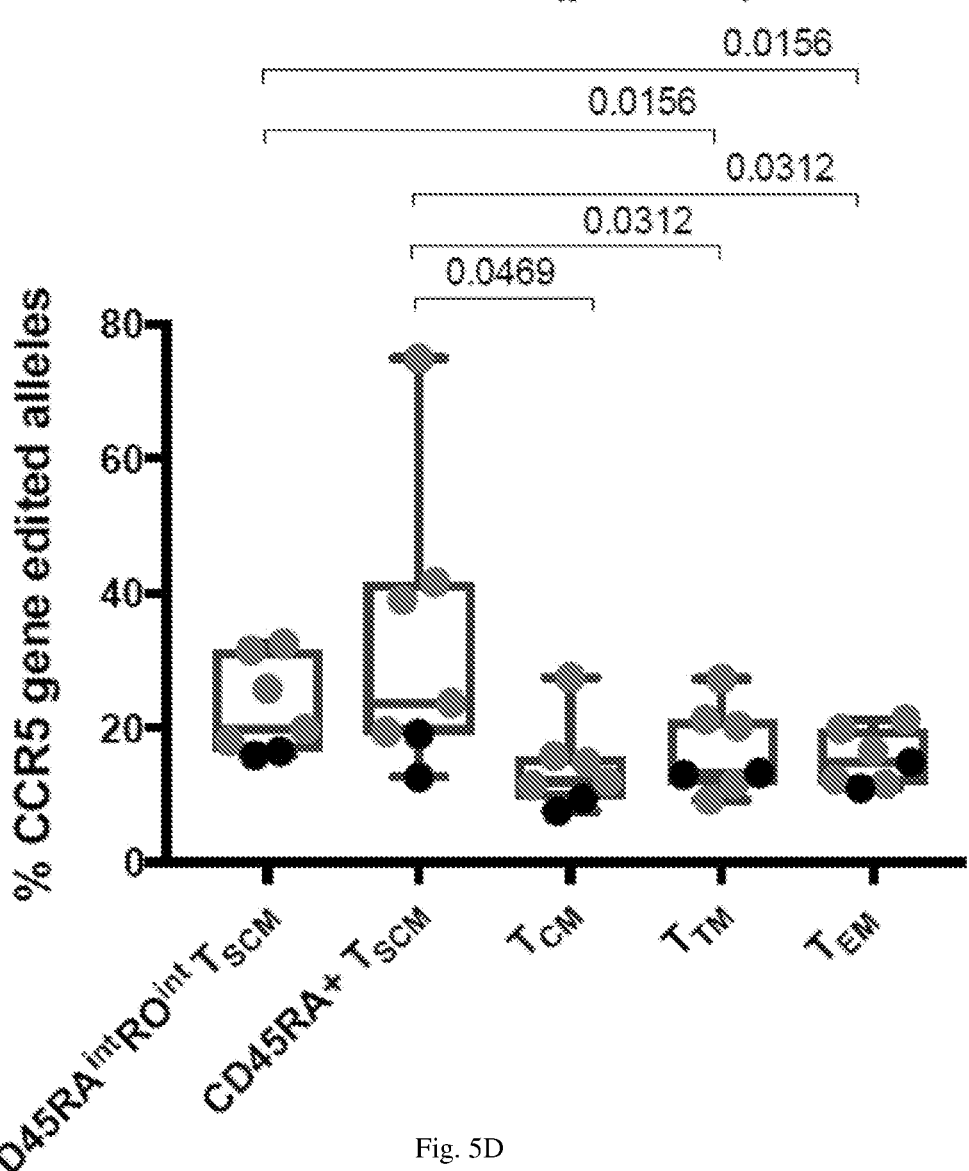
Figure 5E:
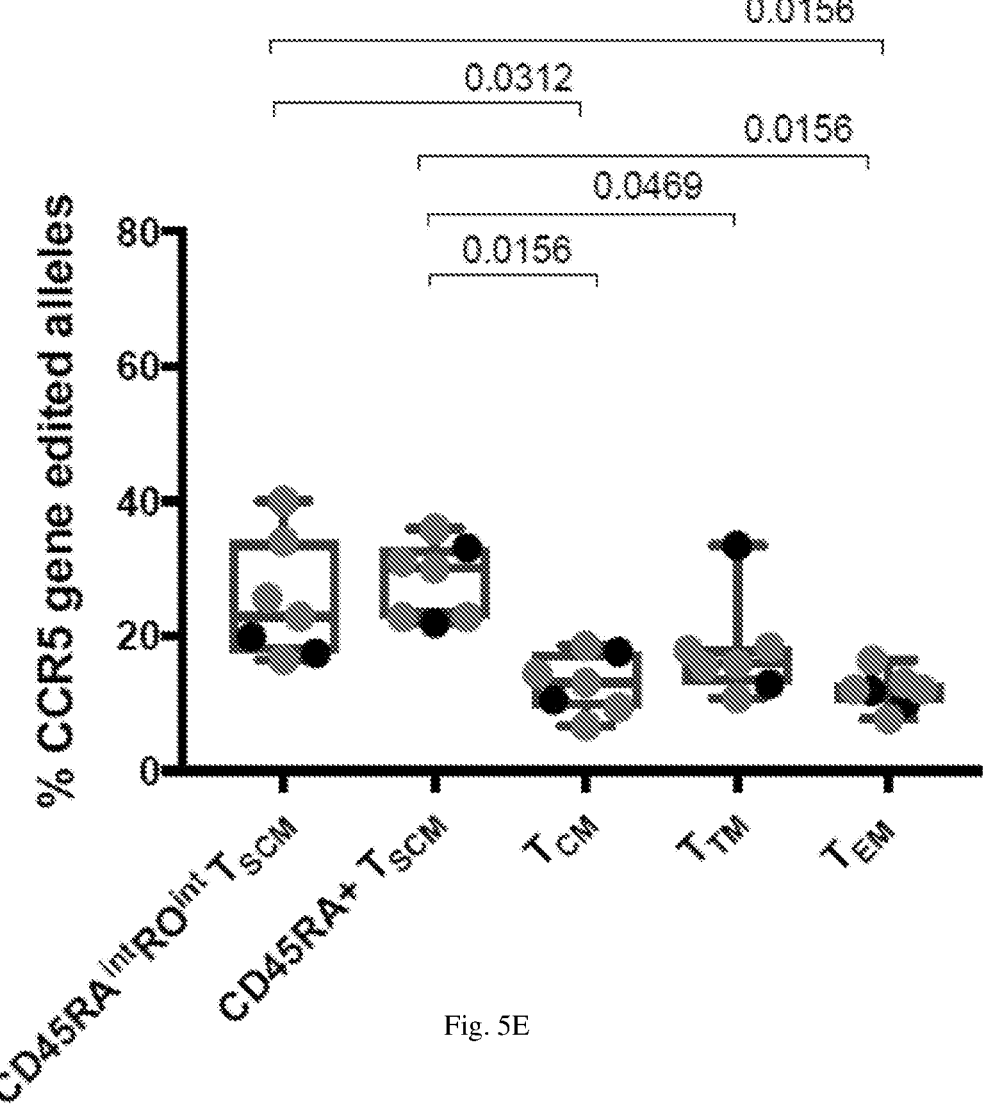
Figure 5F:
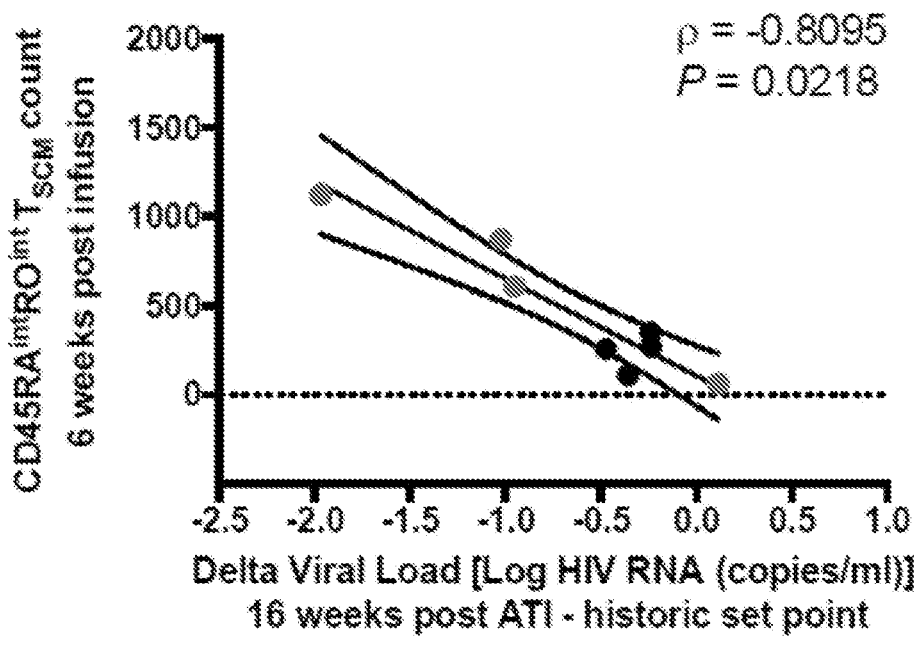
Figure 5G:
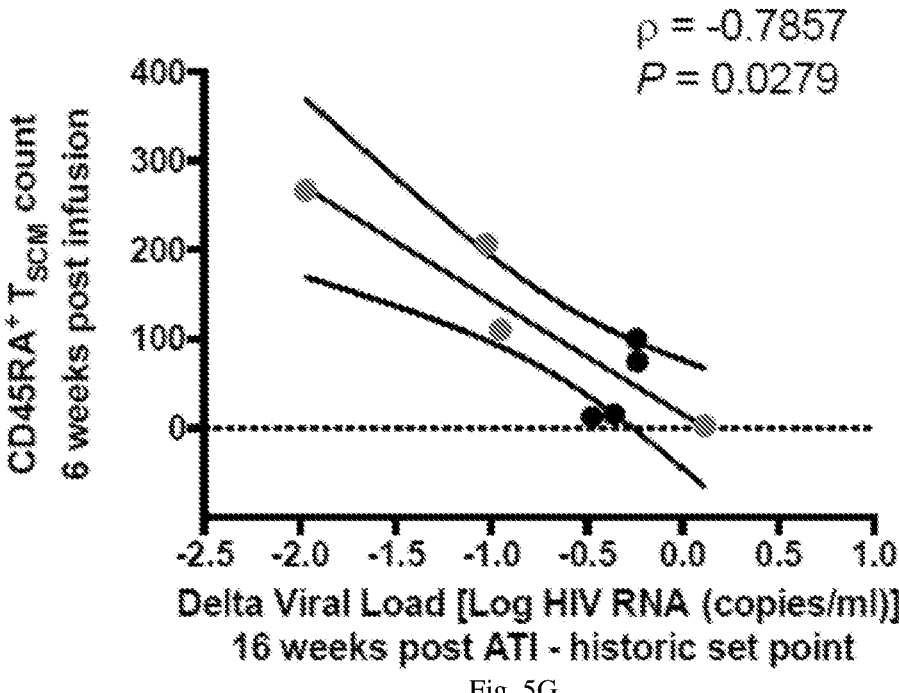

Coincidentally, a larger reduction of week 22 viral load compared to the historic pre-ART viral load set point correlated significantly with a greater change in CD4+ T cell counts at peak cell expansion (FIG. 5B) and with higher frequencies of CCR5 gene edited alleles prior to ATI (week 6) (FIG. 5C). These results highlight the association between expansion of CCR5 gene edited cells upon SB-728-T infusion and control of viral load, suggesting a role for the T$_{SCM}$ subsets, shown to also be enriched in CCR5 gene mutation in the 1101 trial (FIG. 5d, c), in the reduction of viral load post ATI. Correlation analysis between control of viral load and CD4+ T cell subset counts indicated that only higher CD45RA "RO$^{int}$ T$_{SCM}$ and CD45RA+RO T$_{SCM}$ cell counts (and specifically CCR5 gene edited T$_{SCM}$ cell counts) prior to ATI (week 6) correlated with a larger reduction of week 22 viral load compared to the historic viral load set point (FIG. 5F, G).

Figure 5H:
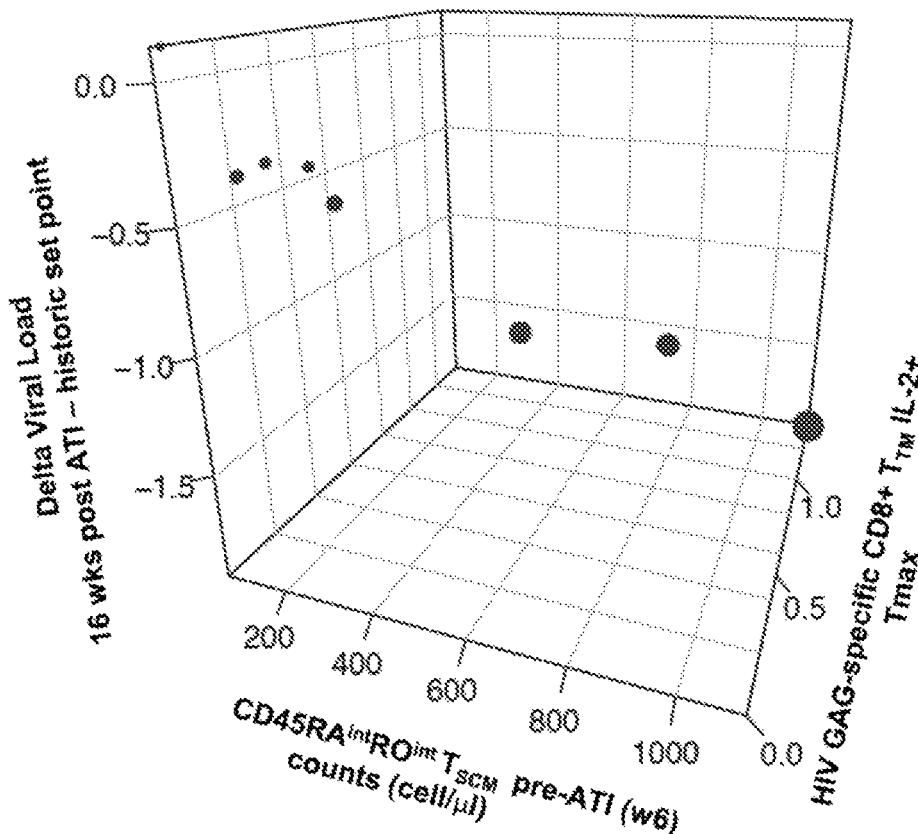

We next investigated the functional response of HIV-specific CD8+ T cells, previously shown to exert a critical role on the control of viral replication (REFS), post ATI and built a multivariate regression model to predict the change in viral load at week 22 compared to historic pre-ART viral load set point using the peak frequency of cytokine (IFN-γ. TNF-α, IL-2) production by HIV-specific CD8+ T cell subsets post ATI as well as the CD45RA$^{int}$RO$^{int}$ T$_{SCM}$ counts prior to ATI (week 6). Our analysis indicated that reduction in viral load at week 22 relative to historic pre-ART set point was best predicted by higher CD45RA$^{int}$RO$^{int}$ T$_{SCM}$ cell counts prior to ATI together with the peak frequency of CD8+ TIM cells producing IL-2, explaining 95% of the change in viral load (FIG. 5H). These results demonstrate that the decay in the HIV reservoir is significantly and negatively associated to the expansion of CD45RA$^{int}$RO$^{int}$ T$_{SCM}$ cells (p=0.05) and CD8+ T$_{TM}$ cells producing IL-2 (P=0.02).

The Frequencies of CCR5 Gene Edited T$_{EM}$ Correlate with Control of Viral Load in Participants Who Underwent Treatment Interruption 6 Weeks Post SB-728-T Infusion To test the hypothesis that CCR5-gene edited CD45RA "(RO$^{int}$ T$_{SCM}$ cells contribute to the control of viral load through differentiation into other memory subsets during ATI, we first identified CCR5 mutations unique to CD45RA$^{int}$RO$^{int}$ T$_{SCM}$ products and tracked their persistence in other memory cells post infusion and post ATI. Our results show that CCR5 mutations unique to CD45RA$^{int}$RO$^{int}$ T$_{SCM}$ products were detected in all CD4+ memory subsets at weeks 6 and 22 (add freq. numbers, FIG. 6A), highlighting the potential of CCR5-gene edited CD45RA$^{int}$RO$^{int}$ T$_{SCM}$ cells to differentiate.

Figures 6A, 6B:
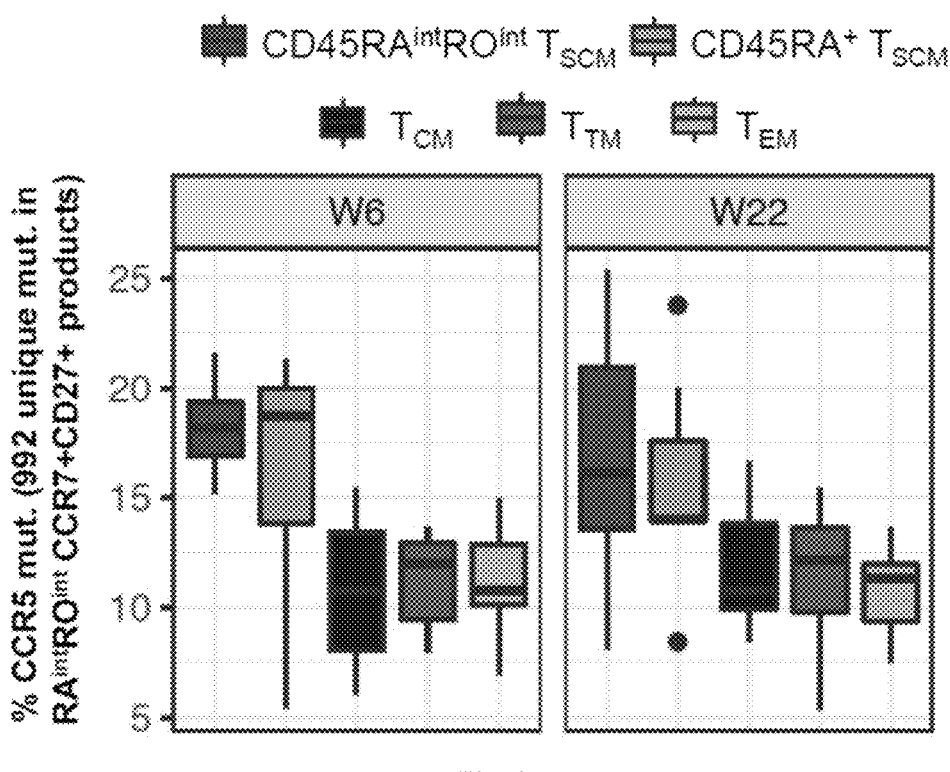

To investigate the impact of long term viral replication on the persistence and differentiation capacity of CCR5-gene edited CD4+ T-cell memory subsets, we next modelled the homeostasis of CCR5-gene edited and unedited CD4+ T-cell subsets during viremia (week 6 to month 12) in the 5 individuals for whom ATI was extended until month 12 or beyond using an ordinary differential equation model. Using an individual fitting routine in Monolix, the death (Y), proliferation (p), and transition (Q) rates (cell/day) were obtained for each CCR5-gene edited and unedited CD4+ T-cell subset. We observed that the death rates of the CCR5-gene edited CD45RA$^+$ T$_{SCM}$, CD45RA$^{int}$RO$^{int}$ T$_{SCM}$, and T$_{CM}$ memory CD4+ T-cells are on average 3 magnitudes lower compared to the death rates of the unedited counterparts (FIG. 6B). In addition, the death rates of the CCR5 gene edited CD45RA$^+$ T$_{SCM}$, CD45RA$^{int}$RO$^{int}$ T$_{SCM}$, and Tom memory CD4+ T-cells were lower than their transition rates (FIG. 6B). Moreover, using a sensitivity analysis test in Matlab to identify the relationships between the parameters and cell counts, we observed that the model parameter of transition had a significant negative correlation with the CCR5-gene edited CD45RA$^+$ T$_{SCM}$. CD45RA$^{int}$RO$^{int}$ T$_{SCM}$, and Tc cell counts post ATI (FIG. 6B). Altogether, these results suggest that the presence of CCR5 mutations has a protective effect on the CD4+ early memory subsets and that loss of these cells overtime is much more likely to be due to differentiation of these cells than cell death. In addition, sensitivity analysis also showed that the proliferation rates of the CCR5 gene edited CD45RA "(RO$^{int}$ T$_{SCM}$ had a significant positive correlation with the cell counts of all CCR5 gene edited cells, including T$_{EM}$, which was not observed for the proliferation rates of other subsets (FIG.

6B). This suggests that self-renewal of CCR5 gene edited CD45RA "(RO$^{int}$ T$_{SCM}$ is important for replenishment and maintenance of CCR5 mutations in other memory subsets.

Figure 6C:
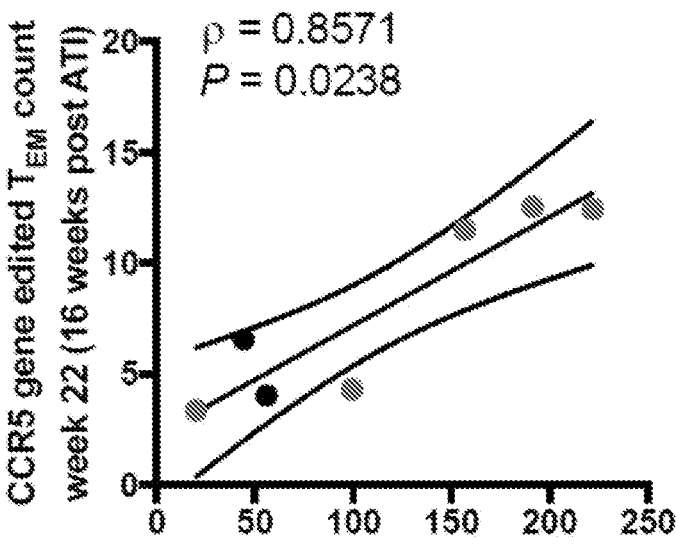
Figure 6D:
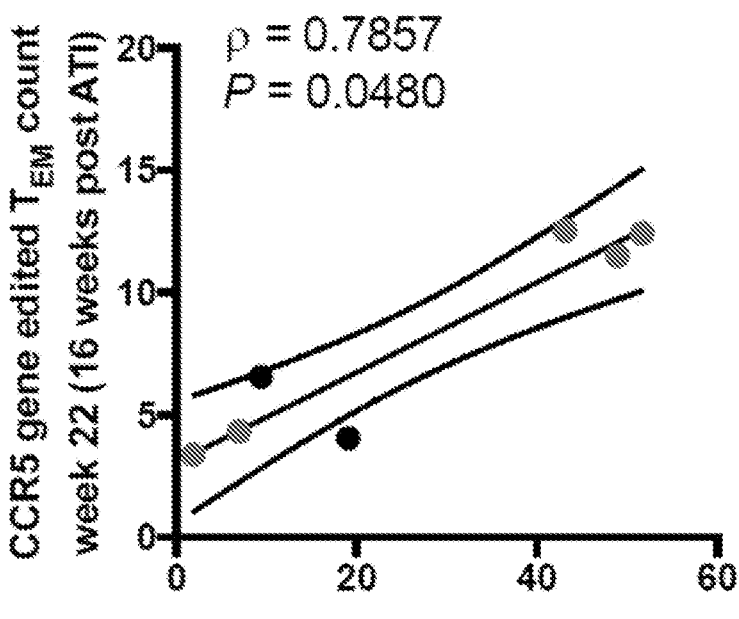
Figure 6E:
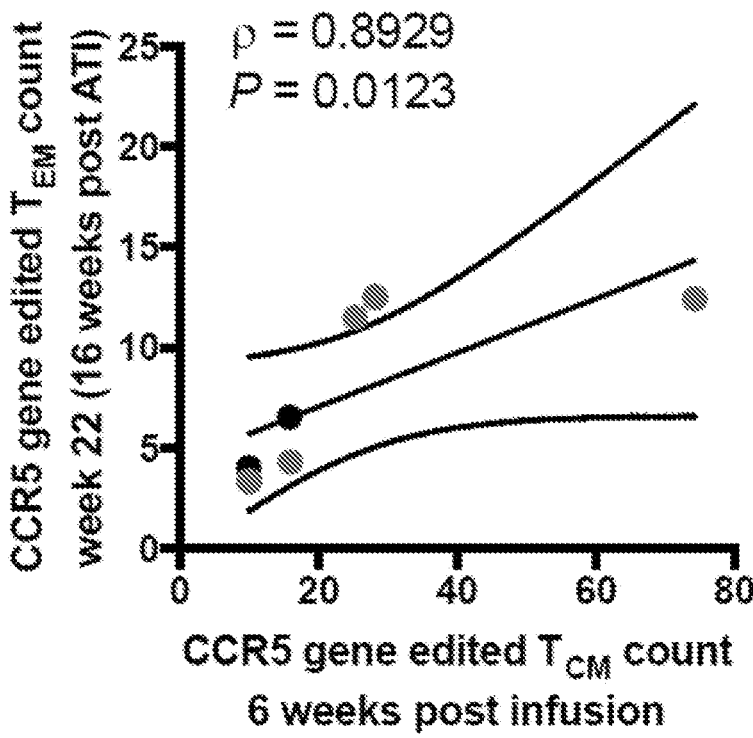

In support of these findings, higher CCR5 gene edited CD45RA+RO T$_{SCM}$. CD45RA$^{int}$RO$^{int}$ T$_{SCM}$ and T$_{CM}$ cell counts prior to ART interruption (week 6) correlated with higher numbers of CCR5 gene edited T$_{EM}$ cells post ATI (week 22), confirming that viremia could trigger the progressive differentiation of T$_{SCM}$ into T$_{EM}$ cells (FIG. 6C-E).

Figure 6F:
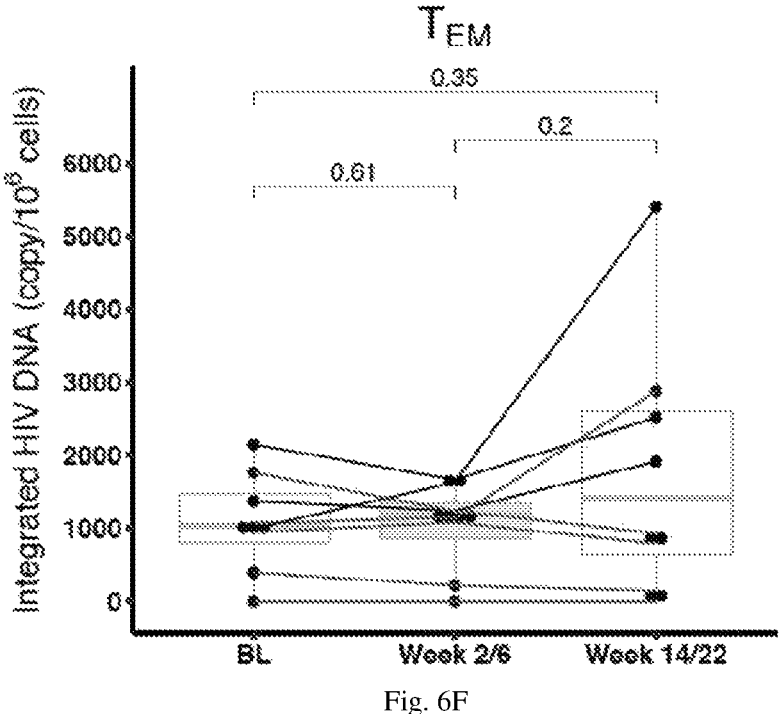
Figure 6G:
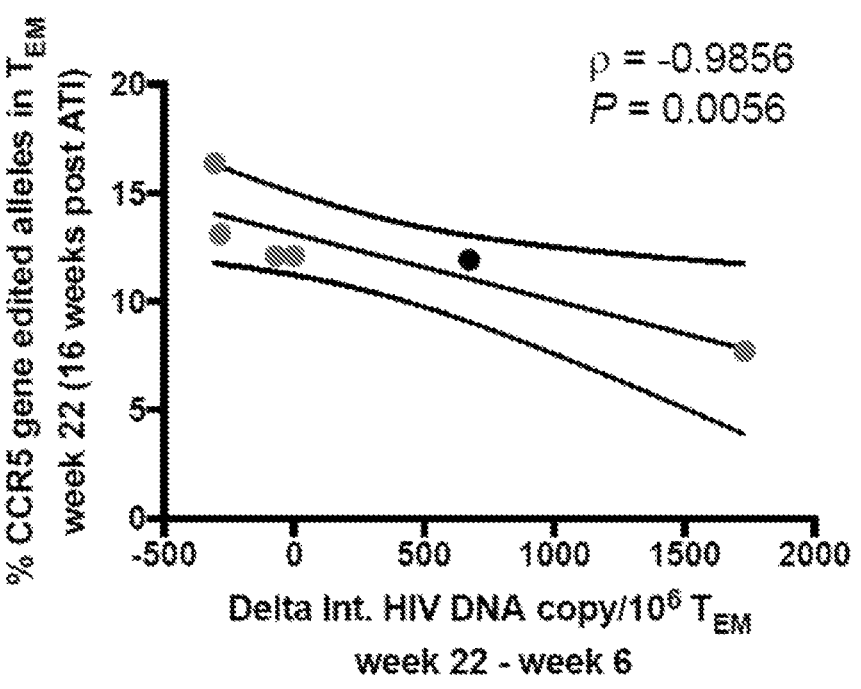
Figure 6H:
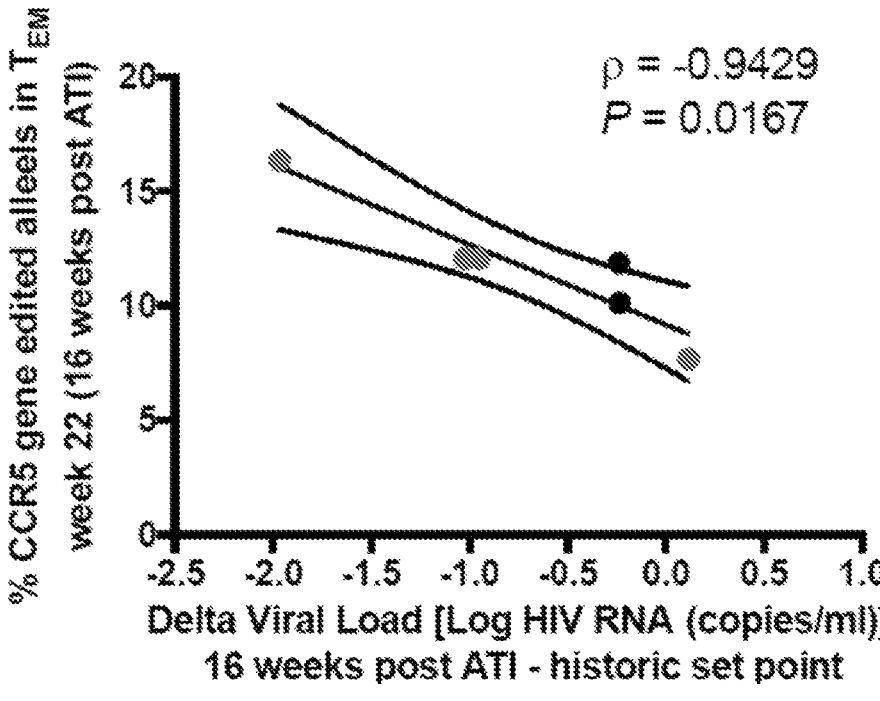
Figure 6I:
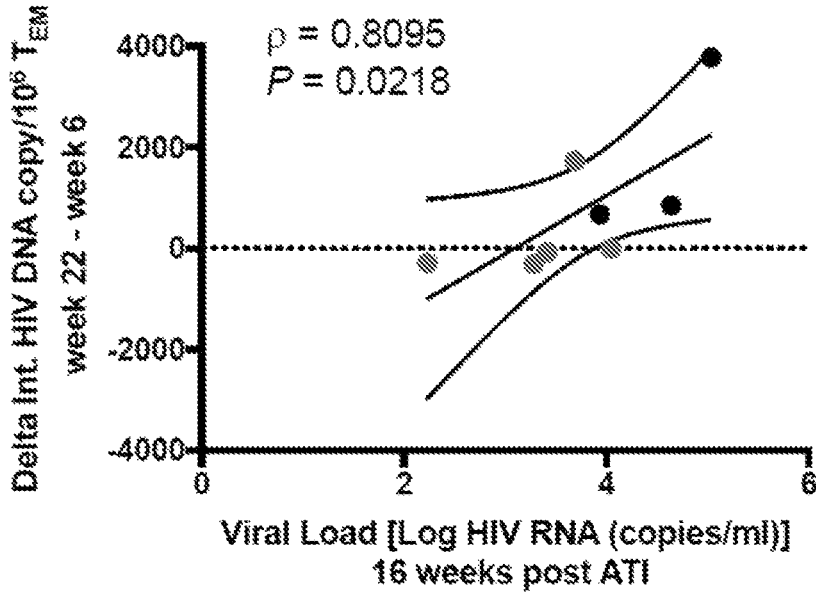

As T$_{EM}$ cells have been shown to express the highest levels of CCR5 compared to other memory cells, maintenance of a subset of CCR5 gene edited cells within the T$_{EM}$ subset during viral replication could lead to protection from de novo infection. To investigate this, we measured the size of the HIV reservoir (as estimated by integrated HIV DNA levels) in sorted CD4+ T cell subsets at baseline, and at weeks 6 and 22 post infusion. Our results indicate that the frequency of T$_{EM}$ bearing integrated HIV DNA did not significantly change during ATI (FIG. 6F). Closer inspection revealed that 50% of the participants analyzed had increased the size of the reservoir in T$_{EM}$ cells between weeks 6 and 22, with the other half showing no change or a decrease in the frequencies of integrated HIV DNA. Importantly, the change in the frequency of cells harboring integrated HIV DNA within T$_{EM}$ cells during ATI inversely correlated with the frequency of CCR5 gene edited alleles in the T$_{EM}$ population (FIG. 6G). We further found that higher frequencies of CCR5 gene edited alleles at week 22 in the T$_{EM}$ subset specifically (and not in other subsets) correlated with a larger decrease in week 22 viral load compared to historic pre-ART viral load set point (FIG. 6H-I). Collectively, these results indicate that continuous replenishment of CCR5 gene edited T$_{EM}$ cells as a consequence of differentiation from their precursors limits the size of the reservoir in T$_{EM}$ during viremia and that greater protection from de novo infection of the T$_{EM}$ subset has an impact on control of active viral replication during ATI.

Observations from this study further substantiate our findings generated from the SB-728-0902 cohort that demonstrate that the novel CD45RA$^{int}$RO$^{int}$ T$_{SCM}$ subset has the highest levels of CCR5 gene edited alleles and is capable of differentiating into other memory subsets. Differentiated memory T cells, including short lived T$_{EM}$ that express CCR5 mutations are protected from viral infection; this leads to the control of viremia and the progressive decay in the HIV reservoir as observed in both studies.

A CD45RA$^+$ T$_{SCM}$ subset was previously described with characteristics of conventional memory T cells, enhanced self-renewal and the capacity to differentiate into other memory subsets. A CD45RA+CD45RO+CCR7+CD27+ CD95+T$_{SCM}$-like phenotype has been previously reported following in-vitro expansion of purified CD4+ and CD8+ naive T cells that were co-stimulated in the presence of cytokines such as IL-2, IL-7, IL-15, or IL-21; however, the potential of these cells to persist in-vivo and whether a proportion of these cells could revert to the CD45RA+ CD45RO-phenotype was not investigated. In addition, a CD4+ subset expressing low levels of CD45RA and CD45RO was seen to emerge in-vivo upon ART initiation combined with IL-2 therapy that correlated with CD4+ T cell increases, demonstrating that CD45RA$^{int}$RO$^{int}$ cells can also be generated in-vivo in response to homeostatic proliferation. The CD45RA$^{int}$RO$^{int}$ T$_{SCM}$ subset we have identified in this study, also demonstrated the capacity of self-renewal as observed by geneset enrichment of the Wnt-signaling cascade. We further observed an upregulation of additional mechanisms of stemness (SOX genes) as well as enhancement of pro-inflammatory and apoptotic signatures which were unique to the CD45RA$^{int}$RO$^{int}$ T$_{SCM}$ subset unlike the CD45RA$^+$ T$_{SCM}$ subset further highlighting the distinction between these T$_{SCM}$ populations.

T$_{SCM}$ have previously been shown to be permissive to HIV-infection. The importance of limiting HIV infection in early memory cells for the preservation of CD4+ T cell homeostasis has been shown in non-human primates as well as in viremic non-progressor HIV-infected individuals. The presence of T$_{SCM}$ cells (enriched in CCR5 gene edited alleles (up to ~40% in the periphery at years 3-4)) within secondary lymphoid tissues—where HIV replication would be partially if not totally inhibited—may lead to their long term survival. This in turn would lead to global improvements of adaptive immune function, increased CD4+ T cell numbers and control of HIV and other pathogens, and consequently a reduction in the size of the reservoir as we have shown in our current study. Indeed, we detected CCR5 gene edited cells unique to the T$_{SCM}$ subset in SB-728-T products in short-lived cells such as T$_{TM}$ and T$_{EM}$ at years 3-4, confirming the differentiation potential of T$_{SCM}$ into T$_{EM}$. Furthermore, these observations support the modelling of the homeostasis of CCR5 gene edited CD4+ T cell memory subsets, where we observed reduced death rates. In addition, the bi-phasic decay analysis of the HIV DNA excluded the possibility of dilution being the cause of the HIV decay. However, our multivariate model demonstrated that the long-term persistence of CCR5 gene edited CD45RA$^{int}$RO$^{int}$ T$_{SCM}$ does contribute to the decay of the HIV reservoir post infusion.

A central hypothesis was that providing protection from HIV infection to a small subset of T cells would provide a global benefit and allow for the control of viral replication. In support of this, results from both SB-728-0902 and SB-728-1101 studies confirm the role of SB-728-T infusion in restoration of T cell homeostasis and cognate help to HIV specific CD8 T cells that can lead to the differentiation of T$_{SCM}$ into T$_{EM}$ that are protected from HIV infection. The cognate help provided is further highlighted by the observed decay in HIV reservoir that negatively correlated with both the expansion of CD45RA$^{int}$RO$^{int}$ T$_{SCM}$ cells and GAG-specific CD8+ T$_{TM}$ IL-2 producing cells. The role of IL-2 production by HIV-specific CD8+ T cells on viral replication has previously been shown.

We recognized that our outcomes might be due to the ex vivo expansion of both CCR5 gene edited and gene unmodified T$_{SCM}$ cells within the infused products and that such cells would be protected in vivo by ART. In support of this hypothesis we observed a clear expansion of both CCR5 modified and unmodified cells post infusion. Interestingly, our model shows that the proliferation rates of CD45RA$^{int}$RO$^{int}$ T$_{SCM}$ were positively correlated with the cell counts of all CCR5 gene edited cells. It should be noted, however, that previous studies with adoptively transferred anti-CD3/CD28 co-stimulated CCR5 unmodified cells failed to result in sustained increases in CD4+ T cell counts in HIV+participants. We are now performing a randomized clinical trial in which we can infuse CCR5 modified versus unmodified cells to more definitively address this question.

The results described here demonstrate that a single infusion of CCR5 gene edited cells is safe, well tolerated, and can lead to a significant decrease in HIV DNA levels (and perhaps of replication competent HIV reservoir). In addition, long-term persistence of gene edited memory stem cells leads to the replacement of dysfunctional/infected older memory cells with new cells that are protected from infection thereby repopulating the immune system. The non-invasive and autologous aspect of this therapy makes it more accessible and less cumbersome than hematopoietic stem cell transplantation. Advances in zinc finger nuclease mRNA delivery through electroporation can allow multi-dose regimens, which would be expected to greatly improve CD4+ T cell counts. In line with this, multiple infusions of unmodified anti-CD3/CD28 co-stimulated unmodified CD4+ T cells every 8 weeks have previously led to significant increases in cell counts one year post infusion. In addition, as CD4+ T cell count increases following each infusion, the products generated subsequently are also expected to yield greater engraftment and persistence, as it was shown that products from HIV+subjects with higher CD4+ T cell counts expanded better in-vitro compared to those with low CD4+ T cell counts. Furthermore, results from statistical analysis of HIV DNA showed a partial reduction of the reservoir by 6 weeks of infusion suggesting that optimal achievement of viral load control could occur if treatment would have been interrupted after an extended period in line with the second phase of the decay.

In summary, our results indicate that infusion of CCR5 gene edited cells provides a unique therapeutic intervention that improves T cell homeostasis and reduces the total HIV reservoir. Theoretically, combining this approach with other interventions might further improve outcomes.

While this invention has been particularly shown and described with references to preferred embodiments thereof, it will be understood by those skilled in the art that various changes in form and details may be made therein without departing from the scope of the invention encompassed by the appended claims. All patents, publications and references cited in the foregoing specification are herein incorporated by reference in their entirety.

Having described the invention, the following is claimed:

1. A method of generating an enriched population of long-lived CD4 T cells that are devoid of a functional CCR5 and/or CXCR4 HIV co-receptor; the method comprising:

isolating CD4 T cells from a biological sample of a subject;

separating and/or enriching isolated CD4 T cells into cells having a CD45RA$^{int}$CD45RO$^{int}$ phenotype and an increased expression of TCF7 compared to the isolated CD4 T cells prior to separation and/or enrichment, wherein enriching includes culturing the isolated CD4 T cells in the presence of IL-7 and IL-15 effective to promote expansion and/or formation of an enriched population of CD4 T cells having the CD45RA$^{int}$CD45RO$^{int}$ phenotype, wherein the concentration of IL-7 and IL-15 is less than 10 ng/ml, and wherein at least 50% of the separated and/or enriched population of CD4 T cells have a CD45RA$^{int}$CD45RO$^{int}$CD95+CD127+CD27+ phenotype; and modifying the CD4 T cells such that the CD4 T cells are devoid of a functional CCR5 and/or CXCR4 HIV co-receptor before separating and/or enriching the isolated CD4 T cells into cells having the CD45RA$^{int}$CD45RO$^{int}$ phenotype and/or modifying the separated and/or enriched CD4 T cells having the CD45RA$^{int}$CD45RO$^{int}$ phenotype such that the CD4 T cells having the CD45RA$^{int}$CD45RO$^{int}$ phenotype are devoid of a functional CCR5 and/or CXCR4 HIV co-receptor.

2. The method of claim 1, wherein the biological sample comprises isolated peripheral blood mononuclear cells from the subject.

3. The method of claim 1, wherein the separated and/or enriched CD4 T cells express at least one of CD95, CD127, or CD27.

4. The method of claim 1, wherein the separated and/or enriched CD4 T cells intermediately express 4-1BB.

5. The method of claim 1, wherein the separated and/or enriched CD4 T cells express at least one of IL17RA, CD5, IL2RG, IGF2R, SLC38A1, IL7R, SLC44A2, SLC2A3, CD96, CD44, CD6, CCR4, IL4R, or SLC12A7.

6. The method of claim 1, wherein the separated and/or enriched CD4 T cells have a CD45RA$^{int}$CD45RO$^{int}$CD95+CD127+CD27+TCF7+ phenotype.

7. The method of claim 1, wherein the separated and/or enriched CD4 T cells have a
CD45RA$^{int}$CD45RO$^{int}$CD95+CD127+CD27+TCF7+CD44+ SCL38A1+IL2RG+CD6+CD5+ phenotype.

8. The method of claim 1, further comprising activating the isolated CD4 T cells with an anti-CD3 antibody and/or an anti-CD28 antibody.

9. The method of claim 1, further comprising culturing the enriched population of CD4 T cells having the CD45RA$^{int}$CD45RO$^{int}$ phenotype in a culture medium comprising TGFβ and IL1β to maintain the CD45RA$^{int}$CD45RO$^{int}$ phenotype.

10. The method of claim 1, wherein the CD4 T cells devoid of the functional CCR5 and/or CXCR4 HIV co-receptor are modified by inactivating a gene encoding CCR5 and/or CXCR4.

11. The method of claim 10, wherein the isolated T cells are genetically modified by at least one of transduction, transfection, and/or electroporation.

12. An isolated enriched CD4+ T cell population, the T cell population characterized by intermediate cells surface co-expression of CD45A and CD450 (RA$^{int}$RO$^{int}$) and expression of CD95+, CD127+, TCF7+ and CD27+, wherein the cells are modified such that they are devoid of a functional CCR5 and/or CXCR4 HIV co-receptor, wherein at least 50% of the enriched population of CD4+ T cells have a CD45RA$^{int}$CD45RO$^{int}$CD95+CD127+CD27+ phenotype.

13. The population of claim 12, upon administration to a subject infected with HIV being capable of promoting at least one of a sustained increase in absolute CD4 cell numbers, restoring HIV specific T cell immunity, or substantial decaying in HIV reservoir in the subject.

14. A method of treating an HIV infected subject, the method comprising administering the subject the enriched T cell population of claim 12.

15. The method of claim 14, where the subject has undergone and/or continues to undergo antiretroviral therapy.

16. The method of claim 14, wherein the enriched T cell population is administered to the subject at an amount effective to promote at least one of a sustained increase in absolute CD4 cell numbers, restoration of HIV specific T cell immunity, or a substantial decay in HIV reservoir in the subject.

* * * * *